United States Patent
Kerns et al.

(10) Patent No.: US 12,378,519 B2
(45) Date of Patent: *Aug. 5, 2025

(54) MICROFLUIDIC MODEL OF THE BLOOD BRAIN BARRIER

(71) Applicants: EMULATE, Inc., Boston, MA (US); Cedars-Sinai Medical Center, Los Angeles, CA (US)

(72) Inventors: S. Jordan Kerns, Reading, MA (US); Norman Wen, West Roxbury, MA (US); Carolina Lucchesi, Westwood, MA (US); Christopher David Hinojosa, Cambridge, MA (US); Jacob Fraser, Somerville, MA (US); Geraldine Hamilton, Boston, MA (US); Gad Vatine, Los Angeles, CA (US); Samuel Sances, Santa Monica, CA (US); Clive Svendsen, Pacific Palisades, CA (US); Daniel Levner, Brookline, MA (US); Dhruv Sareen, Porter Ranch, CA (US)

(73) Assignees: EMULATE, INC., Boston, MA (US); CEDARS-SINAI MEDICAL CENTER, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/529,198

(22) Filed: Dec. 5, 2023

(65) Prior Publication Data

US 2024/0228954 A1  Jul. 11, 2024

Related U.S. Application Data

(63) Continuation of application No. 15/768,736, filed as application No. PCT/US2016/057724 on Oct. 19, 2016.

(Continued)

(51) Int. Cl.
  *C12N 5/0793* (2010.01)
  *C12M 1/12* (2006.01)
  (Continued)

(52) U.S. Cl.
  CPC ......... *C12N 5/0619* (2013.01); *C12N 5/0622* (2013.01); *C12N 5/069* (2013.01);
  (Continued)

(58) Field of Classification Search
  CPC .... C12N 5/0619; C12N 5/0622; C12N 5/069; C12N 5/0692; C12N 5/0618;
  (Continued)

(56) References Cited

U.S. PATENT DOCUMENTS

| 8,647,861 B2 | 2/2014 | Ingber et al. ............... 435/289.1 |
| 9,034,571 B2 | 5/2015 | Berry et al. ................... 435/1.1 |

(Continued)

FOREIGN PATENT DOCUMENTS

| WO | WO/1994/016059 | 7/1994 |
| WO | WO/2010/009307 | 1/2010 |

(Continued)

OTHER PUBLICATIONS

Kerns et al., U.S. Appl. No. 15/768,736; Apr. 16, 2018.*

(Continued)

*Primary Examiner* — Michael L Hobbs
(74) *Attorney, Agent, or Firm* — Medlen & Carroll, LLP

(57) ABSTRACT

The invention relates to culturing brain endothelial cells, and optionally astrocytes and neurons in a fluidic device under conditions whereby the cells mimic the structure and function of the blood brain barrier. Culture of such cells in a microfluidic device, whether alone or in combination with other cells, drives maturation and/or differentiation further than existing systems.

13 Claims, 34 Drawing Sheets

Related U.S. Application Data

(60) Provisional application No. 62/380,780, filed on Aug. 29, 2016, provisional application No. 62/332,727, filed on May 6, 2016, provisional application No. 62/277,723, filed on Jan. 12, 2016, provisional application No. 62/243,642, filed on Oct. 19, 2015.

(51) Int. Cl.
    C12N 5/071     (2010.01)
    C12N 5/079     (2010.01)
    C12Q 1/02      (2006.01)
    B01L 3/00      (2006.01)
    C12M 1/42      (2006.01)
    C12M 3/06      (2006.01)

(52) U.S. Cl.
    CPC ............ C12N 5/0692 (2013.01); C12Q 1/02 (2013.01); B01L 3/5027 (2013.01); B01L 2200/0647 (2013.01); B01L 2300/0861 (2013.01); C12M 23/16 (2013.01); C12M 25/02 (2013.01); C12M 35/08 (2013.01); C12N 5/0618 (2013.01); C12N 2502/081 (2013.01); C12N 2502/086 (2013.01); C12N 2502/28 (2013.01); C12N 2506/45 (2013.01); C12N 2531/00 (2013.01); C12N 2533/52 (2013.01); C12N 2533/54 (2013.01); C12N 2533/56 (2013.01); C12N 2535/10 (2013.01); C12N 2539/00 (2013.01)

(58) Field of Classification Search
    CPC ........ C12N 2502/081; C12N 2502/086; C12N 2502/28; C12N 2506/45; C12N 2531/00; C12N 2533/52; C12N 2533/54; C12N 2533/56; C12N 2535/10; C12N 2535/2539; C12N 13/00; C12N 15/87; C12N 15/8207; C12N 15/8206; C12M 23/16; C12M 23/12; C12M 25/02; C12M 35/08; C12M 35/02; C12M 35/04; B01L 3/5027; B01L 3/502761; B01L 2200/0647; B01L 2300/0861; H03K 3/57; A61N 1/3096; A61K 48/00; A61K 38/00; G01N 33/48728
    See application file for complete search history.

(56) References Cited

U.S. PATENT DOCUMENTS

| | | | | |
|---|---|---|---|---|
| 11,174,462 | B2 * | 11/2021 | Kerns .................. | C12N 5/0692 |
| 2005/0282148 | A1 | 12/2005 | Warren et al. ................. | 435/372 |
| 2007/0077649 | A1 | 4/2007 | Sammak et al. ............. | 435/325 |
| 2007/0224677 | A1 | 9/2007 | Neumann ..................... | 435/325 |
| 2008/0044847 | A1 * | 2/2008 | Shusta ................. | C12N 5/0691 |
| | | | | 435/325 |
| 2012/0107934 | A1 | 5/2012 | Poole ........................... | 435/377 |
| 2012/0171354 | A1 | 7/2012 | O'Neill et al. .............. | 427/2.25 |
| 2012/0211373 | A1 | 8/2012 | El-Sayed et al. ............. | 205/778 |
| 2012/0282682 | A1 | 11/2012 | Walsh et al. .................. | 422/417 |
| 2013/0029419 | A1 | 1/2013 | Shusta et al. .................. | 435/325 |
| 2013/0173018 | A1 | 7/2013 | Sakaguchi et al. ........... | 435/395 |
| 2013/0203086 | A1 | 8/2013 | Achyuta et al. ............. | 435/7.92 |
| 2013/0344529 | A1 | 12/2013 | Giselbrecht et al. ........... | 435/29 |
| 2014/0065660 | A1 | 3/2014 | Kim et al. ................. | 435/297.2 |
| 2014/0093905 | A1 | 4/2014 | Ingber et al. ............. | 435/289.1 |
| 2014/0142370 | A1 | 5/2014 | Wong et al. ..................... | 600/36 |
| 2015/0004077 | A1 | 1/2015 | Wikswo et al. ............. | 422/502 |
| 2015/0023911 | A1 | 1/2015 | Schilling et al. ............. | 435/325 |
| 2015/0079584 | A1 | 3/2015 | Gevaert et al. ............. | 435/30 |
| 2015/0087004 | A1 | 3/2015 | Chen et al. ..................... | 435/29 |

FOREIGN PATENT DOCUMENTS

| | | | |
|---|---|---|---|
| WO | WO/2012/118799 | 9/2012 | |
| WO | WO/2013/086486 | 6/2013 | |
| WO | WO/2013/086502 | 6/2013 | |
| WO | WO/2014/210364 | 12/2014 | |
| WO | WO/2015/013332 | 1/2015 | |
| WO | WO/2015/138032 | 9/2015 | |
| WO | WO/2015/138034 | 9/2015 | |
| WO | WO-2015138032 A2 * | 9/2015 | ............ B01D 61/18 |
| WO | WO/2017/035119 | 3/2017 | |
| WO | WO/2019/178251 | 9/2019 | |
| WO | WO/2020/198693 | 10/2020 | |

OTHER PUBLICATIONS

Kerns et al., U.S. Appl. No. 15/352,289; Nov. 15, 2016.*
Abbott, N. J. et al. (2010) "Structure and function of the blood-brain barrier," *Neurobiology of Disease* 37(1), 13-25.
Abbott, N. J. et al. (2006) "Astrocyte-endothelial interactions at the blood-brain barrier," *Nature Reviews. Neuroscience* 7(1), 41-53.
Achyuta, A. K. et al. (2013) "A modular approach to create a neurovascular unit-on-a-chip," *Lab on a Chip* 13(4), 542-553.
Adriani, G. et al. (2015) "Modeling the Blood-Brain Barrier in a 3D triple co-culture microfluidic system," *Conference proceedings—IEEE Engineering in Medicine and Biology Society* 2015, 338-341.
Alcendor, D. J. et al. (2012) "Infection and upregulation of proinflammatory cytokines in human brain vascular pericytes by human cytomegalovirus," *Journal of Neuroinflammation* 9, 95.
Aloisi, F. et al. (1992) "Production of hemolymphopoietic cytokines (IL-6, IL-8, colony-stimulating factors) by normal human astrocytes in response to IL-1 beta and tumor necrosis factor-alpha," *Journal of Immunology* 149(7), 2358.
Annabi, N. et al. (2010) "Controlling the porosity and microarchitecture of hydrogels for tissue engineering," *Tissue Engineering Part B: Reviews* 16(4), 371-383.
Armulik, A. et al. (2010) "Pericytes regulate the blood-brain barrier," *Nature* 468(7323), 557-561.
Bell, R. D. et al. (2009) "Neurovascular mechanisms and blood-brain barrier disorder in Alzheimer's disease," *Acta neuropathologica* 118(1), 103-113.
Bischel, L. L. et al. (2012) "A Practical Method for Patterning Lumens through ECM Hydrogels via Viscous Finger Patterning," *Journal of Laboratory Automation* 17(2), 96-103.
Bischel, L. L. et al. (2013) "Tubeless microfluidic angiogenesis assay with three-dimensional endothelial-lined microvessels," *Biomaterials* 34(5), 1471-1477.
Booth, R. et al. (2012) "Characterization of a microfluidic in vitro model of the blood-brain barrier (µBBB)," *Lab on a Chip* 12(10), 1784-1792.
Booth, R. et al. (2014) "Permeability Analysis of Neuroactive Drugs Through a Dynamic Microfluidic In Vitro Blood-Brain Barrier Model," *Annals of Biomedical Engineering* 42(12), 2379-2391.
Booth, R. H. (2014) A Microfluidic in Vitro Model of the Blood-Brain Barrier, in *Department of Bioengineering*, p. 177, The University of Utah.
Brown, J. A. et al. (2015) "Recreating blood-brain barrier physiology and structure on chip: A novel neurovascular microfluidic bioreactor," *Biomicrofluidics* 9(5), 054124-054124.
Cashman, C. R. et al. (2013) "Induced Pluripotent Stem Cells and Motor Neuron Disease: Toward an Era of Individualized Medicine." *Journal of Neuroscience* 33(20), 8587-8589.
Cecchelli, R. et al. (2007) "Modelling of the blood-brain barrier in drug discovery and development," *Nature Reviews Drug Discovery* 6(8), 650-661.
Chaudhuri, A. et al. (2008) "HIV-1 activates proinflammatory and interferon-inducible genes in human brain microvascular endothelial cells: putative mechanisms of blood-brain barrier dysfunction," *Journal of Cerebral Blood Flow & Metabolism* 28(4), 697-711.
Cho, H. et al. (2015) "Three-Dimensional Blood-Brain Barrier Model for in vitro Studies of Neurovascular Pathology." *Scientific Reports* 5(1), Article No. 15222.

(56) References Cited

OTHER PUBLICATIONS

Choi, S. S. et al. (2014) "Human astrocytes: secretome profiles of cytokines and chemokines," *PLoS One* 9(4), Article No. e92325-e92325.
Corps, K. N. et al. (2015) "Inflammation and neuroprotection in traumatic brain injury," *JAMA Neurology* 72(3), 355-362.
Cucullo, L. et al. (2008) "Immortalized human brain endothelial cells and flow-based vascular modeling: a marriage of convenience for rational neurovascular studies," *Journal of Cerebral Blood Flow & Metabolism* 28(2), 312-328.
Cucullo, L. et al. (2011) "The role of shear stress in Blood-Brain Barrier endothelial physiology," *BMC Neuroscience* 12, 40.
Cucullo, L. et al. (2013) "A new dynamic in vitro modular capillaries-venules modular system: Cerebrovascular physiology in a box." *BMC Neuroscience* 14(1), 18.
Cucullo, L. et al. (2002) "A new dynamic in vitro model for the multidimensional study of astrocyte-endothelial cell interactions at the blood-brain barrier," *Brain Research* 951(2), 243-254.
Davis, G. E. et al. (2005) "Endothelial extracellular matrix: biosynthesis, remodeling, and functions during vascular morphogenesis and neovessel stabilization." *Circulation Research* 97(11), 1093-1107.
Deli, M. A. et al. (2005) "Permeability Studies on In Vitro Blood-Brain Barrier Models:Physiology, Pathology, and Pharmacology," *Cellular and Molecular Neurobiology* 25(1), 59-127.
Deli, M. A. et al. (1995) "Exposure of tumor necrosis factor-alpha to luminal membrane of bovine brain capillary endothelial cells cocultured with astrocytes induces a delayed increase of permeability and cytoplasmic stress fiber formation of actin," *Journal of Neuroscience Research* 41(6), 717-726.
Deosarkar, S. P. et al. (2015) "A Novel Dynamic Neonatal Blood-Brain Barrier on a Chip," *PLoS One* 10(11), Article No. e0142725.
Dhumpa, R. et al. (2012) "Temporal gradients in microfluidic systems to probe cellular dynamics: a review," *Analytica Chimica Acta* 743, 9-18.
Dimos, J. T. et al. (2008) "Induced Pluripotent Stem Cells Generated from Patients with ALS Can Be Differentiated into Motor Neurons," *Science* 321(5893), 1218-1221.
Dong, B. et al. (2010) "Lattice Boltzmann simulation of viscous fingering phenomenon of immiscible fluids displacement in a channel." *Computers & Fluids* 39(5), 768-779.
Douville, N. J. et al. (2010) "Fabrication of Two-Layered Channel System with Embedded Electrodes to Measure Resistance Across Epithelial and Endothelial Barriers," *Analytical Chemistry* 82(6), 2505-2511.
Ebert, A. D. et al. (2013) "EZ spheres: A stable and expandable culture system for the generation of pre-rosette multipotent stem cells from human ESCs and iPSCs," *Stem Cell Research* 10(3), 417-427.
Erta, M. et al. (2012) "Interleukin-6, a major cytokine in the central nervous system," *International Journal of Biological Sciences* 8(9), 1254-1266.
Farina, C et al. (2007) "Astrocytes are active players in cerebral innate immunity," *Trends in Immunology* 28(3), 138-145.
Fee, D. et al. (2000) "Interleukin 6 Promotes Vasculogenesis of Murine Brain Microvessel Endothelial Cells," *Cytokine* 12(6), 655-665.
Förster, C. et al. (2008) "Differential effects of hydrocortisone and TNFalpha on tight junction proteins in an in vitro model of the human blood-brain barrier," *Journal of Physiology* 586(7), 1937-1949.
Gaillard, P. J et al. (2001) "Establishment and functional characterization of an in vitro model of the blood-brain barrier, comprising a co-culture of brain capillary endothelial cells and astrocytes," *European Journal of Pharmaceutical Sciences* 12(3), 215-222.
Gibson, C. L. et al. (2005) "G-CSF reduces infarct vol. and improves functional outcome after transient focal cerebral ischemia in mice," *Journal of Cerebral Blood Flow & Metabolism* 25(4), 431-439.

Griep, L. M. et al. (2013) "BBB on chip: microfluidic platform to mechanically and biochemically modulate blood-brain barrier function," *Biomedical Microdevices* 15(1), 145-150.
Gross, P. G et al. (2007) "Applications of microfluidics for neuronal studies," *Journal of the Neurological Sciences* 252, 135-143.
Hasan, A. et al. (2015) "A multilayered microfluidic blood vessel-like structure," *Biomedical Microdevices* 17(5), 88.
Hauser, S. L. et al. (2006) "The Neurobiology of Multiple Sclerosis: Genes, Inflammation, and Neurodegeneration," *Neuron* 52(1), 61-76.
Hawkins, B. T. et al. (2005) "The Blood-Brain Barrier/Neurovascular Unit in Health and Disease," *Pharmacological Reviews* 57(2), 173-185.
Herland, A. et al. (2016) "Distinct Contributions of Astrocytes and Pericytes to Neuroinflammation Identified in a 3D Human Blood-Brain Barrier on a Chip," *PLoS One* 11(3), Article No. e0150360.
Hofman, F. M. et al. (1999) "HIV-1 tat protein induces the production of interleukin-8 by human brain-derived endothelial cells," *Journal of Neuroimmunology* 94(1), 28-39.
Huxley, V. H. et al. (1987) "Quantitative fluorescence microscopy on single capillaries: alpha-lactalbumin transport," *American Journal of Physiology* 252(1 Pt 2), H188-197.
Jansson, D. et al. (2014) "A role for human brain pericytes in neuroinflammation," *Journal of Neuroinflammation* 11(1), 104.
Jones, S. A. (2005) "Directing Transition from Innate to Acquired Immunity: Defining a Role for IL-6," *Journal of Immunology* 175(6), 3463.
Kang, Q. et al. (2004) "Immiscible displacement in a channel: simulations of fingering in two dimensions," *Advances in Water Resources* 27(1), 13-22.
Kelamangalath, L. et al. (2011) "K-Opioid Receptor Inhibition of Calcium Oscillations in Spinal Cord Neurons," *Molecular Pharmacology* 79(6), 1061-1071.
Kim, D. et al. (2013) "Protein immobilization techniques for microfluidic assays," *Biomicrofluidics* 7(4), 41501-41501.
Kim, J. A. et al. (2015) "Collagen-based brain microvasculature model in vitro using three-dimensional printed template," *Biomicrofluidics* 9(2), 024115-024115.
Kong, D. et al. (2004) "Cytokine-Induced Mobilization of Circulating Endothelial Progenitor Cells Enhances Repair of Injured Arteries," *Circulation* 110(14), 2039-2046.
Kossmann, T. et al. (1997) "Interleukin-8 released into the cerebrospinal fluid after brain injury is associated with blood-brain barrier dysfunction and nerve growth factor production," *Journal of Cerebral Blood Flow & Metabolism* 17(3), 280-289.
Kovac, A. et al. (2011) "Brain microvascular pericytes are immunoactive in culture: cytokine, chemokine, nitric oxide, and LRP-1 expression in response to lipopolysaccharide," *Journal of Neuroinflammation* 8, 139.
Kuo, Y.-C. et al. (2011) "Effect of human astrocytes on the characteristics of human brain-microvascular endothelial cells in the blood-brain barrier," *Colloids and Surfaces B: Biointerfaces* 86(1), 225-231.
Liebner, S. et al. (2011) "Current concepts of blood-brain barrier development," *The International Journal of Developmental Biology* 55(4-5), 467-476.
Lin, H. J. et al. (2004) "Neural stem cell differentiation in a cell-collagen-bioreactor culture system," *Developmental Brain Research* 153(2), 163-173.
Lippmann, E. S. et al. (2014) "A retinoic acid-enhanced, multicellular human blood-brain barrier model derived from stem cell sources," *Scientific Reports* 4, Article No. 4160.
Lippmann, E. S. et al. (2013) "Modeling the blood-brain barrier using stem cell sources," *Fluids and Barriers of the CNS* 10(1), 1-14.
Lippmann, E. S. et al. (2012) "Human Blood-Brain Barrier Endothelial Cells Derived from Pluripotent Stem Cells," *Nature Biotechnology* 30(8), 783-791.
Mabondzo, A. et al. (2010) "Validation of In Vitro Cell-Based Human Blood-Brain Barrier Model Using Clinical Positron Emission Tomography Radioligands to Predict In Vivo Human Brain Penetration," *Molecular Pharmaceutics* 7(5), 1805-1815.
Minagar, A. et al. (2003) "Blood-brain barrier disruption in multiple sclerosis," *Multiple Sclerosis* 9(6), 540-549.

(56) References Cited

OTHER PUBLICATIONS

Moya, M. L. et al. (2013) "In vitro perfused human capillary networks," *Tissue Engineering Part C Methods* 19(9), 730-737.
Naik, P. et al. (2012) "<em>In Vitro</em> Blood–Brain Barrier Models: Current and Perspective Technologies," *Journal of Pharmaceutical Sciences* 101(4), 1337-1354.
Nakagawa, S. et al. (2009) "A new blood-brain barrier model using primary rat brain endothelial cells, pericytes and astrocytes," *Neurochemistry International* 54(3), 253-263.
Nakagawa, S. et al. (2007) "Pericytes from brain microvessels strengthen the barrier integrity in primary cultures of rat brain endothelial cells," *Cell and Molecular Neurobiology* 27(6), 687-694.
Nehme, A. et al. (2008) "Dexamethasone inhibits high glucose-, TNF-alpha-, and IL-1beta-induced secretion of inflammatory and angiogenic mediators from retinal microvascular pericytes," *Investigative Ophthalmology & Visual Science* 49(5), 2030-2038.
Niego, B. e et al. (2013) "Improved Method for the Preparation of a Human Cell-based, Contact Model of the Blood-Brain Barrier," *Journal of Visualized Experiments*(81), 50934.
Okita, K et al. (2011) "A more efficient method to generate integration-free human iPS cells," *Nature Methods* 8(5), 409-412.
Park, J. H. et al. (2010) "Microporous cell-laden hydrogels for engineered tissue constructs," *Biotechnology and Bioengineering* 106(1), 138-148.
Penkowa, M. et al. (2000) "Impaired inflammatory response and increased oxidative stress and neurodegeneration after brain injury in interleukin-6-deficient mice," *Glia* 32(3), 271-285.
Prabhakarpandian, B. et al. (2013) "SyM-BBB: a microfluidic Blood Brain Barrier model," *Lab on a chip* 13(6), 1093-1101.
Probert, L. (2015) "TNF and its receptors in the CNS: The essential, the desirable and the deleterious effects," *Neuroscience* 302, 2-22.
Roberts, L. M. et al. (2008) "Expression of the Thyroid Hormone Transporters Monocarboxylate Transporter-8 (SLC16A2) and Organic Ion Transporter-14 (SLCO1C1) at the Blood-Brain Barrier," *Endocrinology* 149(12), 6251-6261.
Rosenberg, S. S. et al. (2011) "Calcium Signaling in Neuronal Development," *Cold Spring Harbor Perspectives in Biology* 3(10).
Santaguida, S. et al. (2006) "Side by side comparison between dynamic versus static models of blood-brain barrier in vitro: a permeability study," *Brain research* 1109(1), 1-13.
Sareen, D. et al. (2014) "Human neural progenitor cells generated from induced pluripotent stem cells can survive, migrate, and integrate in the rodent spinal cord," *Journal of Comparative Neurology* 522(12), 2707-2728.
Sareen, D. et al. (2013) "Targeting RNA foci in iPSC-derived motor neurons from ALS patients with C9ORF72 repeat expansion," *Science Translational Medicine* 5(208), Article No. 208ra149.
Schäbitz, W. R. et al. (2003) "Neuroprotective Effect of Granulocyte Colony-Stimulating Factor After Focal Cerebral Ischemia," *Stroke* 34(3), 745-751.
Schneider, A. et al. (2005) "The hematopoietic factor G-CSF is a neuronal ligand that counteracts programmed cell death and drives neurogenesis," *Journal of clinical investigation* 115(8), 2083-2098.
Schwartz, C. E. et al. (2005) "Allan-Herndon-Dudley Syndrome and the Monocarboxylate Transporter 8 (MCT8) Gene," *American Journal of Human Genetics* 77(1), 41-53.
Sellgren, K. L. et al. (2015) "An optically transparent membrane supports shear stress studies in a three-dimensional microfluidic neurovascular unit model," *Biomicrofluidics* 9(6), 061102.
Semple, B. D. et al. (2010) "Deficiency of the chemokine receptor CXCR2 attenuates neutrophil infiltration and cortical damage following closed head injury," *Neurobiology of Disease* 40(2), 394-403.
Shibata, K. et al. (2007) Collagen micro flow channel for in vitro Blood-Brain Barrier model, in *2007 Digest of papers Microprocesses and Nanotechnology*, pp. 510-511.
Song, J. W. et al. (2011) "Fluid forces control endothelial sprouting," *Proceedings of the National Academy of Sciences of the United States of America* 108(37), 15342-15347.
Swartz, K. R. et al. (2001) "Interleukin-6 promotes post-traumatic healing in the central nervous system," *Brain research* 896(1-2), 86-95.
Sweeney, M. D. et al. (2018) "Blood-brain barrier breakdown in Alzheimer disease and other neurodegenerative disorders," *Nature Reviews Neurology* 14(3), 133-150.
Syvänen, S. et al. (2009) "Species Differences in Blood-Brain Barrier Transport of Three Positron Emission Tomography Radioligands with Emphasis on P-Glycoprotein Transport," *Drug Metabolism and Disposition* 37(3), 635.
Tarkowski, E. et al. (1995) "Early Intrathecal Production of Interleukin-6 Predicts the Size of Brain Lesion in Stroke," *Stroke* 26(8), 1393-1398.
Telias, M. et al. (2014) "Electrical maturation of neurons derived from human embryonic stem cells," *F1000Research* 3, 196-196.
Thangawng, A. L. et al. (2007) "An ultra-thin PDMS membrane as a bio/micro-nano interface: fabrication and characterization," *Biomedical Microdevices* 9(4), 587-595.
Thomsen, L. B. et al. (2015) "A Triple Culture Model of the Blood-Brain Barrier Using Porcine Brain Endothelial cells, Astrocytes and Pericytes," *PLoS One* 10(8), Article No. e0134765.
Trickler, W. J. et al. (2014) "Porcine brain microvessel endothelial cells show pro-inflammatory response to the size and composition of metallic nanoparticles," *Drug Metabolism Reviews* 46(2), 224-231.
Urich, E. et al. (2013) "Multicellular self-assembled spheroidal model of the blood brain barrier," *Science Reports* 3, Article No. 1500.
Van Der Helm, M. W. et al. (2016) "Microfluidic organ-on-chip technology for blood-brain barrier research," *Tissue Barriers* 4(1), e1142493.
Van Der Meer, A. et al. (2015) "Blood-brain Barrier (BBB): An overview of the research of the blood-brain barrier using microfluidic devices," *RSC Nanoscience and Nanotechnology* 2015, 40-56.
Van Der Meer, A. D. et al. (2013) "Three-dimensional co-cultures of human endothelial cells and embryonic stem cell-derived pericytes inside a microfluidic device," *Lab on a Chip* 13(18), 3562-3568.
Van Dommelen, J. A. W. et al. (2010) "Mechanical properties of brain tissue by indentation: Interregional variation," *Journal of the Mechanical Behavior of Biomedical Materials* 3(2), 158-166.
Vatine, G. D. et al. (2019) "Human iPSC-Derived Blood-Brain Barrier Chips Enable Disease Modeling and Personalized Medicine Applications (Supplemental)," *Cell Stem Cell* 24(6), Supplemental Figures.
Vatine, G. D. et al. (2019) "Human iPSC-Derived Blood-Brain Barrier Chips Enable Disease Modeling and Personalized Medicine Applications," *Cell Stem Cell* 24(6), 995-1005.e1006.
Veszelka, S. et al. (2007) "Pentosan polysulfate protects brain endothelial cells against bacterial lipopolysaccharide-induced damages," *Neurochemistry International* 50(1), 219-228.
Villa, P. et al. (2007) "The interleukin-8 (IL-8/CXCL8) receptor inhibitor reparixin improves neurological deficits and reduces long-term inflammation in permanent and transient cerebral ischemia in rats," *Molecular Medicine* 13(3-4), 125-133.
Walter, F. R. et al. (2016) "A versatile lab-on-a-chip tool for modeling biological barriers," *Sensors and Actuators B: Chemical* 222, 1209-1219.
Wang, A. et al. (2020) "Generation of an induced pluripotent stem cell line (SHCDNi003-A) from a one-year-old Chinese Han infant with Allan-Herndon-Dudley syndrome," *Stem Cell Research* 46, 101872.
Warren, M. S. et al. (2009) "Comparative gene expression profiles of ABC transporters in brain microvessel endothelial cells and brain in five species including human," Pharmacological Research 59(6), 404-413.
Weksler, B. B. et al. (2005) "Blood-brain barrier-specific properties of a human adult brain endothelial cell line," *FASEB Journal* 19(13), 1872-1874.
Whitesides, G. M. et al. (2001) "Soft Lithography in Biology and Biochemistry," *Annual Review of Biomedical Engineering* 3(1), 335-373.
wikipedia.com. Gel—Wikipedia (https://en.wikipedia.org/wiki/Gel).

(56) References Cited

OTHER PUBLICATIONS

Wolburg, H. et al. (2003) "Localization of claudin-3 in tight junctions of the blood-brain barrier is selectively lost during experimental autoimmune encephalomyelitis and human glioblastoma multiforme," *Acta Neuropathologica* 105(6), 586-592.

Wyss-Coray, T. (2006) "Inflammation in Alzheimer disease: driving force, bystander or beneficial response?," *Nature Medicine* 12(9), 1005-1015.

Xiao, B.-G. et al. (2007) "Cell biology and clinical promise of G-CSF: immunomodulation and neuroprotection," *Journal of Cellular and Molecular Medicine* 11(6), 1272-1290.

Yamamoto, K et al. (2005) "Fluid shear stress induces differentiation of Flk-1-positive embryonic stem cells into vascular endothelial cells in vitro," American Journal of Physiology-Heart and Circulatory Physiology 288(4), H1915-H1924.

Yeon, J. H et al. (2012) "Reliable permeability assay system in a microfluidic device mimicking cerebral vasculatures," *Biomedical Microdevices* 14(6), 1141-1148.

Yeon, J. H. et al. (2012) "In vitro formation and characterization of a perfusable three-dimensional tubular capillary network in microfluidic devices," *Lab on a Chip* 12(16), 2815-2822.

Yousefzadeh-Chabok, S. et al. (2015) The Relationship Between Serum Levels of Interleukins 6, 8, 10 and Clinical Outcome in Patients With Severe Traumatic Brain Injury, in *Archives of trauma research*, p. e18357.

Yuan, W. et al. (2009) "Non-invasive measurement of solute permeability in cerebral microvessels of the rat," *Microvascular Research* 77(2), 166-173.

Zilio, C. et al. (2014) "Erratum to: Universal hydrophilic coating of thermoplastic polymers currently used in microfluidics," *Biomedical Microdevices* 16(3), 499-499.

Zsebo, K. M. et al. (1988) "Vascular endothelial cells and granulopoiesis: interleukin-1 stimulates release of G-CSF and GM-CSF," *Blood* 71(1), 99-103.

PCT Written Opinion in corresponding International Application No. PCT/US2016/029164 dated Feb. 7, 2017.

PCT International Search Report of International Application No. PCT/US2016/029164 dated Feb. 7, 2017.

European Search Report for Application No. 16858141.1 dated Mar. 15, 2019.

PCT International Search Report of International Application No. PCT/US2016/057724 dated Jan. 9, 2017.

\* cited by examiner

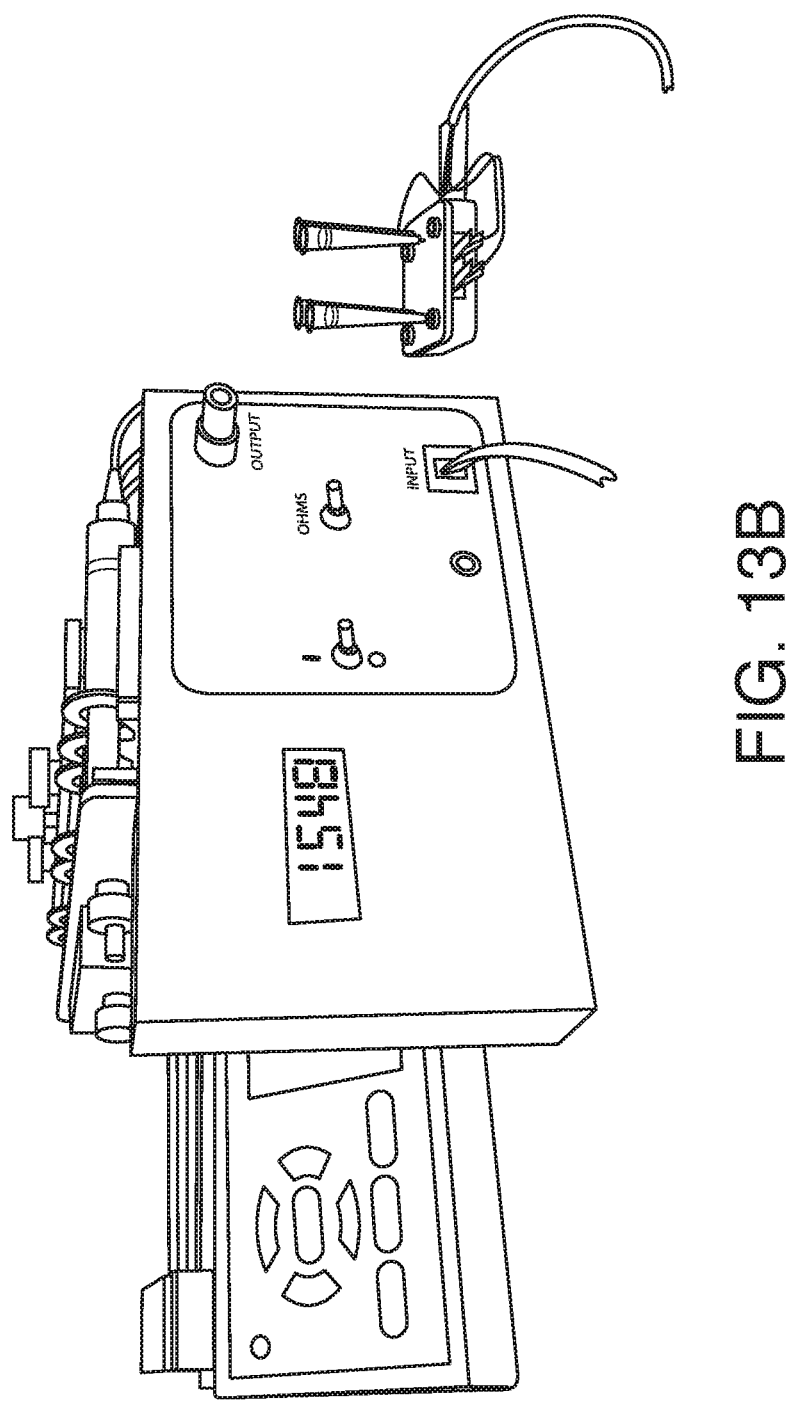

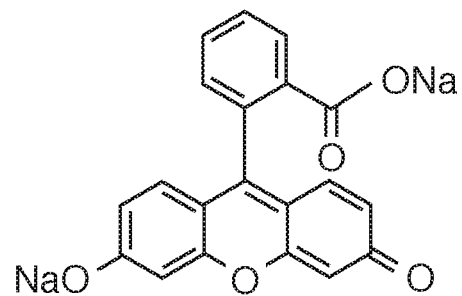
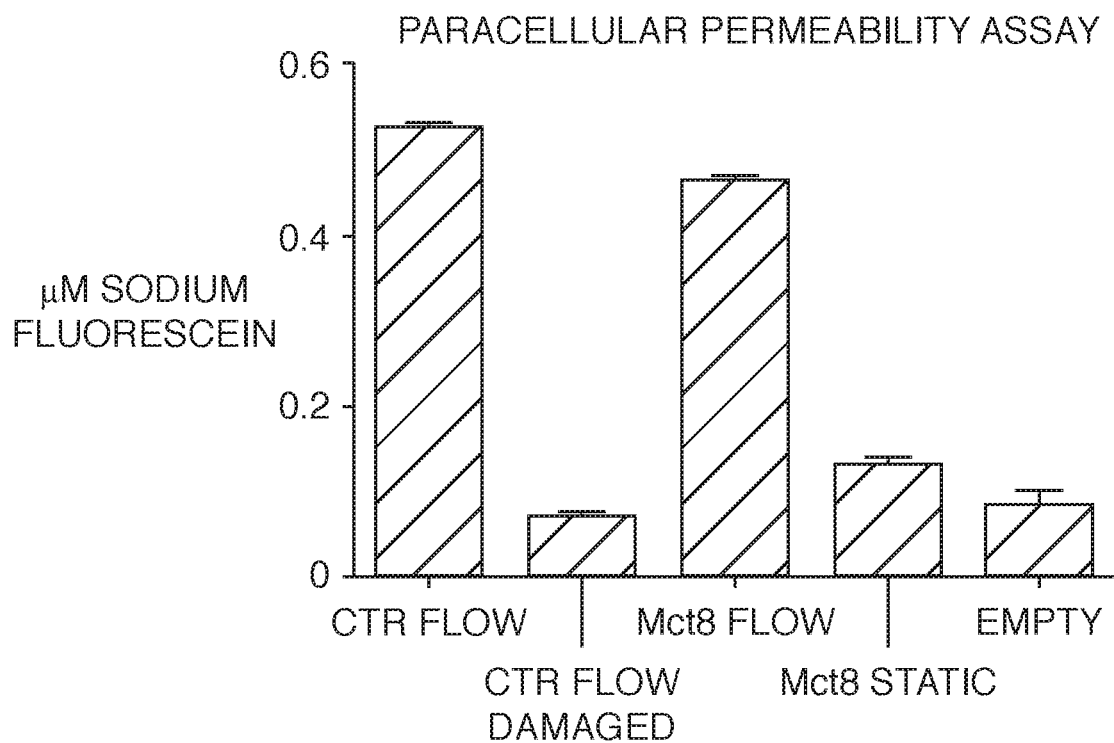
FIG. 15

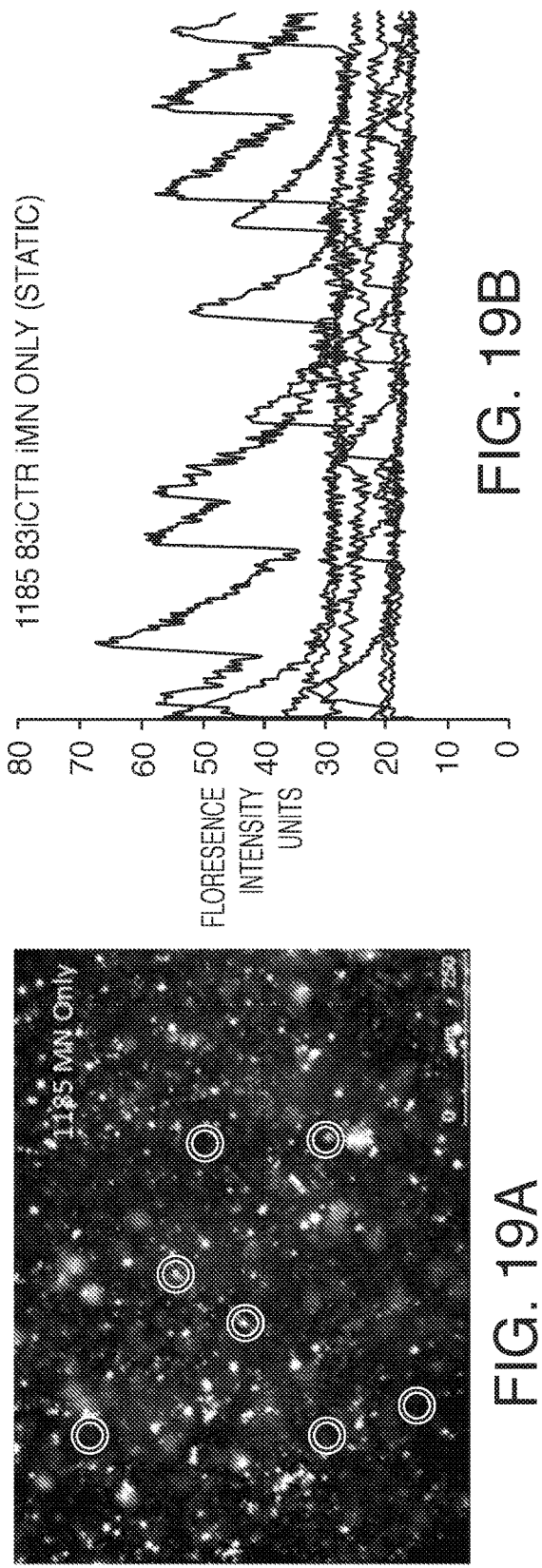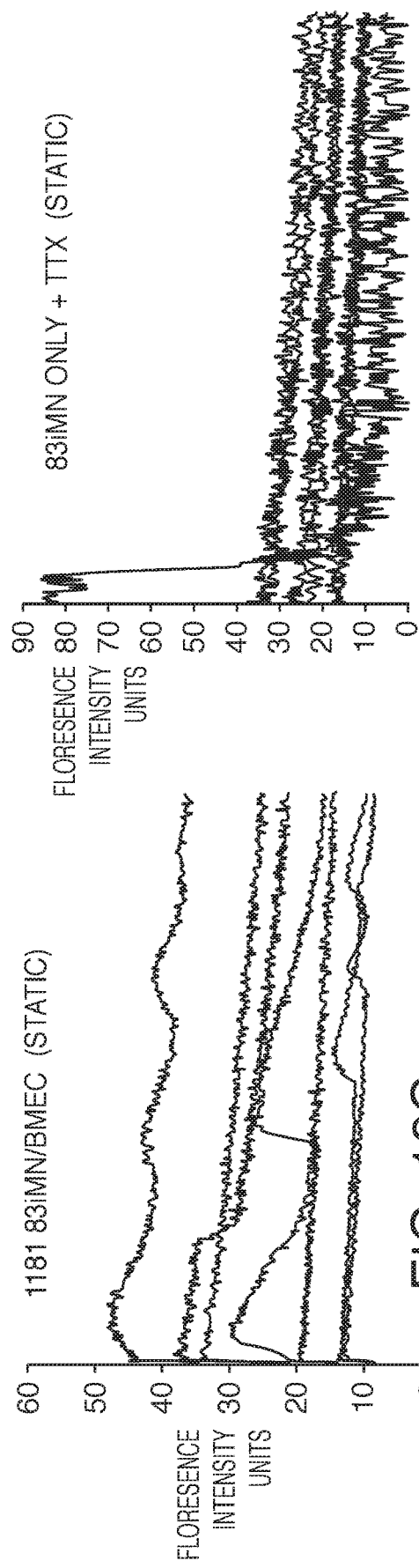
FIG. 19A
FIG. 19B
FIG. 19C
FIG. 19D

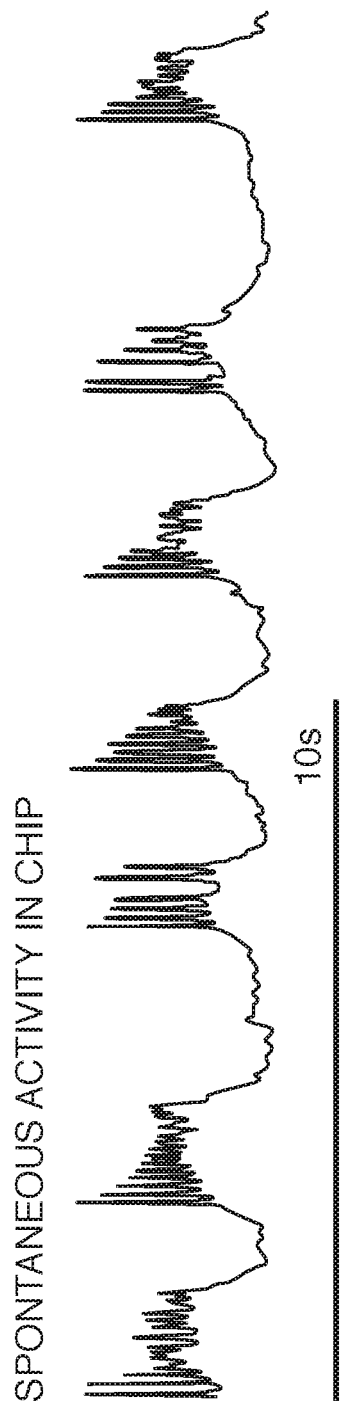
FIG. 24
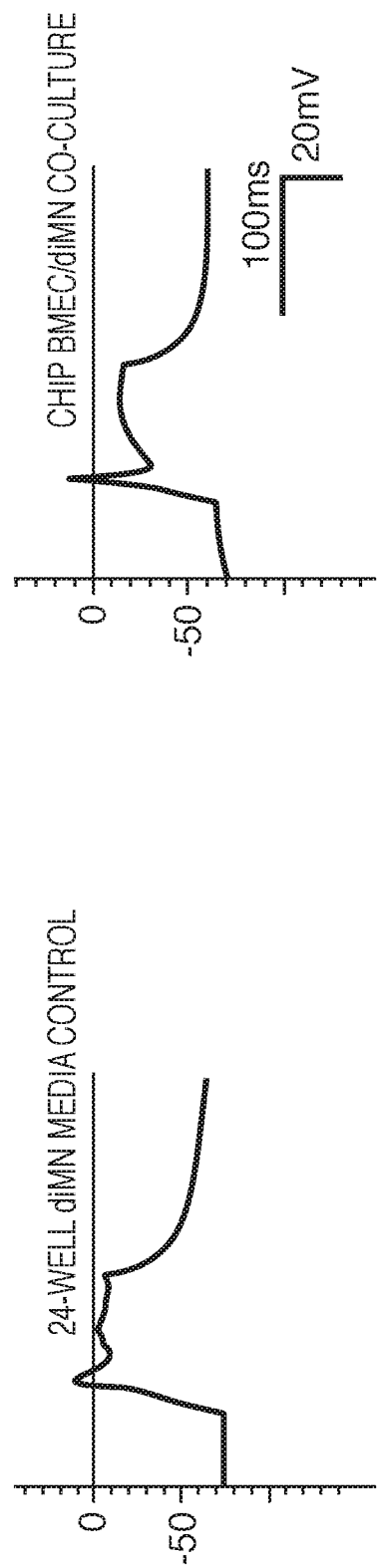
FIG. 25A
FIG. 25B

N = 3 (40-50 NEURONS EA.)

CTRL 96

ECCM 96

MN CHIP

MN/BMEC CHIP

| PC1: NEURAL DEVELOPMENT GENES | COUNT | BONFERRONI |
|---|---|---|
| NEURON DIFFERENTIATION | 25 | 2.46E-07 |
| DEVELOPMENTAL PROTEIN | 30 | 7.26E-08 |
| NEURON PROJECTION | 21 | 9.45E-08 |
| NEUROGENESIS | 14 | 3.89E-07 |
| AXON | 14 | 2.60E-06 |
| NEURON DEVELOPMENT | 19 | 8.85E-05 |
| CELL PROJECTION | 24 | 1.98E-04 |
| GROWRH CONE | 8 | 3.23E.04 |
| SITE OF POLARIZED GROWTH | 8 | 3.67E-04 |
| CELL MOTION | 20 | 2.88E-03 |
| BASIC HELIX-LOOP-HELIX DIMERISATION | 10 | 1.01E-03 |
| REGULATION NEURON DEFFERENTIATION | 11 | 3.90E-03 |

| PC2: CHIP INDUCED GENES | COUNT | BONFERRONI |
|---|---|---|
| RESPONSE TO PROTEIN STIMULUS | 9 | 0.0011 |
| NEURON DIFFERENTIATION | 15 | 0.0030 |
| CHROMOSOMAL PROTEIN | 8 | 0.0068 |
| NUCLEOSOME | 6 | 0.0082 |
| DNA-BINDING | 27 | 0.0139 |
| ID PROTEINS: G0-TO-S CELL CYCLE | 3 | 0.0260 |
| DEVELOPMENTAL PROTEIN | 16 | 0.0199 |
| HOMEOBOX | 9 | 0.0271 |
| PROTEIN-DNA COMPLEX | 6 | 0.0358 |
| EPITHELIUM DEVELOPMENT | 10 | 0.0393 |
| HOMEOBOX, CONSERVED SITE | 9 | 0.0435 |
| CHROMATIN | 8 | 0.0450 |

| PC3: VASCULAR INTERACTION GENES | COUNT | BONFERRONI |
|---|---|---|
| SIGNAL PEPTIDE | 65 | 2.68E-08 |
| EXTRACELLULAR REGION PART | 36 | 2.42E-08 |
| EXTRACELLULAR MATRIX | 22 | 3.23E-08 |
| SECRETED | 42 | 2.59E-07 |
| PROTEINACEOUS EXTRACELLULAR MATRIX | 20 | 4.07E-07 |
| REGULATION OF CELL PROLIFERATION | 30 | 5.37E-06 |
| GLYCOPROTEIN | 71 | 3.68E-06 |
| VASCULATURE DEVELOPMENT | 15 | 7.06E-04 |
| EXTRACELLULAR MATRIS PART | 11 | 1.40E-04 |
| RESPONSE TO ORGANIC SUBSTANCE | 25 | 9.32E-04 |
| BLOOD VESSEL DEVELOPMENT | 14 | 3.21E-03 |
| EXTRACELLULAR MATRIX STRUCTURE | 9 | 7.91E-04 |

FIG. 30

| Day | 0 | 6 | 12 | 18 |
|---|---|---|---|---|
| Stage | iPSC | Neuroepithelia | MN precurosors | iMNs |
| Markers | OCT3/4 | SOX1 | OLIG2+ | MNX1 |
|  | NANOG | HOX? | NKX2.2- | CHAT |

Dissociate & re-plate ↓

Day 0 -6
1:1IMDM/F12
1% NEAA
2% 627 (+vitA)
1% N2
1% PSA
0.2 μM LDN193189
10 μM $6431542
3 μM CHIR99021

Day 6 - 12
1:1IMDM/F12
1% NEAA
2% 627 (+vitA)
1% N2
1% PSA
0.1 μM All-trans RA
0.2 μM LDN193189
1 μM Purpmorphamine (or SAG)
10 μM $6431542
3 μM CHIR99021

Day 12 - xx
1:1IMDM/F12
1% NEAA
2% 627 (+vitA)
1% N2
1% PSA
0.1 μMCompound E
2.5 μM DAPT
0.5 μMAll-trans RA
0.1 μM Purpmorphamine (or SAG)
0.1 μMdb-cAMP
200 ng/mlAsoorbic Acid 10 ng/ml GDNF
10 ng/ml 6DNF
0.5 mM VPA

FIG. 31

MICROFLUIDIC MODEL OF THE BLOOD BRAIN BARRIER

CROSS-REFERENCE TO RELATED APPLICATIONS

This application is a Continuation of, and claims priority to, co-pending U.S. patent application Ser. No. 15/768,736, filed Apr. 16, 2018; which claims priority to PCT Application No. PCT/US2016/057724, filed Oct. 19, 2016, now expired; which claims priority to U.S. Provisional Application Ser. No. 62/380,780 filed Aug. 29, 2016; U.S. 62/332,727 filed May 6, 2016; U.S. 62/277,723 filed Jan. 12, 2016; and 62/243,642 filed Oct. 19, 2015; all now expired, the contents of which are incorporated herein in their entirety.

FIELD OF THE INVENTION

The invention relates to culturing brain cells and particularly astrocytes together with endothelial cells in a fluidic device under conditions whereby the cells mimic the structure and function of the blood brain barrier and/or spinal cord. Good viability and function allow for measurements of barrier integrity and physiology, whether by trans-epithelial electrical resistance (TEER), patch clamp or other testing measures.

BACKGROUND OF THE INVENTION

The blood-brain barrier is of major clinical relevance. Not only because dysfunction of the blood-brain barrier leads to degeneration of the neurovascular unit, but also because drugs that are supposed to treat neurological disorders often fail to permeate the blood-brain barrier. Because of its importance in disease and medical treatment, it would be highly advantageous to have a predictive model of the human blood-brain barrier that recapitulates aspects of the cerebral endothelial microenvironment in a controlled way.

SUMMARY OF THE INVENTION

The invention relates to culturing endothelial cells (preferably brain-related endothelial cells), optionally astrocytes, optionally neurons and optionally pericytes in a microfluidic device, such as microfluidic chip (described herein) under conditions whereby the cells mimic one or more structural or functional features (e.g. tight junctions) of the blood brain barrier (BBB) and/or spinal cord. Good viability and function allow for measurements of barrier integrity and physiology, whether by transepithelial electrical resistance (TEER), electrophysiology (including, for example, patch clamp) or other testing measures. Indeed, neuronal cells, such as motor neurons, that are allowed to mature on a microfluidic chip, show a more mature electrophysiology (action potential patterns, for example) indicating a more advanced or accelerated maturation. Thus, in one embodiment, the present invention contemplates a microfluidic culture of iPSC-derived neural progenitor cells or (alternatively) neurons (e.g. a culture in a microfluidic setting, such as in a microchannel and/or microfluidic device) in contact with flowing media. In one embodiment, the iPSC-derived neural progenitors or (alternatively) neurons are cultured alone (without other cell types). In one embodiment, said neurons are iPSC-derived neurons. In one embodiment, said iPSC-derived neurons are motor neurons. In one embodiment, said neurons are cultured in a microchannel or on a membrane of a microfluidic chip. In one embodiment, said microfluidic chip comprises two microchannels separated by a porous membrane having first and second surfaces, wherein said neurons are cultured on said first or second surface. In one embodiment, said culturing is performed for 10, 12, 20, 24, 30, 36 or more days. In one embodiment, said neurons exhibit a more mature electrophysiology as compared to the same neurons cultured in a static culture. Culture of cells in the microfluidic chip, whether alone or in combination with other cells, drives maturation and/or differentiation further than existing systems.

It is not intended that the present invention be limited to only one type of test or measurement to assess the more mature phenotype of neurons and BMECs. In one embodiment, gene expression, Ca2+ flux imaging, immunofluorescent staining, and/or tissue morphology is assessed as evidence of more mature neurons, BMECs and/or astrocytes.

Where neurons, such as motor neurons (or their precursors), are co-cultured (i.e. cultured together) on a microfluidic chip with relevant vascular cells, such as brain microvascular endothelial cells, an even greater effect on differentiation, maturation and/or conditioning is observed. Thus, in one embodiment, the present invention contemplates a microfluidic co-culture of iPSC-derived neural progenitors or (alternatively) neurons with vascular cells, e.g. a microfluidic co-culture of neurons with iPSC-derived vasculature (e.g. said vascular cells are iPSC-derived vascular cells). In one embodiment, said iPSC-derived vascular cells are brain microvascular endothelial cells. In one embodiment, said neurons are iPSC-derived neurons. In one embodiment, said iPSC-derived neurons are motor neurons. In one embodiment, said vascular cells are co-cultured with said neurons in a microchannel or on a membrane of a microfluidic chip. In one embodiment, said microfluidic chip comprises two microchannels separated by a porous membrane having first and second surfaces, wherein said neurons are cultured on said first surface and said vascular cells are cultured on said second surface. In one embodiment, said culturing (e.g. under flow conditions) is performed for 10, 12, 20, 24, 30, 36 or more days. In one embodiment, at least a portion of said neurons and vascular cells are in contact with each other (whether by direct physical contact or indirect cell-to-cell communication). In one embodiment, said neurons and vascular cells are in contact with flowing culture media (e.g. the cells are adhered to a surface and the media flows over the cells at a controlled rate, bringing nutrients and removing waste). In one embodiment, said neurons exhibit a more mature electrophysiology as compared to the same neurons cultured in a static culture.

The microfluidic chip culture increases and accelerates function of iPSC-derived neurons, including motor neurons (MNs). Co-culture with iBMECs recreates known vascular-interaction pathways and further increased maturation in vitro. The fact that cells differentiate and mature more fully on a microfluidic chip indicates that the chip is a better culture tool than more conventional culture systems (e.g. transwell cultures and other static systems), providing a better model of what is going on in vivo (including what is going on in disease states). Thus, in one embodiment, the present invention contemplates a microfluidic device or chip comprising a co-culture of neurons, and more specifically, motor neurons, and more typically, induced motor neurons, with brain microvascular endothelial cells, and more typically, induced brain microvascular endothelial cells. In one embodiment, the present invention contemplates a method of making a co-culture on microfluidic device or chip comprising introducing neurons, and more specifically, motor neurons, and more typically, induced motor neurons, and brain microvascular endothelial cells, and more typically, induced brain microvascular endothelial cells into microfluidic device or chip, and flowing media over said cells. In one embodiment, said culturing (e.g. under flow conditions) is performed for 10, 12, 20, 24, 30, 36 or more days. In one embodiment, the microfluidic chip comprises two microchannels separated (at least in part) by a porous membrane (or other porous member) having first and second surfaces, wherein motor neurons, and more typically, induced motor neurons, are cultured on the first side (e.g. top surface) of the porous membrane (or other porous member) and brain microvascular endothelial cells, and more typically, induced brain microvascular endothelial cells, are cultured on the second surface (e.g. bottom surface) of the porous membrane (or other porous member). Vascular blood flow can be recreated by flowing media in the microchannels.

While not intending to limit the invention to any particular mechanism, it is believed that neuronal progenitor cells and neurons grown in contact with (including in direct contact with) iPSC-derived brain microvascular endothelial cells (BMECs) will mature more fully on a microfluidic chip. There may be a variety of components in the microenvironment that contribute to this result, including but not limited to, autocrine and paracrine signaling, ECM (protein) cues, mass transfer (due to flow), and mechanical forces (including fluid shear). Importantly, the data shows that the improved differentiation, maturation and/or conditioning can be achieved without the addition of exogenous factors.

In one embodiment, the present invention contemplates contact of neurons and brain related vascular cells, and more preferably, direct contact of iMNs and iBMECs on the microfluidic chip to enhance neuronal physiology as measured by electrophysiology and transcriptomics. It has been found that the chip accelerates diMN electrophysiological maturation. Moreover, a highly complex spontaneous activity of the neurons is observed in the chip. Indeed, neural tissue has more mature electrophysiological properties in the chip and in co-culture with BMECs. In some embodiments, more developed currents are observed in the neurons on the chip. In a preferred embodiment, the iMNs and iBMECs are generated from the same person, e.g. the stem cells of the same person. In one embodiment, the iMNs and iBMECs generated from the same patient line, e.g. the same patient stem cells. In one embodiment, the patient has symptoms of a CNS disorder, and more specifically, a neurodegenerative disease. In one embodiment, the neurodegenerative disease is ALS. In one embodiment, the neurodegenerative disease is Parkinson's disease. In one embodiment, the CNS disorder is Alzheimer's disease.

Relevant markers can be detected by fluorescence staining and immunochemistry. In a specific embodiment, cell morphology and movement on (or through) the "BBB-on-chip" is monitored in real-time. Furthermore, in one embodiment, the in vitro model presented by a "BBB-on-chip" can be used to inform drug development or the study of existing agents, by permitting the testing of drug candidates to see if they cross the BBB, harm it, or make it less permissive, potentially under specific coincident conditions or for specific individuals or populations. The BBB-on-chip may also be used for pre-screening and optimization of new treatments potentially as an alternative to animal work, serving as an in vitro proof of principle for clinical studies. Furthermore, the BBB-on-chip model may be used to study disease, including but not limited the role of genetics, environment, cell-to-cell communication, and the role of barrier integrity (or lack thereof) in CNS disease progression. In one embodiment, the present invention contemplates a BBB-on-chip where at least one population of cells is derived from a patient diagnosed with a disorder of the nervous system. In addition, the BBB-on-chip model may be used diagnostically in order to determine, for example, the presence of a medical condition (e.g. a genetic or acquired disease, syndrome or predisposition) or to predict the response of an individual to a potential treatment (e.g. tailoring the dose of medication on the basis of that patient's blood-brain barrier permeability to that medication).

In one embodiment, the present invention contemplates a method of culturing cells, comprising: a) providing a fluidic device comprising a membrane, said membrane comprising a top surface and a bottom surface; b) seeding cells on said bottom surface; and c) culturing said seeded cells under conditions that support the maturation of brain microvascular endothelial cells. In one embodiment, said cells are selected from the group consisting of stem cell-derived cells, cells differentiated from stem cells and primary cells. In one embodiment, said cells differentiated from stem cells are brain microvascular endothelial cells. In one embodiment, said cells differentiated from stem cells are iBMECs. In one embodiment, the method further comprises seeding said cells on said top surface and culturing said top surface seeded cells under conditions that support the maturation of at least one of astrocytes and neurons. In one embodiment, said neurons exhibit a more mature electrophysiology as compared to the same neurons cultured in a static culture. For example, a mature electrophysiology includes negative sodium channel current, positive potassium channel current, and/or action potential spikes of amplitude, duration and frequency similar to neurons in a physiological environment or when compared to static culture neurons, static culture neurons lack one or more of the aforementioned features. In one embodiment, said culturing of said top surface seeded cells further comprises culturing said seeded cells under conditions such that an astrocyte or portion thereof transmigrates said membrane and contacts one or more brain microvascular endothelial cells on said bottom surface. In one embodiment, said cells differentiated from stem cells seeded on said top surface are derived or extracted from EZ spheres, induced neural progenitor cells (iNPCs) or iMNPs. In one embodiment, said stem cells are human induced pluripotent stem cells. In one embodiment, said stem cells are human induced pluripotent stem cells. In one embodiment, prior to step b) at least one of said top or bottom surface are coated with one or more extracellular matrix proteins. In one embodiment, said top surface is coated with laminin. In one embodiment, said bottom surface is coated with a mixture of collagen and fibronectin, and lacks laminin. In one embodiment, said cells seeded on said top surface further comprise pericytes. In one embodiment, said conditions of step c) comprise exposing said seeded cells to a flow of culture media for a period of time (e.g. 4, 7, 10, 12, 20, 24, 30, 36 or more days). In one embodiment, said flow promotes differentiation of said induced motor neuron progenitor (iMNP) cells. In one embodiment, said flow promotes the formation of tight cell-to-cell junctions among said brain microvascular endothelial cells. In one embodiment, the method further comprises detecting said tight cell-to-cell junctions. In one embodiment, said tight cell-to-cell junctions are detected by TEER measurements. In one embodiment, the method further comprises step e) measuring of neuron or astrocyte activity by at least one of intracellular electrophysiology measurements (e.g. patch clamp measurements across the cell membrane), extracellular electrophysiology measurements (e.g field potentials generated by a plurality of cells), imaging using calcium-sensitive dyes or proteins, or imaging using voltage-sensitive dyes or proteins. In one embodiment, said tight cell-to-cell junctions are detected by cell permeability assays. In one embodiment, said brain microvascular endothelial cells express the marker Glut 1. In one embodiment, said culturing of step c) is performed for at least four days. In one embodiment, said culturing of step c) is performed for at least seven days. In one embodiment, said culturing of step c) is performed for 10, 12, 20, 24, 30, 36 or more days. In one embodiment, said fluidic device further comprises at least one inlet port and at least one outlet port, and said culture media enters said inlet port and exits said outlet port. In one embodiment, said membrane comprises a nanopatterned surface which promotes extended and directed neurite growth. The preferred nanopattern is linear valleys and ridges, but alternatives such as circular, curved, or any other desired shape or combination thereof are also contemplated.

In one embodiment, the present invention contemplates a method of culturing cells, comprising: a) providing a microfluidic device comprising a membrane, said membrane comprising a top surface and a bottom surface; b) coating said top surface of said membrane with laminin and said bottom surface with a mixture of collagen and fibronectin, said mixture free of laminin; c) seeding stem-cell derived brain cells on said top surface and brain microvascular endothelial cells on said bottom surface so as to create seeded cells; d) exposing said seeded cells to a flow of culture media for a period of time (e.g. 4, 7, 10, 12, 20, 24, 30, 36 or more days); and e) culturing said seeded cells under conditions such that said brain microvascular endothelial cells on said bottom surface form tight junctions. In one embodiment, said brain microvascular endothelial cells are free of neurons. In one embodiment, said microfluidic device comprises a first fluidic channel in fluidic communication with said top surface of said membrane and a second fluidic channel in fluidic communication with said bottom surface of said membrane, said first and second fluidic channels each comprising a surface that is parallel to said membrane, and each comprising side walls. In one embodiment, said brain microvascular endothelial cells grow on the parallel surface and side walls of the second fluidic channel so as to form a lumen. In one embodiment, said brain microvascular endothelial cells express the marker Glut 1. In one embodiment, said culturing of step e) is performed for at least four days. In one embodiment, said culturing of step e) is performed for at least seven days. In one embodiment, said culturing of step e) is performed for 10, 12, 20, 24, 30, 36 or more days. In one embodiment, said fluidic device further comprises at least one inlet port and at least one outlet port, and said culture media enters said inlet port and exits said outlet port. In one embodiment, said first and second fluidic channels comprise polydimethylsiloxane. In one embodiment, prior to step b) said first and second channels undergo a treatment to promote wetting. In one embodiment, said treatment to promote wetting is selected from the group consisting of plasma treatment, ion treatment, gas-phase deposition, liquid-phase deposition, adsorption, absorption or chemical reaction with one or more agents. In one embodiment, said stem-cell derived brain cells are seeded on wet laminin. In one embodiment, said mixture of collagen and fibronectin is dried prior to step c). In one embodiment, said fluidic device is stored after step b) and before step c). In one embodiment, said fluidic device is stored at a temperature below 25° C. In one embodiment, said fluidic device is stored in a refrigerator. In one embodiment, said induced motor neuron progenitor cells were stored frozen and then thawed prior to step c).

In one embodiment, the present invention contemplates a method of culturing cells, comprising: a) providing a fluidic device comprising a membrane, said membrane comprising a top surface and a bottom surface; b) coating said top surface of said membrane with laminin and said bottom surface with a mixture of collagen and fibronectin, said mixture free of laminin; c) seeding induced motor neuron progenitor cells on said top surface and brain microvascular endothelial cells on said bottom surface so as to create seeded cells; d) exposing said seeded cells to a flow of culture media for a period of time (e.g. 4, 7, 10, 12, 20, 24, 30, 36 or more days); and e) culturing said seeded cells under conditions such that said brain microvascular endothelial cells on said bottom surface form tight junctions. In one embodiment, said induced motor neuron progenitor cells are derived from induced pluripotent stem cells from a human patient diagnosed with a CNS disorder. In one embodiment, said flow promotes the differentiation of said induced motor neuron progenitor cells. In one embodiment, said induced motor neuron progenitor cells are derived from induced pluripotent stem cells from a patient diagnosed with Amyotrophic lateral sclerosis (ALS). In one embodiment, said brain microvascular endothelial cells are derived from induced pluripotent stem cells from a patient diagnosed with MCT8-specific thyroid hormone cell-membrane transporter deficiency. In one embodiment, said induced motor neuron progenitor cells were stored frozen and then thawed prior to step c).

In one embodiment, the present invention contemplates a fluidic device comprising a membrane, said membrane comprising a top surface and a bottom surface, said top surface comprising at least one stem-cell derived brain cell and said bottom surface comprising brain microvascular endothelial cells. In one embodiment, said at least one stem-cell derived brain cell is selected from the group consisting of induced motor neuron progenitor cells, EZ Sphere-derived cells and iNPCs. In one embodiment, the device further comprises a first fluidic channel in fluidic communication with said top surface of said membrane and a second fluidic channel in fluidic communication with said bottom surface of said membrane, said first and second fluidic channels each comprising a surface that is parallel to said membrane, and each comprising side walls. In one embodiment, said brain microvascular endothelial cells are present on the parallel surface and side walls of the second fluidic channel so as to constitute a lumen.

In one embodiment, the present invention contemplates a system, comprising a) a fluidic device comprising a membrane, said membrane comprising a top surface and a bottom surface, said top surface comprising at least one stem-cell derived brain cell and said bottom surface comprising brain microvascular endothelial cells, said microfluidic device further comprising a first fluidic channel in fluidic communication with said top surface of said membrane and a second fluidic channel in fluidic communication with said bottom surface of said membrane, b) a fluid source in fluidic communication with said first and second fluidic channels, whereby said cells are exposed to fluid at a flow rate for a period of time (e.g. 4, 7, 10, 12, 20, 24, 30, 36 or more days). In one embodiment, said at least one stem-cell derived brain cell is selected from the group consisting of induced motor neuron progenitor cells, EZ Sphere-derive cells and iNPCs.

Traditional in vitro systems used in human stem cell-based modeling of neurodegenerative diseases such as Amyotrophic Lateral Sclerosis (ALS) possess inherent limitations for biological and pathological relevance. Studies have revealed that stem cell-derived neural tissue is unable to mature fully in vitro. This fetal-like immature phenotype presents a challenge when studying genetic contribution to adult-onset pathogenesis in vitro. Here, we hypothesize that iPSC-derived motor neurons (MNs) can better mature through enhanced endogenous media conditioning and the addition of developmentally relevant, non-neuronal cell types in co-culture. To address this, such motor neurons are matured in a microfluidic device and the functional effects of micro-media volumes are assessed on the neuronal maturation of induced pluripotent stem cell (iPSC)-derived MNs originating from non-disease control and ALS patients.

Without being bound to theory, the influence of non-neuronal cell types (e.g. astrocytes, etc.) on neuron maturation can be enhanced by recirculating one or more of the fluids in the microfluidic device. For example, medium flowing through a neuronal compartment can be recirculated by fluidically connecting the output of that channel back into its input, optionally by flowing through a recirculation pump. Many methods of recirculation are known in the art, including for example, discrete recirculation wherein output fluids are introduced back into an input reservoir using a pipetting or liquid-handling operation or a specialized valving system.

In some embodiments, the effect of non-neuronal cell types on neuron maturation can be obtained by providing the microfluidic device with fluidics that have been conditioned by culture with one or more non-neuronal cell types. For example, medium cultured with BMECs and/or astrocytes can be used as input or combined, mixed and/or interleaved with one or more input fluids of the BBB-chip. The use of conditioned fluids may be used in addition to or instead of the including of non-neuronal cell types within the chip.

The data (e.g. maturation data (PCA), electrophysiology data and calcium imaging data showing more activity) show that iPSC-derived motor neurons (MNs) can better mature (e.g. develop to a more mature state) through enhanced endogenous media conditioning and/or the addition of developmentally relevant, neuronal or non-neuronal cell types in co-culture. Developmentally relevant cell types include brain microvascular endothelial cells and astrocytes that emerge at the time point at which current standard culture methods are known to be stagnated. The evidence also supports improved maturation of the astrocytes and BMECs. As described herein, astrocytes were observed to send out of processes to contact the endothelial cells. As described herein, improved and sustained barrier function indicates maturation of the BMECs.

Without intending that the present invention be bound by theory as to the mechanism by which the cells cultured in a microfluidic setting exhibit a more mature phenotype, it is believed that it is the improved microenvironment that the Chip provides that is responsible for the effect. The relevant elements of the Chip microenvironment include (but are not limited to): a) improved communication between cells of the same type, e.g. because of a lower volume of dilution/distribution within the chip (in one embodiment, enhanced endogenous media conditioning is employed); b) communication between the different cell type (e.g. neuron/astrocyte communication, astrocyte/endo communication (in one embodiment, the present invention contemplates developmentally relevant, neuronal or non-neuronal cell types in co-culture); c) mass transport properties related to the fluidic environment (e.g. flow affects autocrine signaling, paracrine signaling, washing out waste products, providing nutrients, etc.); d) access to both the apical and basal sides of the BMECs and, potentially, the biochemical independence/isolation of those two sides; e) mechanical forces, especially shear forces in this case (e.g. shear force is known to affect endothelial cell phenotype); f) enhanced replenishment of media factors related to differentiation (e.g. as opposed to static culture, where the concentration of the factors may deplete through culture/incubation); g) improved ECM signaling, both the ability to coat with multiple ECMs in different regions (e.g. one ECM for the neuronal compartment and a different one for the endothelial cells) and the ability of the cells in the system to remodel the ECM and its composition (e.g. the BMECs may be laying down ECM that could influence the astrocytes).

Without being bound by theory, it is believed that the Chip microenvironment promotes differentiation for largely the same reasons that it helps maturation (see above). In the microfluidic setting, it is believed that the cells derived from stem cells reach the intended fate more completely, more accurately and/or faster.

Without being bound by theory, it is believed that the microfluidic setting promotes improved longevity of the cells and/or improved maintenance of at least one function of the BBB, neurons or neurovascular junction. We observe such improved longevity and maintenance of function, for example, in the survival of the neurons and maintenance of their firing, and in the maintenance of the BMEC barrier function.

While not intending to be limited to any specific mechanism, the data indicates that culturing the cells under flow (preferably continuous flow) conditions (instead of a static culture) increased the number of iMNs and BMECs per chip when measured over time, e.g. 10, 12, 20, 24, 30 and 36 days or more. In a preferred embodiment, MNs are co-cultured with iPSC-derived BMECs under flow (preferably continuous flow) conditions (e.g. MNs on the top surface of the membrane and BMECs on the bottom surface). Such cultures became dense, thick tissue indicating a three dimensional structure. At the membrane, both cell types could be observed interacting. Just below the membrane both cell types interacted and diMNs were observed to infiltrate in large clusters into the bottom channel. BMECs persisted on the bottom channel and continued to form tight junctions.

Definitions

Some abbreviations are used herein. For example, "MN" refers to motor neurons. The letter "i" indicates "induced." Thus, "iMN" indicates induced motor neurons, i.e. motor neurons that were induced or generated from other cells, e.g. stem cells. "diMN" indicates direct induced motor neurons. "iMNP" indicates induced motor neuron progenitor cells, which are not fully differentiated into mature neurons.

In one embodiment, the starting material for generating at least one cellular component for the BBB generated on a microfluidic device (or simply "BBB-on-chip") comprises stem cells (e.g. see the protocol in Example 1, below). In particular embodiments, these stem cells may include, for example, induced pluripotent stem cells (iPS cells) or embryonic stem cells. In one embodiment, progenitor cells (derived from stem cells) related to neural or vascular lineages or cells directly reprogrammed into astrocytes, neurons, pericytes, endothelial cells, neural lineage progenitors or endothelial lineage progenitors are employed/seeded on the chip. It is important to note that not all cell types involved in the BBB-on-chip must be generated from stem cells. For example, the BBB-on-chip may employ primary brain microvascular endothelial cells (BMECs). Techniques are known in the art to reprogram, expand and characterize human iPS cells from human skin or blood tissues of healthy subjects and diseased patients. For example, a non-integrating system based on the oriP/EBNA1 (Epstein-Barr nuclear antigen-1) episomal plasmid vector system can be used to avoid potential deleterious effects of random insertion of proviral sequences into the genome. See Okita K, et al., "A more efficient method to generate integration-free human iPS cells," Nat Methods. 2011 May; 8:409. It is preferred that the iPSC lines so generated express the pluripotency markers (SSEA4, TRA-1-81, OCT3/4, SOX2) along with a normal karyotype. In the present invention, iPS cells are used to generate components of the BBB-on-chip, e.g. BMECs, neurons, etc. While in many cases, the iPS cells are from normal subjects, it is also contemplated that the iPS cells can be derived from patients exhibiting symptoms of disease. In one embodiment, the BBB-on-chip is populated with cells derived from iPS cells from a patient diagnosed with a disorder of the nervous system, including but not limited to iPSC-derived motor neurons from Amyotrophic lateral sclerosis (ALS) patients. See D. Sareen et al., "Targeting RNA foci in iPSC-derived motor neurons from ALS patients with C9ORF72 repeat expansion" Sci Transl Med. 2013 Oct. 23; 5(208): 208ra149.

In one embodiment, the present invention contemplates differentiating "stem-cell derived brain cells" on the chip, i.e. in a microfluidic environment. The term "stem-cell derived brain cells" refers to cells derived from stem cells that fall on a spectrum of differentiation. For example, in one embodiment, induced motor neuron progenitor cells (including but not limited to, iPSC-derived forebrain neural progenitors) are derived from induced pluripotent stem cells, but they are not fully differentiated. In one embodiment, induced motor neuron progenitor cells are differentiated on-chip to generate motor neurons, and ultimately mature motor neurons. Thus, in one embodiment, the present invention contemplates a method of culturing cells, comprising: a) providing a microfluidic device (optionally comprising a membrane, said membrane comprising a top surface and a bottom surface); b) seeding induced motor neuron progenitor cells (optionally on said top surface and optionally brain microvascular endothelial cells on said bottom surface so as to create seeded cells); c) exposing said seeded cells to a flow of culture media for a period of time (days to weeks to months) under conditions such that said at least a portion of said progenitor cells differentiate into motor neurons (and preferably wherein said motor neurons display a mature phenotype based on testing described herein or staining). In one embodiment, the method (optionally) further comprises e) culturing said seeded cells under conditions such that said brain microvascular endothelial cells on said bottom surface form tight junctions.

As another example, in one embodiment, induced brain microvascular endothelial progenitor cells are derived from induced pluripotent stem cells, but they are not fully differentiated. In one embodiment, induced brain microvascular endothelial progenitor cells are differentiated on-chip to generate BMECs, and ultimately mature BMECs. Thus, in one embodiment, the present invention contemplates a method of culturing cells, comprising: a) providing a microfluidic device (optionally comprising a membrane, said membrane comprising a top surface and a bottom surface); b) seeding induced brain microvascular endothelial progenitor cells (on said top surface or on said bottom surface so as to create seeded cells); c) exposing said seeded cells to a flow of culture media for a period of time (days to weeks to months) under conditions such that said at least a portion of said progenitor cells differentiate into brain microvascular endothelial cells (and preferably wherein said BMECs display a mature phenotype based on testing described herein or staining).

It is not intended that the present invention be limited by the nature of the "microfluidic device" or "chip." However, preferred microfluidic devices and chips are described in U.S. Pat. No. 8,647,861, hereby incorporated by reference, and they are microfluidic "organ-on-chip" devices comprising living cells in microchannels, e.g. cells on membranes in microchannels exposed to culture fluid at a flow rate. It is important to note that the features enabling the actuation of strain or mechanical forces on the cells within the "organ-on-chip" device are optional with regards to the "BBB-on-chip" and may be omitted. Flow is important and stands in contrast to static 2D culture. Using a flow in the microchannel(s) allows for the perfusion of cell culture medium throughout the cell culture during in vitro studies and as such offer a more in vivo-like physical environment. In simple terms, an inlet port allows injection of cell culture medium, blood, blood component or mixture thereof into a cell-laden microfluidic channel or chamber, thus delivering nutrients and oxygen to cells. An outlet port then permits the exit of remaining liquid as well as harmful metabolic by-products. While continuous flow is preferable due to its application of controlled shear forces, either of the device's fluidic paths could also be cultured under "stop flow" conditions, where the flow is engaged intermittently, interspersed by static culture.

Microfluidic devices are conveniently made of polydimethylsiloxane (PDMS), polyurethane, polycarbonate, polystyrene, polymethyl methacrylate, polyimide, styrene-ethylene-butylene-styrene (SEBS), polypropylene, or any combinations thereof. The present invention contemplates treatment of such substances to promote cell adhesion, selection or differentiation or fluid wetting such as treatments selected from the group consisting of plasma treatment, ion treatment, gas-phase deposition, liquid-phase deposition, adsorption, absorption or chemical reaction with one or more agents.

Additionally, the term "microfluidic" as used herein relates to components where moving fluid is constrained in or directed through one or more channels wherein one or more dimensions are 10 mm or smaller (microscale). Microfluidic channels may be larger than microscale in one or more directions, though the channel(s) may be on the microscale in at least one direction. In some instances the geometry of a microfluidic channel may be configured to control the fluid flow rate through the channel. Microfluidic channels can be formed of various geometries to facilitate a wide range of flow rates through the channels. However, it is important to note that while the present disclosure makes frequent reference to "microfluidic" devices, much of what is taught applies similarly or equally to larger fluidic devices. Larger devices may be especially relevant if the "BBB-on-chip" is intended for therapeutic application. Examples of applications that may make advantage of larger fluidic devices include the use of the device for the generation of highly differentiated cells (e.g. the device can used to drive cell differentiation and/or maturation, whereupon the cells are extracted for downstream use, which may include implantation, use in an extracorporeal device, or research use), or use of the device for implantation or extracorporeal use, for example, as an artificial blood-brain barrier or a dialysis-like technology.

As used herein, the phrases "connected to," "coupled to," and "in communication with" refer to any form of interaction between two or more entities, including mechanical, electrical, magnetic, electromagnetic, fluidic, and thermal interaction. For example, in one embodiment, first and second channels in a microfluidic device are in fluidic communication with a fluid reservoir. Two components may be coupled to each other even though they are not in direct contact with each other. For example, two components may be coupled to each other through an intermediate component (e.g. tubing or other conduit).

The surfaces of the microchannels and/or the membrane can be coated with cell adhesive, selective or promotive molecules to support the attachment of cells and promote their organization into tissues. Where a membrane is used, tissues can form on either the upper surface of the membrane, the lower surface of the membrane, any of the surfaces of the channels or cavities present on either side of the membrane or any combination thereof. In one embodiment, different cells are living on the upper and lower surfaces, thereby creating one or more tissue-tissue interfaces separated by the membrane. The membrane may be porous, flexible, elastic, or a combination thereof with pores large enough to only permit exchange of gases and/or small chemicals, or large enough to permit migration and transchannel passage of large proteins, as well as whole living cells and/or portions thereof (e.g. the endfoot of an astrocyte). Depending on the size-scale of the pores and manufacturing preferences, the pores may be defined, for example, using lithography, molding, laser-drilling or track-etching, intrinsic to a selected material (for example, polyacrylamide gel, collagen gel, paper, cellulose) or engineered into the material (e.g. by generating an open-cell polymer or matrix).

It is not intended that the present invention be limited to particular "flow rates" or means for generating flow rates. In one embodiment, a flow rate of between 5 and 200 uL/hr, and more preferably between 20-100 uL/hr, and still more preferably between 10 and 60 uL/hr, and still more preferably between 20-50 uL/hr, is contemplated. In one embodiment, pressure is applied through the lid (11) and the lid seals against the reservoir(s) (see FIG. 22B). For example, when one applies 1 kPa, this nominal pressure results, in one embodiment, in a flow rate of approximately 30-40 uL/hr. When one applies a pressure of between 0.5 kPa, this nominal pressure results, in one embodiment, in a flow rate of between 15 uL/hr and 30 uL/hr.

There are many ways to evaluate the integrity and physiology of an in vitro system that mimics the blood brain barrier. Two of the most common methods are Transepithelial Electric Resistance (TEER) and Lucifer Yellow (LY) rejection. Importantly, manipulations must be performed using aseptic techniques in order for the cells to remain in culture without contamination. TEER measures the resistance to pass current across one or more cell layers on a membrane. The measurement may be affected by the pore size and density of the membrane, but it aims to ascertain cell and/or tissue properties. The TEER value is considered a good measure of the integrity of the cell monolayer.

Lucifer Yellow (LY) travels across cell monolayers only through passive paracellular diffusion (through spaces between cells) and has low permeability. Therefore it is considerably impeded in passing across cell monolayers with tight junctions. Permeability (Papp) for LY of ≤ to 12 nm/s has been reported to be indicative of well-established monolayers.

Description of the Tables

Table 1 shows various conditions (especially related to surface treatment and cell seeding) tested for seeding neural cells (EZ spheres and iMNPs) and endothelial cells (iBMECs), which may optionally originate from frozen stocks of cells. Ebert et al., "EZ spheres: A stable and expandable culture system for the generation of pre-rosette multipotent stem cells from human ESCs and iPSCs" Stem Cell Res. (2013) 10(3):417-427; Lippmann et al., "Human Blood-Brain Barrier Endothelial Cells Derived From Pluripotent Stem Cells" Nat. Biotechnol. (2012) 30(8):783-791; and Sareen et al., "Human neural progenitor cells generated from induced pluripotent stem cells can survive, migrate, and integrate in the rodent spinal cord" J. Comp. Neurol. (2014) 522(12): 2707-2728. The best results for iBMECs were achieved with a mixture of collagen and fibronectin (4:1 ratio). The best results for iMNPs were achieved with laminin. A variety of surface treatments and coating materials are known in the art (e.g. from traditional plate-based tissue culture or microfluidic tissue culture), for example, plasma treatment, corona treatment, aminopropyl triethoxysilane (APTES), collagen (including type I and type IV), fibronectin, laminin, gelatin, Matrigel, and mixtures thereof. The BBB-on-chip can make use of stem cells as the origin for either one or more of its neural components (which includes at least astrocytes or related cells), one or more of its endothelial components, or both. In particular embodiments, these stem cells may include induced pluripotent stem cells (iPS cells) or embryonic stem cells. In one embodiment, progenitor cells related to neural or vascular lineages or cells directly reprogrammed into astrocytes, endothelial cells, neural lineage progenitors or endothelial lineage progenitors are contemplated for seeding on the chip. The cells may be differentiated into respective cells type before they are deposited in the BBB-on-chip, differentiated within the BBB-on-chip, or partially differentiated before deposition in the BBB-on-chip with further differentiated within the BBB-on-chip. The BBB-on-chip may promote the differentiation and/or maturation of any of the involved cell types. This may be accomplished, for example, by the microenvironment generated by or present within the BBB-on-chip (e.g. cell-cell signaling, protein coating, fluid flow), by the use of differentiation protocols designed for fluidic culture (e.g. facilitated by flow in microfluidic channels), or combination thereof. Selecting the surface coating is important in order to promote initial cell attachment and viability. Moreover, surface coating may be helpful and sometime necessary in order to select for specific cell populations (e.g. when seeding a mixed population as is commonplace in stem-cell derived cells) and/or to provide differentiation or maturation signals to the cells. The effects or success of surface coatings can vary depending on the underlying substrate. Accordingly, the results illustrated in Table 1 correspond to a PDMS substrate.

Table 2 shows various conditions tested for seeding neural (EZ spheres, iNPCs and iMNPs) and endothelial cells (iBMECs) on the apical and basal sides of a microfluidic chip. This chip comprised a porous membrane separating a top fluidic channels and bottom fluidic channel (the chip was modeled after an embodiment disclosed in U.S. Pat. No. 8,647,861 without the optional vacuum operating channels). In typical embodiments of the present disclosure that comprise a porous membrane, any brain cells (e.g. astrocytes, neurons) are disposed within the said top fluidic channel, and endothelial cells (e.g. iBMECs, primary BMECs, HUVECs) are disposed within the said bottom fluidic channel. In other embodiments, however, endothelial cells are disposed within the top fluidic channel and brains cells are disposed within the bottom fluidic channel, while in yet other embodiments, both endothelial and brain cells are disposed within the same fluidic channel (top, bottom or both).

Tables 3 and 4 show various conditions tested for seeding fresh neural cells (iMNPs) and fresh endothelial cells (iBMECs), where the particular conditions are associated by microfluidic chip number, allowing for a correlation of good tight junctions with the seeding conditions. Chips can be seeded with a variety of seeding density, with the optimal density determined by factors including (but not limited) to cell type, stage of differentiation, surface coating, substrate material, media composition, whether the cells proliferate after seeding, seeding incubation time, channel dimensions, etc. Seeding densities for neural cells including EZ spheres, iNPCs, and iMNPs in the device illustrated in Table 2 can range, for example, between $1\times10^3$ cells/mL and $1\times10^8$ cells/mL or between $1\times10^4$ cells/mL and $5\times10^8$ cells/mL. Seeding densities for endothelial cells including iBMECs in the device illustrated in Table 2 can range, for example, between $2.5\times10^3$ cells/mL and $1\times10^8$ cells/mL or between $2\times10^4$ cells/mL and $5\times10^8$ cells/mL.

DESCRIPTION OF THE DRAWINGS

FIG. 4C is a vertical 2D projection of a 3D confocal stack of images slices, which allows for visualization of the neurons and endothelial cells together, even though they are not in the same plane on the microfluidic device.

FIGS. 9A and C show the results for Chip 664 where BMECs (on collagen/fibronectin) and iMPs (on wet laminin) were co-cultured. FIGS. 9B and 9D show the results for Chip 663 where iMPs (on laminin) were cultured alone.

FIG. 12A shows the results/readout from transepithelial electrical resistance (TEER) measurements on the microfluidic chip under flow, static, and control conditions. Clearly, flow is important for optimum results. FIG. 12B show TEER measurements on transwells. TEER is a typical measure of in vitro BBB models and is used both for evaluating the model as well as an experimental readout (e.g. after subjecting the BBB model to an experimental condition). Some aspects of the present invention include measuring the TEER of one or more BBB-on-chips. This can be done, for example, to evaluate BBB-on-chip development, maturation or quality, as a readout for experiments involve an introduced agent, as a readout for experiments involving specific cells or cell types (e.g. patient specific, a disease population, or treated to simulate a disease or condition), etc. It is known in the art how to integrate electrodes suitable for TEER measurement into microfluidic devices. Douville et al., "Fabrication of Two-Layered Channel System with Embedded Electrodes to Measure Resistance Across Epithelial and Endothelial Barriers" Anal Chem. 2010 Mar. 15; 82(6): 2505-2511.

FIG. 13A and FIG. 13B show how TEER measurements were made in one embodiment. FIG. 13A is an enlarged schematic view showing how electrodes on the chip were connected, along with pipette tips engaging the chip; FIG. 13B shows the same connected chip to the right of a Epithelial Voltohmmeter.

FIG. 15 shows permeability results for (and the structure of) fluorescein sodium. Some aspects of the present invention include ascertaining permeability for various additional agents (e.g. drugs, chemicals, hormones, blood components, biomarkers). Such methods can allow qualitative or quantitative estimation of the permeability of the in vitro blood-brain barrier to the one or more agents. Furthermore, according to some aspects of the present invention, the permeability of one agent is measured in response to a second agent, treatment or experimental condition (for example, measuring the effect of a medication on the blood-brain barrier permeability of another medication).

FIG. 19A-D show the results of calcium flux imaging in the neural channel. The photograph (FIG. 19A, top left) is a single fluorescent image from a movie of such images. The colored circles indicate the positions that correspond to the time traces in the 3 graphs. The traces (FIGS. 19B and 19C) show that it is possible to observe neuronal function in the microfluidic chips in real-time. The addition of tetrodotoxin (TTX), which is a potent blocker of voltage-gated calcium channels, ablates this activity (FIG. 19D, bottom right). Calcium imaging or imaging using voltage-sensitive dyes or proteins offer similar advantages to electrophysiological readouts but offers the advantage that no electrodes are necessary. Accordingly, some aspects of the present invention include methods of measuring the BBB-on-chip by imaging in the presence of calcium or voltage-sensitive dyes or proteins, to allow the potential recording and optional manipulation of neuronal or astrocyte excitations. These measurements can be used, for example, to provide an indication of neuronal maturation or as a readout of neuron health. In turn, neuronal maturation or health can be used as indicators of BBB-on-chip quality (for example, before starting an experiment) or as an experimental endpoint indicating, for example, that an agent as crossed the BBB, a disease condition has emerged, the BBB has been modified or compromised, or conversely, that the BBB or neural function or health have improved.

FIG. 23B shows an exploded view of the device of FIG. 23A, showing a bottom piece (97) having channels (98) in a parallel configuration, and a top piece (99) with a plurality of ports (2), with a tissue-tissue interface simulation region comprising a membrane (101) between the top (99) and bottom (97) pieces, where (in one embodiment) cell behavior and/or passage of gases, chemicals, molecules, particulates and cells are monitored. In an embodiment, an inlet fluid port and an outlet fluid port are in communication with the first central microchannel such that fluid can dynamically travel from the inlet fluid port to the outlet fluid port via the first central microchannel, independently of the second central microchannel. It is also contemplated that the fluid passing between the inlet and outlet fluid ports may be shared between the central microchannels. In either embodiment, characteristics of the fluid flow, such as flow rate and the like, passing through the first central microchannel is controllable independently of fluid flow characteristics through the second central microchannel and vice versa.

FIG. 24 is a print out of electrophysiological data from neurons cultured in a microfluidic device or chip, showing highly complex spontaneous activity in a chip.

FIG. 25A-B shows print outs of electrophysiological data from neurons cultured alone (FIG. 25A, top panel) and co-cultured with BMECs (FIG. 25B, bottom panel) in a microfluidic device or chip, showing that neural tissue have more mature electrophysiological properties in the chip, and in co-culture with BMECs.

FIG. 30 shows the detailed results of expression of each gene (row) in each of the 5 conditions (columns), showing the names of various neural development genes (PC1), chip induced genes (PC2) and vascular interaction genes (PC3). The colored bars on the right in FIG. 30 represent the expression of each gene (row) in each of the 5 conditions (columns). Column order is MN Only, BMEC/MN, 96-well control, 96 well ECCM, MN progenitor. Red=high and blue=low. These vascular gene pathways have not been shown to be induced in any other culture system and may be inducing the observed increase in maturity and activity.

FIG. 31 shows the various factors used in the protocol for the generation of motor neurons are provided (using iPSCs as the starting material).

DESCRIPTION OF THE INVENTION

Figure 1:
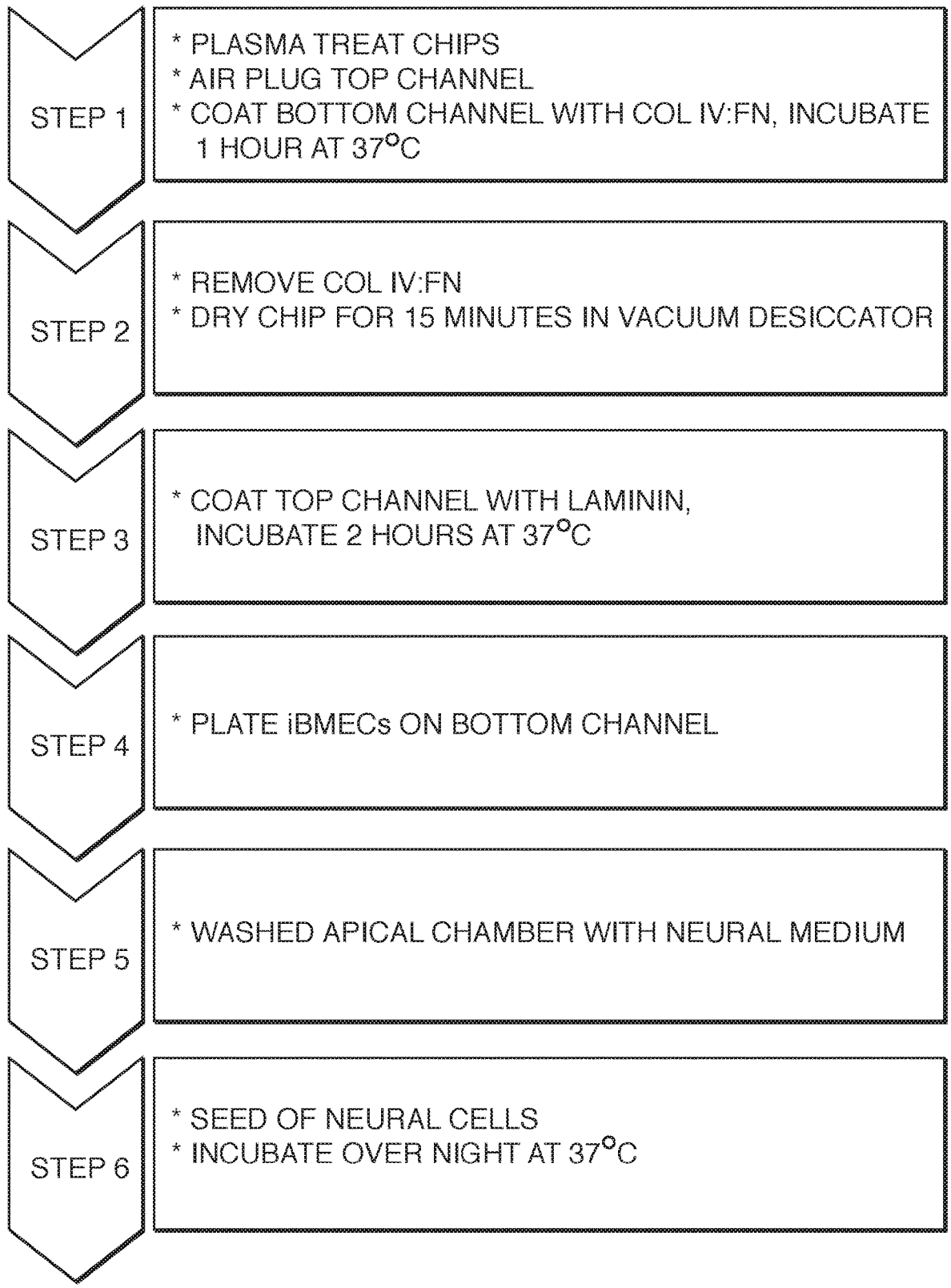
FIG. 1 shows a schematic of one embodiment of a workflow for preparing and seeding a microfluidic chip comprising six steps. This embodiment addresses the different surface coating needs/preferences apparent for iBMECs and iMNPs based on experiments such as those illustrated in Tables 1 and 2. In particular, the workflow aims to provide, in one embodiment, different surface coatings for the top fluidic channel and bottom fluidic channel of the device.

The invention relates to culturing endothelial cells (preferably brain-related endothelial cells) and optionally astrocytes, optionally neurons, and optionally pericytes in a fluidic device under conditions whereby the cells mimic one or more structural or functional features (e.g. tight junctions) of the blood brain barrier and/or the spinal cord. Culture of these cells in a microfluidic device, such as a microfluidic chip with flow as herein described, whether alone or in combination with other cells, drives maturation and/or differentiation further than existing systems. For example, a mature electrophysiology of the neurons includes negative sodium channel current, positive potassium channel current, and/or action potential spikes of amplitude, duration and frequency similar to neurons in a physiological environment or when compared to static culture neurons, static culture neurons lack one or more of the aforementioned features. The evidence also supports improved maturation of the astrocytes and BMECs. As described herein, astrocytes were observed to send out of processes to contact the endothelial cells. As described herein, improved and sustained barrier function indicates maturation of the BMECs. Good viability and function allow for measurements of barrier integrity and physiology, whether by TEER, permeability assays, patch clamp (or other electrophysiological methods), calcium or voltage imaging, or other testing measures. Observed characteristics of the in vitro "BBB-on-chip" of the present invention include: (1) tight junctions between endothelial cells (which creates selective permeability to substances); (2) optional cell-to-cell communication exemplified by contact of the endothelial cells with astrocytes (e.g. endfoot contact by partial transmigration of the membrane separating these cells); (3) optional extended neurite projections, (4) optional fluid flow that influences cell differentiation and tight junction formation; and (5) high electrical resistance representing the maturity and integrity of the BBB components. With respect to neurite projections, in one embodiment, the present invention contemplates seeding on nanopatterned surfaces which promote extended and direct (e.g. along a relatively linear path) neurite growth. The preferred nanopattern is linear valleys and ridges, but alternatives such as circular, curved, or any other desired shape or combination thereof are also contemplated. With respect to endothelial cells, in one embodiment, the present invention contemplates BMECs which form a lumen on the chip (for example, completely lining a flow channel, at least for a portion of its length). Among other advantage (e.g. endothelial layer stability) this potentially enables the use of the device with blood or blood components. With respect to selective permeability, the present invention contemplates, in one embodiment, introducing substances in a channel under the BMECs such that at least one substance passes through the BMEC barrier (e.g. BMEC cells on the bottom side of the membrane) and into a channel above the membrane, and detecting said at least one substance (e.g. with antibodies, mass spec, etc.).

Although there is a strong need for a model of the human blood-brain barrier, it is also desirable to develop models of blood-brain barriers of other organisms (not limited to animals). Of particular interest are models of, for example, mouse, rat, dog, and monkey, as those are typically used in drug development. Accordingly, the BBB-on-chip can make advantage of not only human-derived cells but also cells from other organisms. Moreover, although it is preferable that all cell types used originate from the same species (for example, in order to ensure that cell-cell communication is effective), it may be desirable at time to mix species (for example, if a desired cell type is scarce or possess technical challenges).

DESCRIPTION OF PREFERRED EMBODIMENTS

In one embodiment, the present invention contemplates a BBB-on-chip where at least one population of cells is derived from a patient diagnosed with a disorder of the nervous system. While it is not intended that the present invention be limited to a particular CNS disorder, in one embodiment, the disorder is ALS. Amyotrophic lateral sclerosis (ALS) is a severe neurodegenerative condition characterized by loss of motor neurons in the brain and spinal cord. In one embodiment, the present invention contemplates generating induced pluripotent stem cells (iPSCs) from patients with ALS and differentiating them into motor neurons progenitors for seeding on a microfluidic device. There are currently no effective treatments for ALS. In one embodiment, the present invention contemplates the BBB-on-chip as a model system for testing drugs so as to predict success in subsequent clinical trials.

In another embodiment, the CNS disorder is Parkinson's disease (PD). PD is a neurodegenerative disorder primarily characterized by a loss of dopamine neurons, but which also leads to many other pathological changes.

In yet another embodiment, the CNS disorder is Alzheimer's disease. Alzheimer's is a type of dementia that causes problems with memory, thinking and behavior. Symptoms usually develop slowly and get worse over time, becoming severe enough to interfere with daily tasks.

It is contemplated that iPSC technology can be used together with microfluidic chips to mimic patient-specific phenotypes in disease states. For example, in another embodiment, cells derived from patients diagnosed with MCT8-specific thyroid hormone cell-membrane transporter deficiency are contemplated for use in microfluidic devices as at least one of the cellular components of the "BBB-on-chip." This disease is characterized by severe cognitive deficiency, infantile hypotonia, diminished muscle mass and generalized muscle weakness, progressive spastic quadriplegia, joint contractures, and dystonic and/or athetoid movement with characteristic paroxysms or kinesigenic dyskinesias. Seizures occur in about 25% of cases. Patients exhibit pathognomonic thyroid test results including high serum 3,3',5-triiodothyronine ($T_3$) concentration and low serum 3,3',5'-triiodothyronine (reverse $T_3$ or $rT_3$) concentration. Serum tetraiodothyronine (thyroxine or $T_4$) concentration is often reduced, but may be within the low normal range; serum TSH concentrations are normal or slightly elevated. SLC16A2 (also known as MCT8) is the only gene in which mutations are known to cause this disorder.

EXPERIMENTAL

Example 1

Cells are prepared either directly from cultured iPSCs or from frozen lots of pre-differentiated cells. Cells are thawed (or dissociated fresh) and seeded into the chip at day 8-9 (in the case of BMECs differentiation) and at various points in neural differentiation. In the case of MNs, for example, cells are seeded at day 12 of differentiation either from freshly differentiated cultures or directly from a thawed vial. iPSC-derived forebrain neural progenitor cultures (dubbed EZs) were cultured in chip either dissociated or as neural spheres that attached and extended in 3 dimensions (See FIG. 3A-B apical). The various factors used in the protocol (see FIG. 31) for the generation of motor neurons are provided (using iPSCs as the starting material).

Example 2

Figure 32:
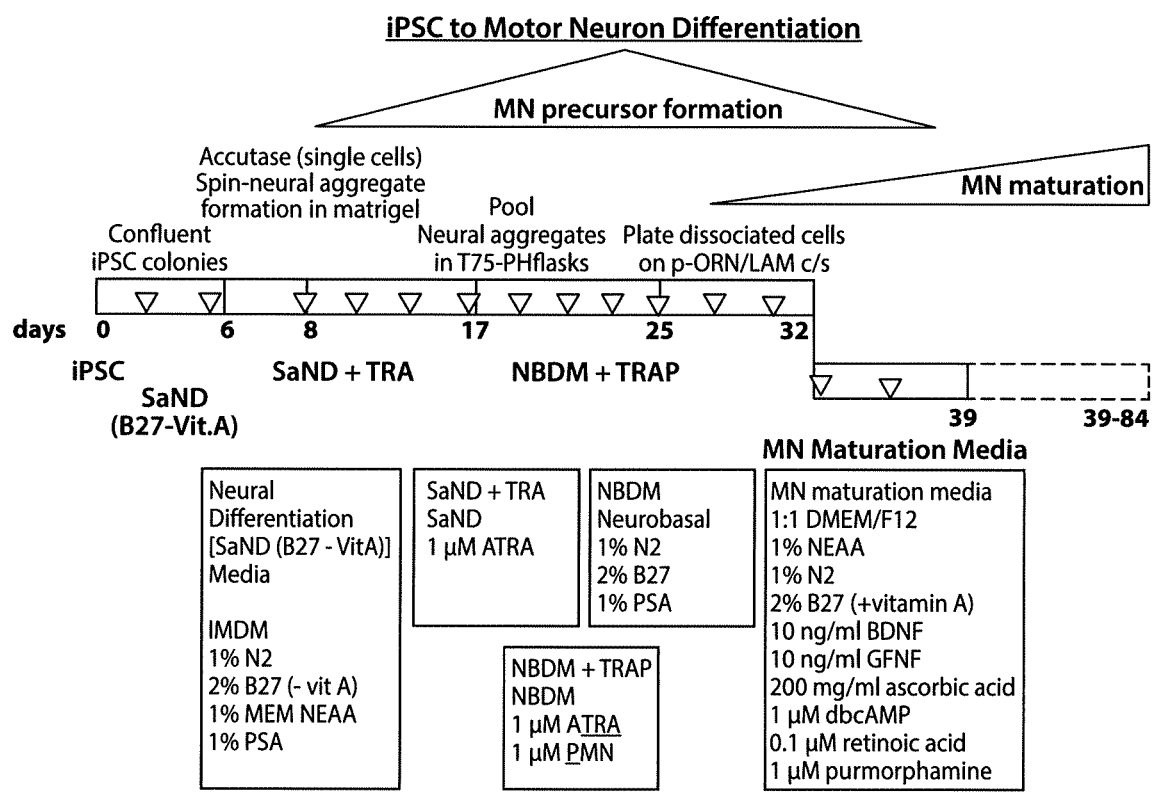
FIG. 32 shows the various factors used in the protocol for the generation of motor neurons are provided (using iPSCs as the starting material).

In this example, another protocol for the generation of motor neurons is provided using iPSCs as the starting material:

The various factors used in the protocol (see FIG. 32) for the generation of motor neurons are provided (using iPSCs as the starting material).

Example 3

This example explores various conditions tested for seeding neural (EZ spheres and iMNPs) and endothelial cells (iBMECs) from frozen stocks of cells on surfaces treated with different extracellular matrices (ECMs). The best results for iBMECs were achieved with a mixture of collagen and fibronectin (4:1 ratio) using a seeding concentration of $5\times10^6$ cells/ml (Table 1). Given these results, seeding was attempted on microfluidic devices, i.e. chips. Table 2 shows various conditions tested for seeding neural (EZ spheres, iNPCs and iMNPs) and endothelial cells (iBMECs) on the apical and basal sides of a microfluidic chip using frozen stocks of cells.

Figure 2:
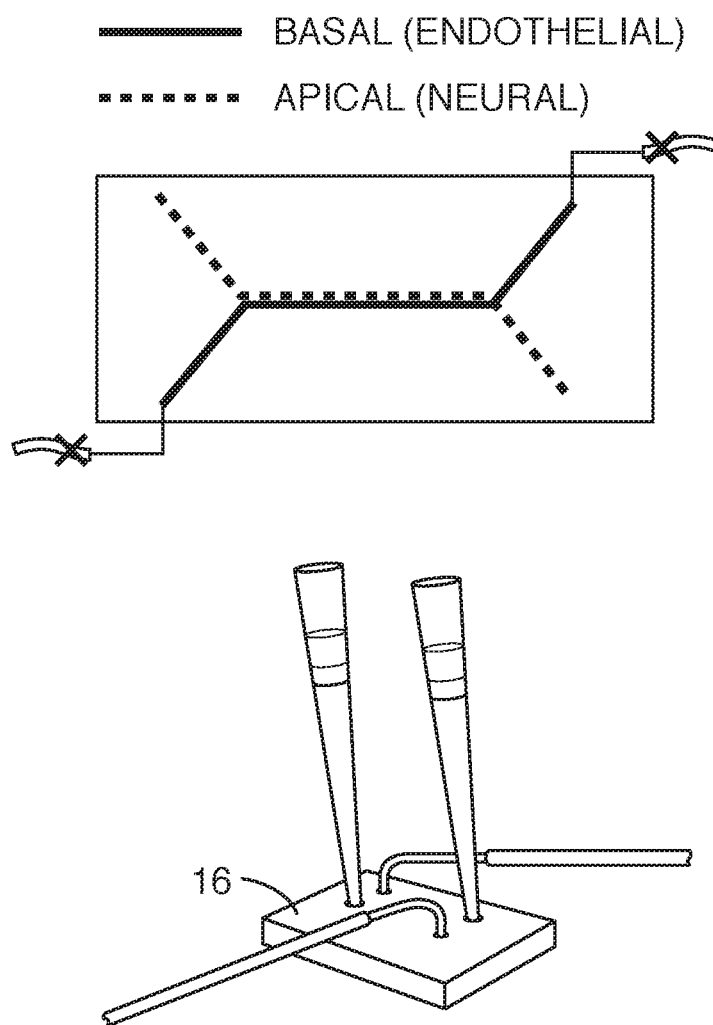
FIG. 2 shows two schematics of microfluidic devices. In one embodiment of a microfluidic device or chip (top), the device comprises top (apical) and bottom (basal) channels (the two Xs indicating that channels are blocked during at least part of the protocol). The other schematic (bottom) shows how the ports of a microfluidic device or chip (16) can be utilized to deposit fluids carrying surface coatings (e.g. dissolved proteins) and/or seed the cells using pipette tips. This image shows a modification to the typical chip ECM coating protocol based on the need in some embodiments to coat the top and bottom channels with different ECM solutions in wet and dry conditions. The procedure developed involved an "air dam" by which perfusion of ECM1 loaded into the bottom channel was prevented from perfusing through the membrane to the top channel by clamping flexible tubing and trapping air in the top channel. The ports of a second microfluidic channel can be air-filled and plugged up using clips, for example.

While a variety of protocols were explored, one embodiment for preparing and seeding a microfluidic chip comprising six steps. FIG. 1 shows the workflow. First, the chip (or regions thereof) are treated to promote wetting or protein adhesion (e.g. by plasma treatment). One or more channels are then plugged (see the top schematic of FIG. 2, where an "X" indicates a channel is blocked in a microfluidic device or chip with top and bottom channels). FIG. 2 (bottom schematic) shows how the ports of a microfluidic device can be utilized to introduce fluid (e.g. with ECMs) or cells using pipette tips. Using the protocol, the ECM mixture for the bottom channel is introduced first, with the excess removed, and the remainder dried. Thereafter (step 3), the ECM for the top channel is introduced. The BMECs can be seeded on the bottom channel. The top channel can be washed. Finally, the neural cells can be introduced and incubated for attachment. Cultures were seeded into chips following the seeding of BMECs described above either on the same day or the following day after BMECs had been seeded onto the chip. The chips were cultured for 14 days and fixed and stained for relevant markers. Confocal imaging shows the transmigration in z-stack.

Figure 3A:
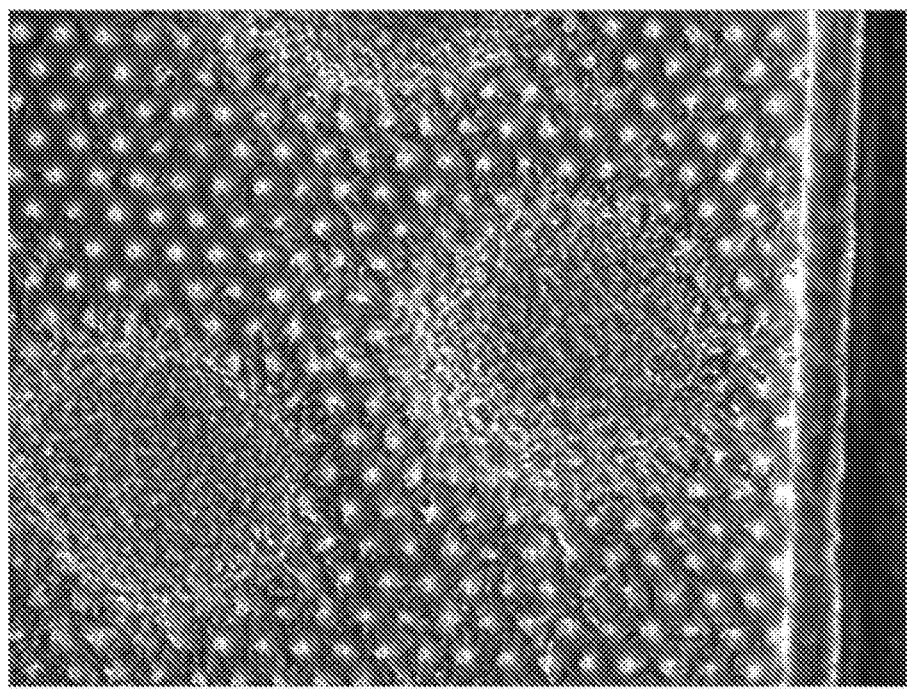
FIG. 3A-B provides a microscopic analysis of Chip 166 from Table 2, showing neural cells in the top channel of the microfluidic device (FIG. 3A) and BMECs on the bottom channel of the microfluidic device (FIG. 3B)
Figure 3B:
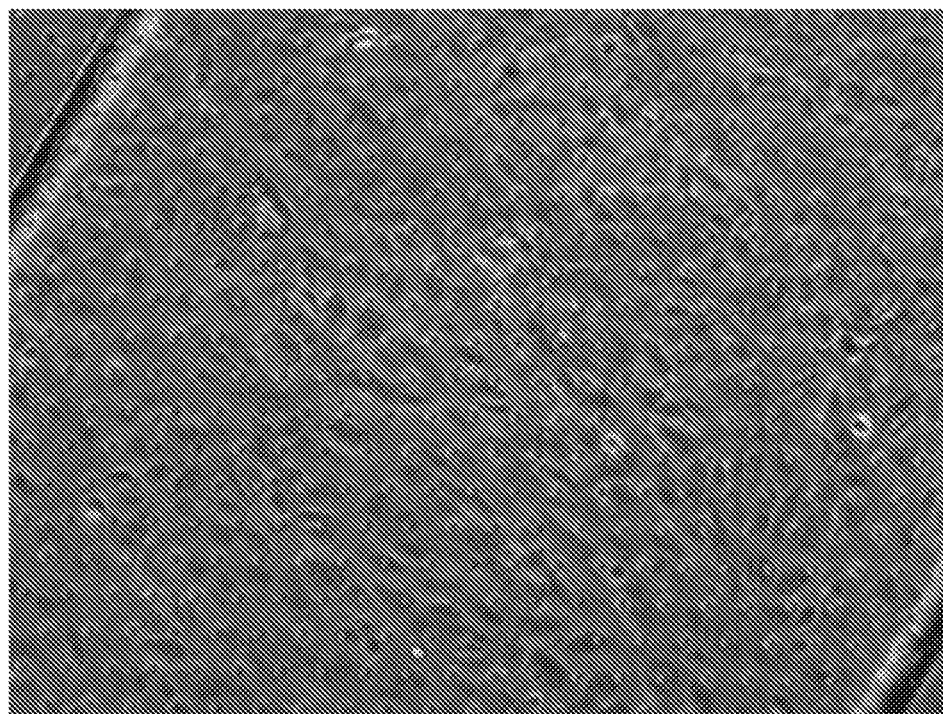

FIG. 3A-B provides a microscopic analysis of Chip 166 from Table 2, showing neural cells in the top channel of the microfluidic device (left) and BMECs on the bottom channel of the microfluidic device (right). The neural cells and BMECs have attached.

Figure 4B:
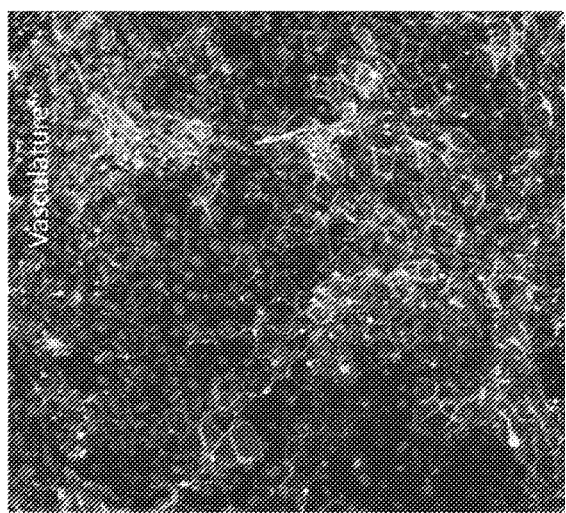
FIG. 4A-C provides three images from a microfluidic chip where the cells have been tested for markers to confirm their identity. The top right image (FIG. 4B) shows good staining of BMEC tight junctions indicating BBB formation on chip. On the top left (FIG. 4A), the staining shows neurons and astrocytes.
Figure 4A:
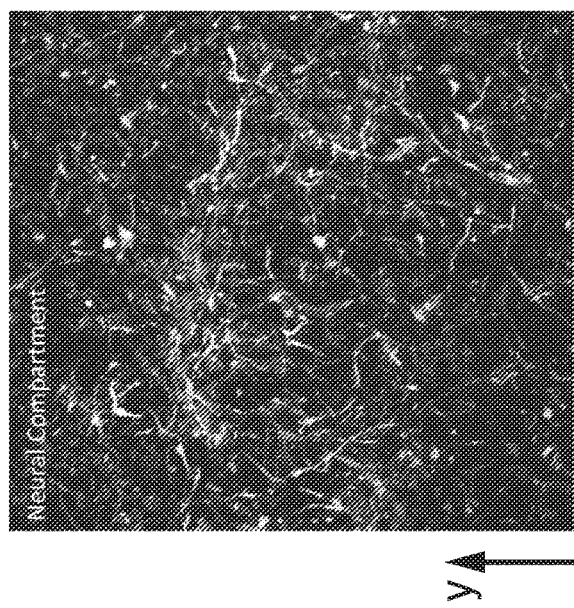
Figure 4C:
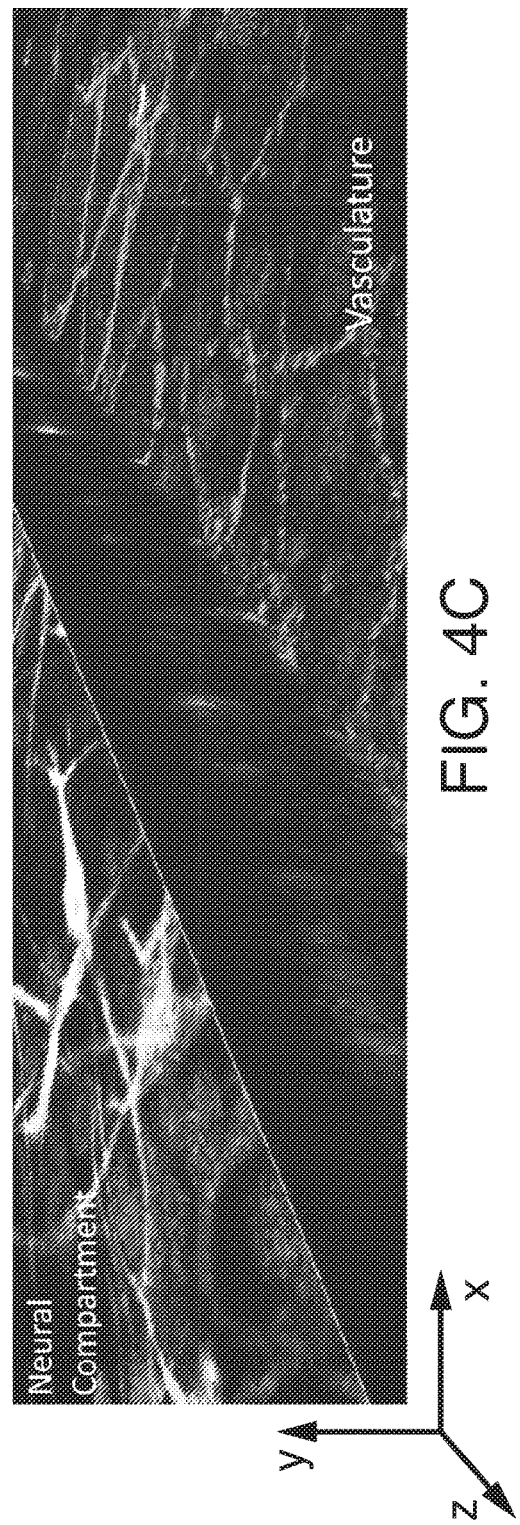

The attached cells were then tested for markers to confirm their identity. FIG. 4A-C is a vertical 2D projection of a 3D confocal stack of images slices, which allows for visualization of the neurons and endothelial cells together, even though they are not in the same plane on the microfluidic device. The BMECs display the Glut 1 marker, while the neurons are positive for NFH. DAPI was used to stain the nuclei.

Figure 5:
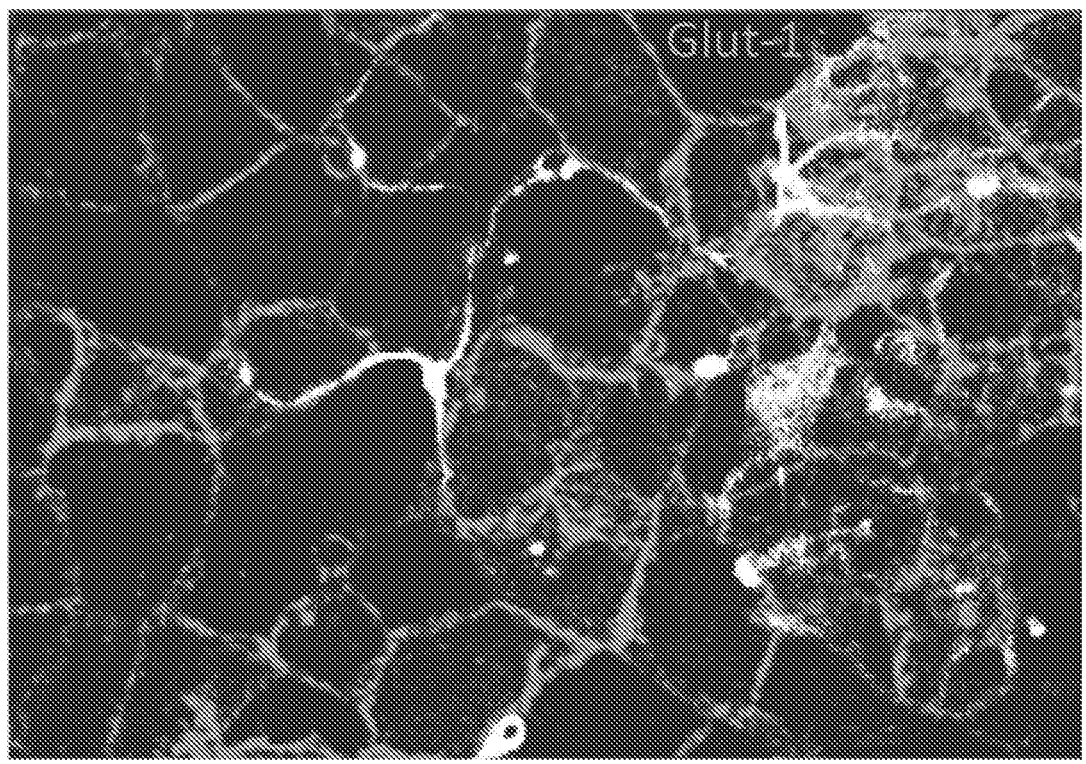
FIG. 5 provides an image from a microfluidic chip wherein at least a portion of an apical astrocyte (i.e. the endfoot) has transmigrated the membrane and contacted the BMECs on the other side. Contact or interfacing between astrocytes and endothelial cells is a recognized feature of in vivo blood-brain barriers. To our knowledge, this interface has never been previously observed in in vitro models of the blood-brain barrier. The potential for the formation of astrocyte-endothelial contact observed in some of the embodiments disclosed herein is desired and advantageous, as it is believed that the in vivo contact/junction is related to the tight barrier properties characteristic of the blood-brain barrier.

FIG. 5 provides an image from a microfluidic chip wherein at least a portion of an apical astrocyte (i.e. the endfoot) has transmigrated the membrane and contacted the BMECs on the other side. The astrocytes are shown in white against the red stained BMECs.

Example 4

Figure 6A:
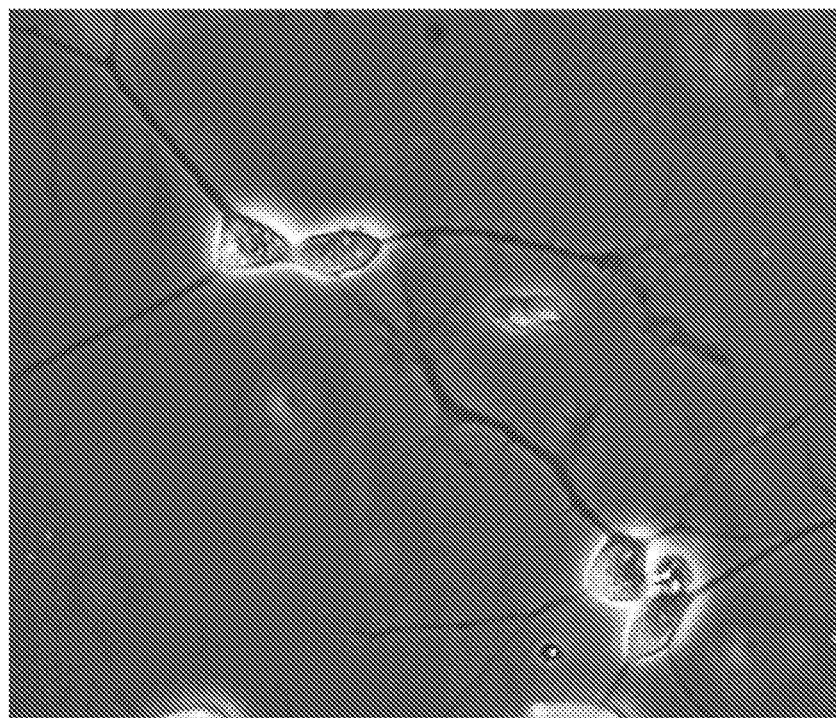
FIG. 6A-B shows a first image (FIG. 6A) where iMNs were seeded on a plain (un-patterned) surface, as well as a second image (FIG. 6B) where the same cells were seeded on a nanopatterned surface, resulting in directed neurite growth. Such nanopatterning can be applied to the membrane or any surface of the BBB-on-chip. In particular embodiments, the nanopatterning is applied to the top surface of the membrane to direct neurite growth for neuron seeded on said surface. It is desired in some uses to direct neurite growth, for example, in studying neuron biology or disease (e.g. conditions that disturb neurite growth or its directionality), as a readout of neuron or blood-brain-barrier health (e.g. by monitoring neurite growth or its directionality) or in facilitating electrophysiological measurements (e.g. using a multi-electrode array or patch clamping). The preferred nanopattern is linear valleys and ridges, but alternatives such as circular, curved, or any other desired shape or combination thereof are also contemplated. Linear nanopatterning can include, for example, line spacing ranging from 10 nm to 1 um, 0.5 um to 10 um or 5 um to 50 um, and line depth ranging from 10 nm to 100 nm, 50 nm to 1000 nm, 200 nm to 5 um or 2 um to 50 um.
Figure 6B:
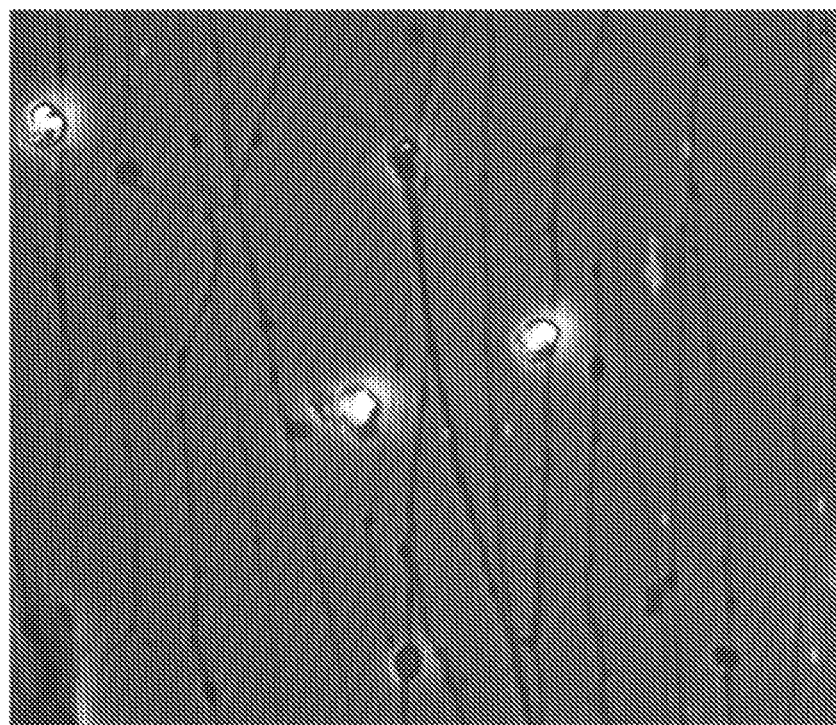

The present invention contemplates, in one embodiment, utilizing nanopatterned surfaces for seeding cells. FIG. 6A shows a first image (top) where iMNPs were seeded on a plain (un-patterned) surface, as well as FIG. 6B second image (bottom) where the same cells were seeded on a nanopatterned surface. Clearly, the nanopatterned surface results in directed neurite growth (e.g. in a line pattern)

Example 5

Figure 7A:
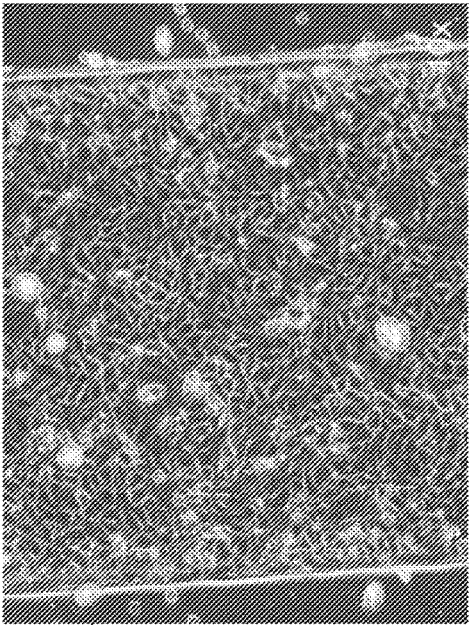
FIG. 7A-D show microscopic examination of the morphology of fresh (not frozen) BMECs seeded on a 4:1 mixture of collagen and fibronectin that has either been dried (FIG. 7A, top left) or remained wet (FIG. 7B, top right), as well as an example where the same fresh cells were seeded on laminin (FIGS. 7C and 7D), the arrow indicating contamination of the cells with neurons).
Figure 7B:
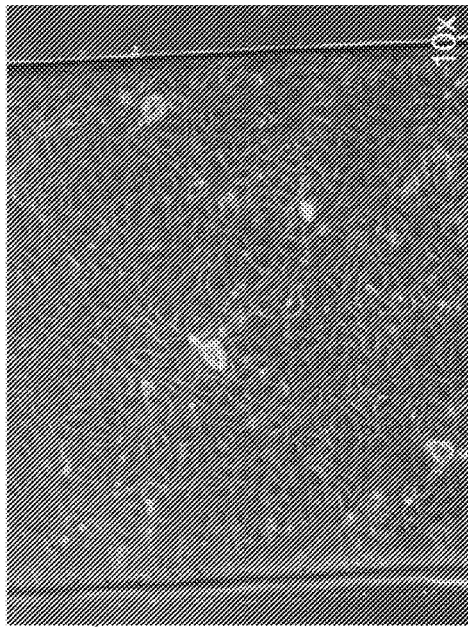
Figure 7C:
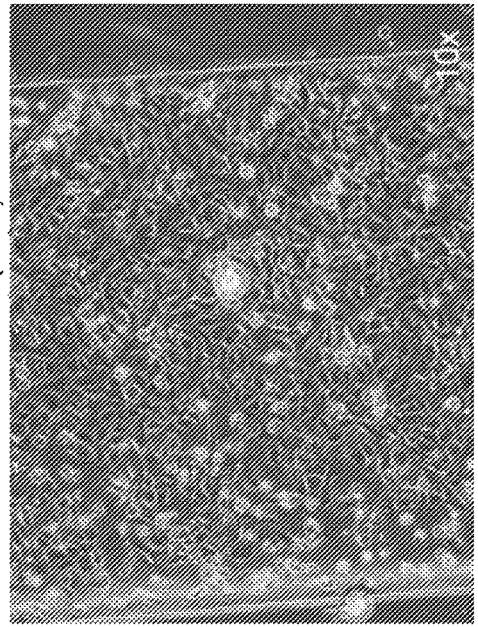
Figure 7D:
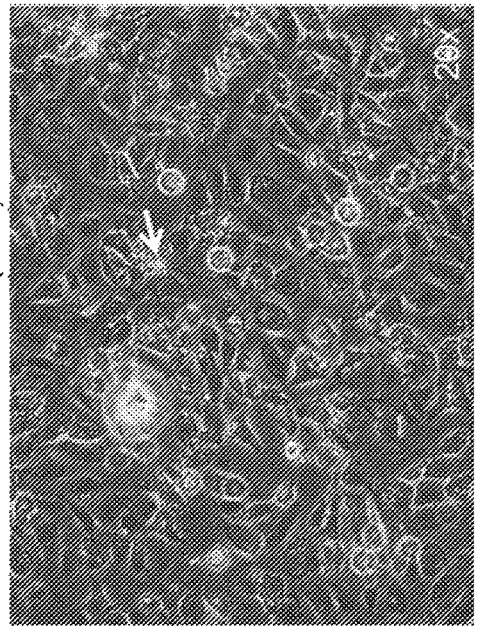

While frozen stocks of cells can be used (particular for the neural cells), it was found that better results can be obtained (particularly for BMECs) when fresh cells are used for seeding. FIG. 7A-D show microscopic examination of the morphology of fresh (not frozen) BMECs seeded on a mixture of collagen and fibronectin that has either been dried (FIG. 7A, top left) or remained wet (FIG. 7B, top right), as well as an example where the same fresh cells were seeded on laminin (FIGS. 7C and 7D). Interestingly, when laminin was used, the BMECs were not free of neurons (see the arrow in FIG. 7D indicating contamination of the cells with neurons).

Tables 3 and 4 show various conditions tested for seeding fresh neural (iMNPs) and fresh endothelial cells (iBMECs), where the particular conditions are associated by microfluidic chip number, allowing for a correlation of good tight junctions with the seeding conditions. Staining results (not shown) for microfluidic chip 574 (see Table 3 for conditions) indicated the cells are positive for Glut 1 (red stain), which is a marker of BMEC tight junctions (the nuclei were also stained blue from DAPI). The seeding conditions for chip 574 resulted in good tight junctions.

Staining results (not shown) for microfluidic chip 665 (see Table 3 for conditions) indicated that the cells are positive for Glut 1. Thus, the seeding conditions for chip 665 also resulted in good tight junctions. Staining results (not shown) for microfluidic chip 667 (see Table 3 for conditions) indicated the cells are positive for Glut 1. Thus, the seeding conditions for chip 667 resulted in good tight junctions. Staining results for microfluidic chip 693 (see Table 3 for conditions) indicated the cells are positive for Glut 1. Thus, the seeding conditions for chip 693 resulted in good tight junctions.

Staining results (not shown) for microfluidic chip 733 (see Table 4 for conditions) indicated the cells are positive for Glut 1. The results (not shown) also revealed that coating with laminin alone (before seeding) results in poor BMEC tight junction formation.

Example 6

Figure 8:
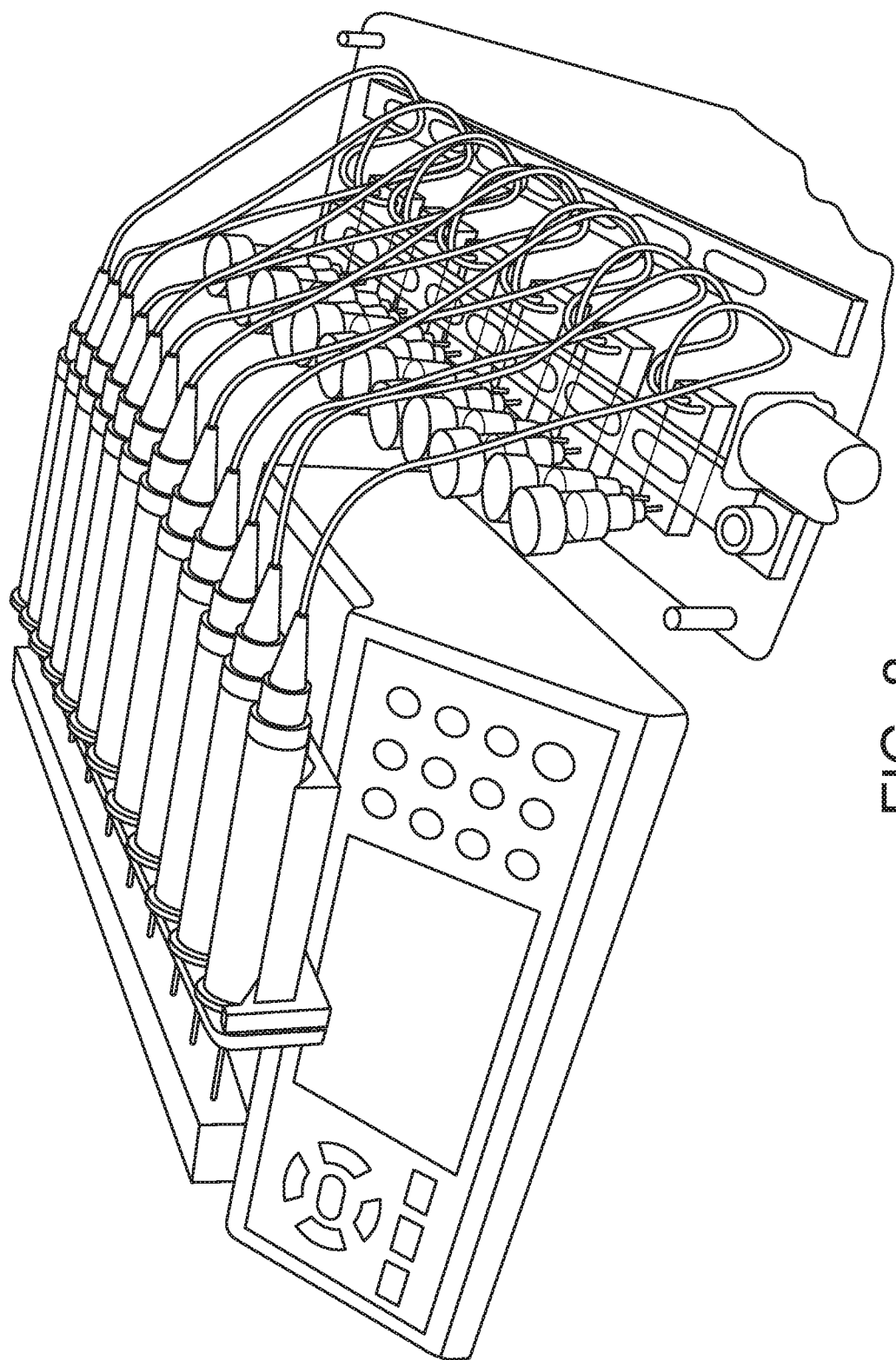
FIG. 8 is a schematic showing one embodiment of a standard syringe pump and reservoir setup for perfusion of the chips mediated by flexible tubing for introducing flow into the microfluidic chips. A plurality of fluid reservoirs are in fluidic communication with a corresponding plurality of microfluidic chips via inlet ports, with tubing coming from the exit ports and attached to a plurality of syringes used to draw fluid through the chip at a flow rate. While a convenient method for creating flow conditions, other methods involving different pumping approaches or pressure approaches to drive fluid are contemplated.
Figure 9A:
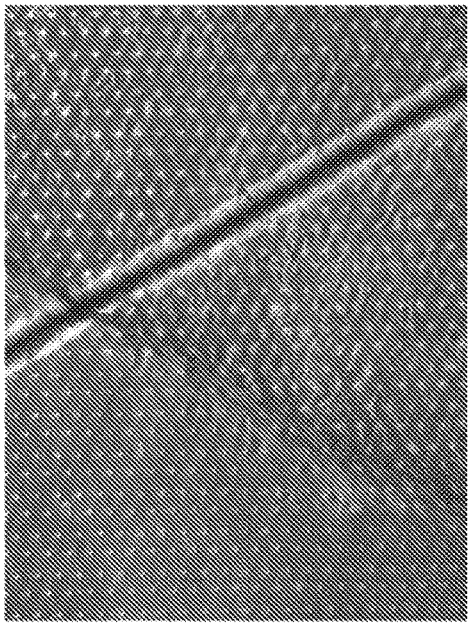
FIG. 9A-D comprises photographs of microscopic examination of cell morphology on the bottom (left-hand side) and top (right-hand side) of the membrane in a microfluidic device where the cells have been exposed to flow (using the system of FIG. 8) for a number of days (7 days).
Figure 9B:
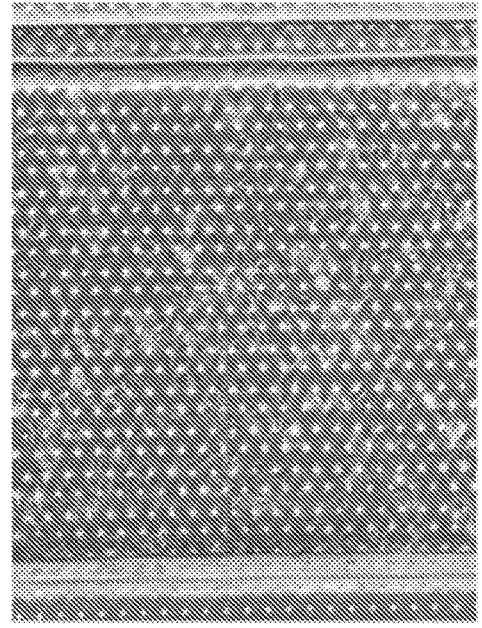
Figure 9C:
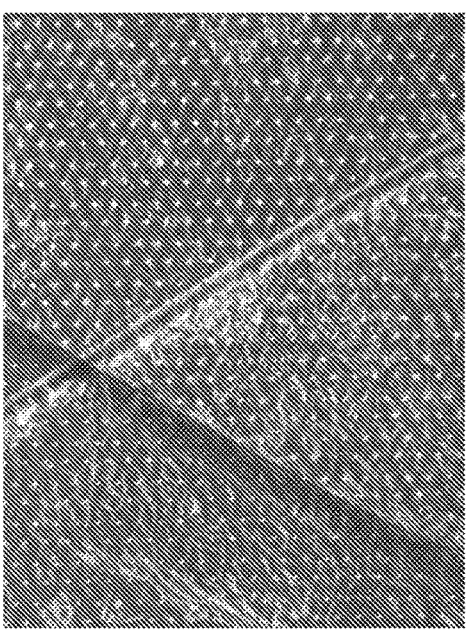
Figure 9D:
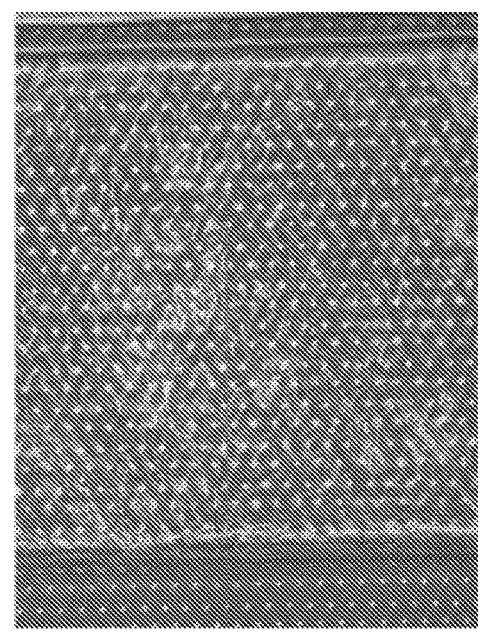
Figure 10:
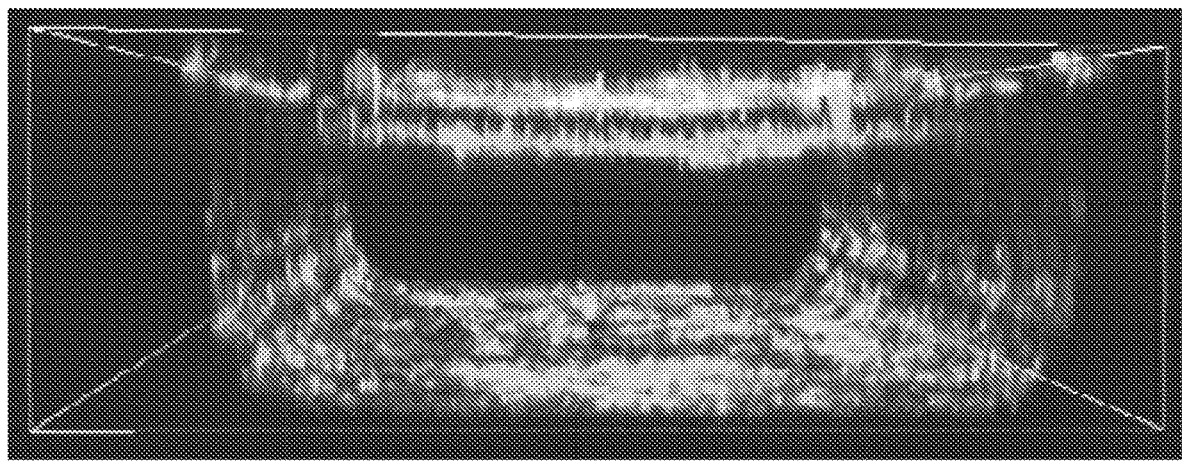
FIG. 10 is a photograph of fluorescent staining of cells in a microfluidic device where the cells have been exposed to flow (using the system of FIG. 8) for a number of days. The image is a 3D image of the BMEC in the bottom channel showing a complete contiguous BMEC lumen being formed in the chip.
Figure 11:
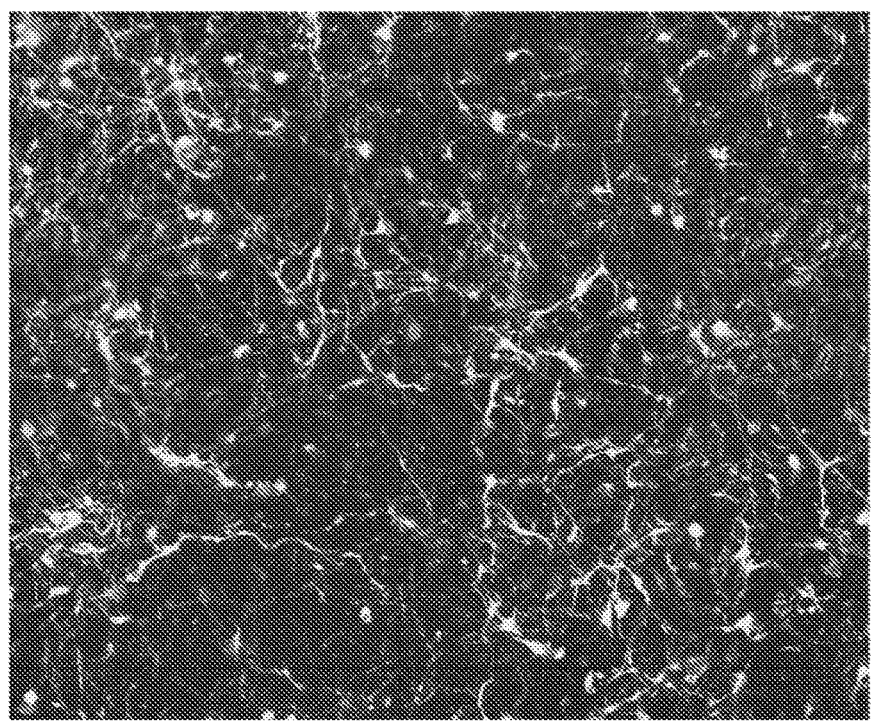
FIG. 11 is a photograph of fluorescent staining of cells showing the presence of neural stem cells (red) in addition to neural filaments (green), with the nuclei stained with DAPI. In the preferred embodiment, the BBB-on-chip includes endothelial or endothelial-like cells (preferably brain-related endothelial cells) and optionally astrocytes or astrocyte-like cells. However, in some embodiments, the BBB-on-chip contains additional cells type such as, for example, neurons, pericytes and various progenitor cells. Such cells may be included as an intended or unintended bi-product of the stem cell differentiation process from which the astrocytes or endothelial cells are generated (whether on chip or preceding it), as stem cells and progenitor cells are typically capable of differentiating into a plurality of cells types. The presence of neurons is desirable in some embodiments because they can be used as readouts of BBB function (e.g. agents penetrating the barrier may affect the neurons in measurable ways) or because they may interact with other cells types or help generate a local environment that improves the function of the BBB-on-chip. Similarly, pericytes are desirable in some embodiments, because it is believed in the art that they help establish the blood-brain barrier and can be potentially monitored to evaluate BBB health. Neuronal- or endothelial-lineage progenitors are desirable in some embodiments, as they may replenish cell populations and be potentially monitored to evaluate BBB health. Accordingly, in some embodiments, neurons, pericytes, neuronal-lineage progenitors, endothelial-lineage progenitors or combinations thereof or progenitors thereof may be deposited in the BBB-on-chip. In other embodiments, a differentiation process is employed (whether on chip or preceding it) to generate one or more of these cells types.

Unlike conventional static cultures, the present invention contemplates microfluidic devices where the cells are exposed to a constant flow of media providing nutrients and removing waste. FIG. 8 is a photograph showing one embodiment of a system for introducing flow into the microfluidic chips. A plurality of fluid reservoirs are in fluidic communication with a corresponding plurality of microfluidic chips via inlet ports, with tubing coming from the exit ports and attached to a plurality of syringes used to draw fluid through the chip at a flow rate. FIG. 9A-D comprises photographs of microscopic examination of cell morphology on the bottom (left-hand side) and top (right-hand side) of the membrane in a microfluidic device where the cells have been exposed to flow (using the system of FIG. 8) for a number of days. FIG. 10 shows fluorescent staining of cells in a microfluidic device where the cells have been exposed to flow (using the system of FIG. 8) for a number of days. The image is a 3D image of the BMEC in the bottom channel showing a complete contiguous BMEC lumen being formed in the chip. FIG. 11 is a photograph of fluorescent staining of cells showing the presence of neural stem cells (red) in addition to neurites (green), with the nuclei stained with DAPI.

Example 7

Good cell viability and function on the BB-on-chip allow for measurements of barrier integrity and physiology, whether by TEER, patch clamp or other testing measures.

Figure 12A:
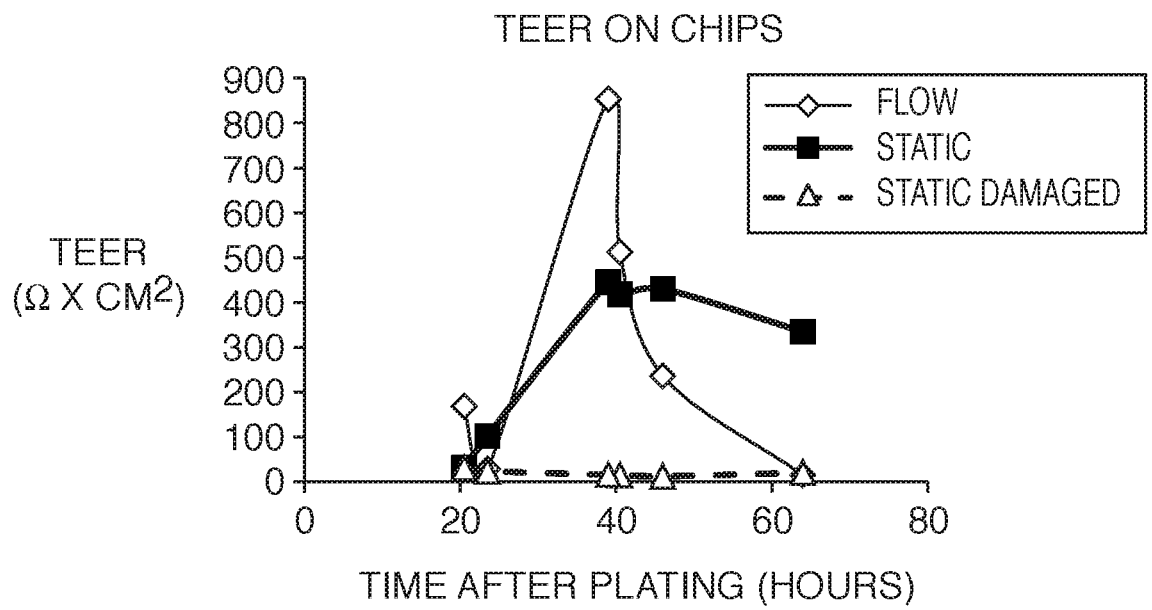
FIGS. 12A and 12B show graphs with functional measurements performed on BBB-on-chips.
Figure 12B:
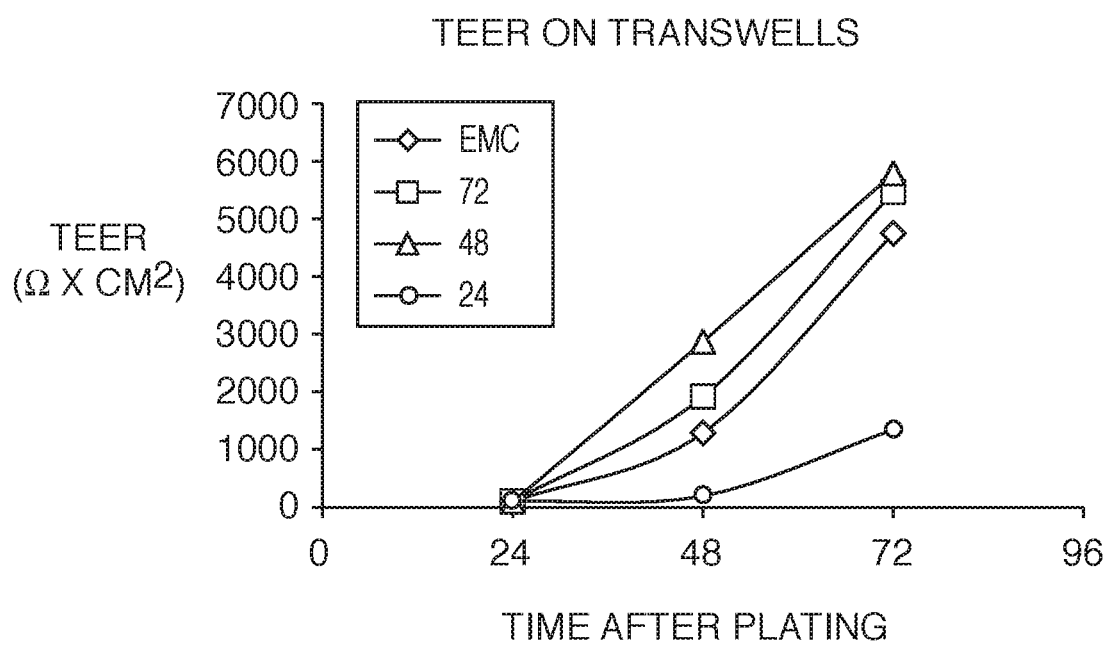
Figure 13A:
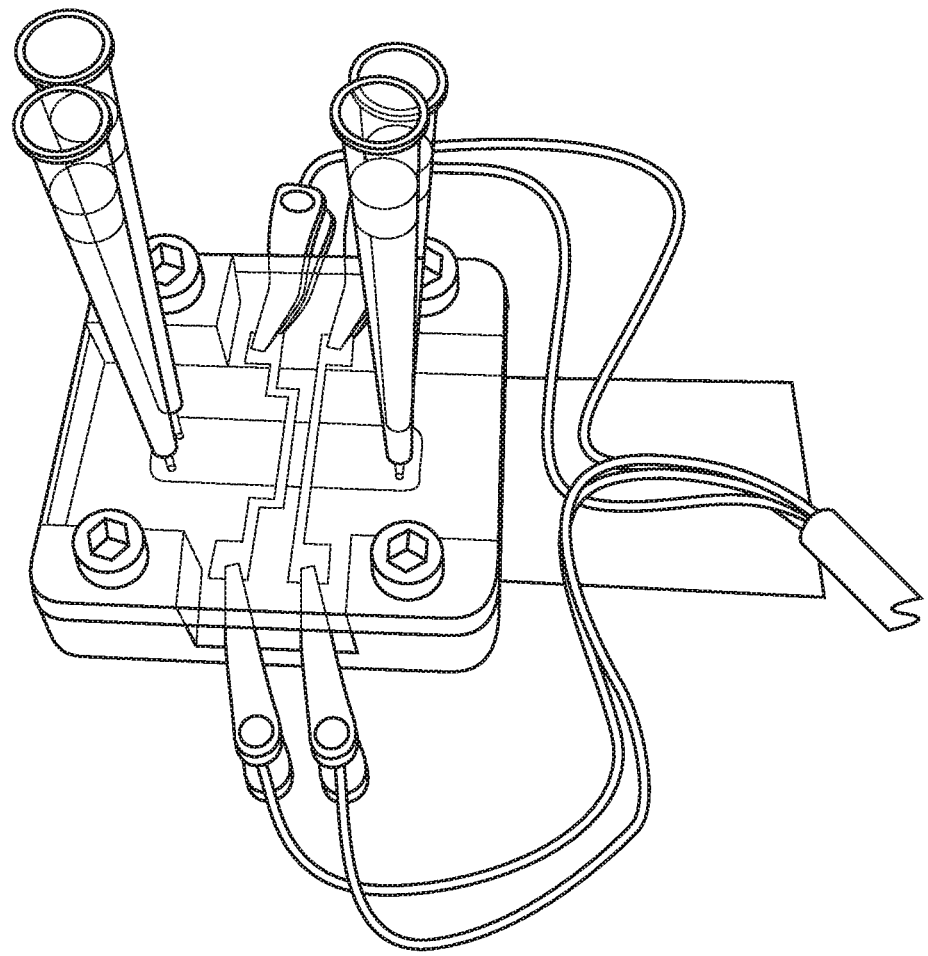

TEER: FIG. 12A shows the results/readout from transepithelial electrical resistance (TEER) measurements on the microfluidic chip under flow, static, and control conditions. Cells were plated on tall channel PDMS chips equipped with incorporated gold electrodes on each channel (see FIG. 13A). Post seeding of BMECs, transendothelial electrical resistance was measured by connecting the electrodes to an EVOM2 voltohmmeter (see FIG. 13B). FIG. 12A displays preliminary data indicating the beneficial effect of flow in the BBB-on-chip, i.e. higher TEER in response to flow. In particular, at around the 40 hour time point, the TEER value observed for a BBB-on-chip under flow was significantly higher than a similar chip under static conditions, i.e. that the iPS brain microvascular endothelial cells (iBMECs) formed tighter cell-cell junctions or barrier function under flow conditions on a prototype TEER-Chip as compared to a chip maintained in static culture. The "damaged" chip was a failure due to the TEER-Chips being a prototype. FIG. 12B shows TEER results where the cells were cultured in transwells.

Figure 14A:
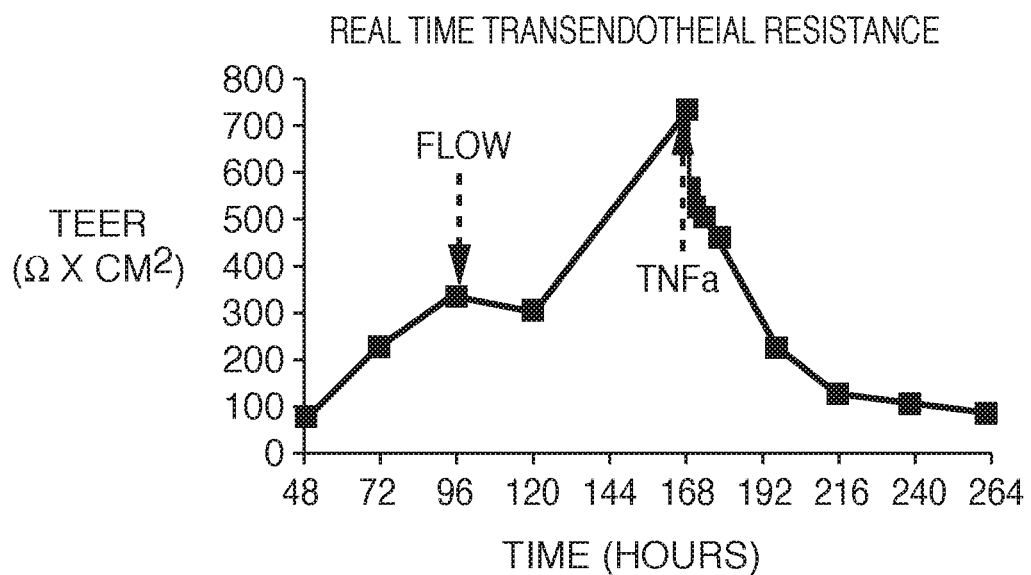
FIG. 14A was a follow-up experiment on another round of prototype TEER chips that showed iBMEC barrier function increasing in the presence of flow on a chip followed by a weakening of barrier function with the exposure of the chips to TNFa, a proinflammatory cytokine. Higher TEER values generally indicate a tighter barrier, which is typically desirable for a blood-brain barrier.

FIG. 14A was a follow-up experiment on another round of prototype TEER chips that showed iBMEC barrier function increasing in the presence of flow on a chip followed by a weakening of barrier function with the exposure of the chips to TNFa, a proinflammatory cytokine. Higher TEER values generally indicate a tighter barrier, which is typically desirable for a blood-brain barrier.

Figure 18A:
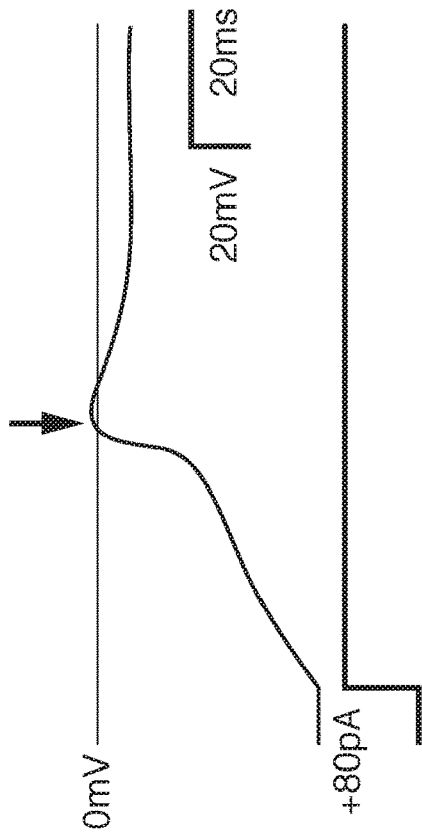
FIG. 18A-B shows electrophysiology recordings collected by patch-clamp from neurons in the microfluidic device ("BBB-on-Chip"). An arrow (FIG. 18A) indicates single action potential. Current recordings (FIG. 18B, right) show negative sodium channel currents ($Na^+$) and positive potassium channel ($K^+$). These measurements on-chip can be used, for example, to provide an indication of neuronal maturation or as a readout of neuron health. In turn, neuronal maturation or health can be used as indicators of BBB-on-chip quality (for example, before starting an experiment) or as an experimental endpoint indicating, for example, that an agent as crossed the BBB, a disease condition has emerged, the BBB has been modified or compromised, or conversely, that the BBB or neural function or health have improved. Patch clamping can be performed on the BBB-on-chip by a variety of methods, including for example, by inserting the patch-clamp electrodes through the soft body of an elastomeric BBB-on-chip device. Similarly to patch-clamping, other electrophysiological readouts can be obtained, for example by including one or more electrodes in the device. In particular, a multi-electrode array (MEA) can be integrated on the membrane of embodiments that possess one or similarly in fluidic channels or cavities within the device. Electrophysiological measurements (patch-clamping, MEA) can also be applied to astrocytes, which have been shown in the art to be excitable.
Figure 18B:
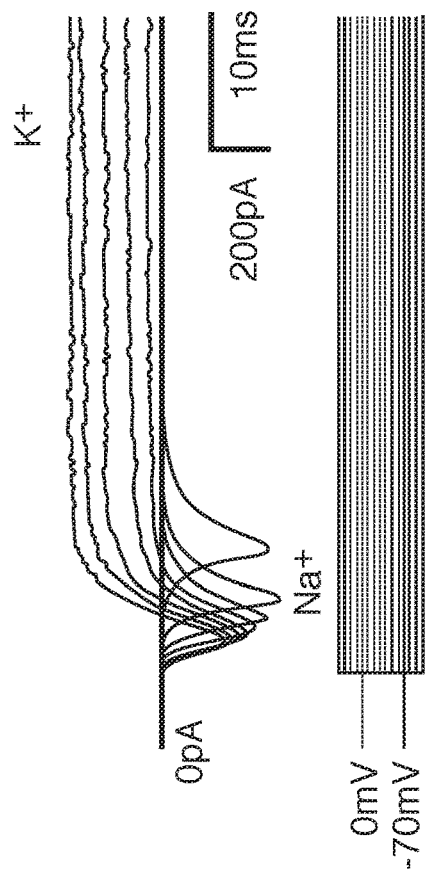
Figure 20:
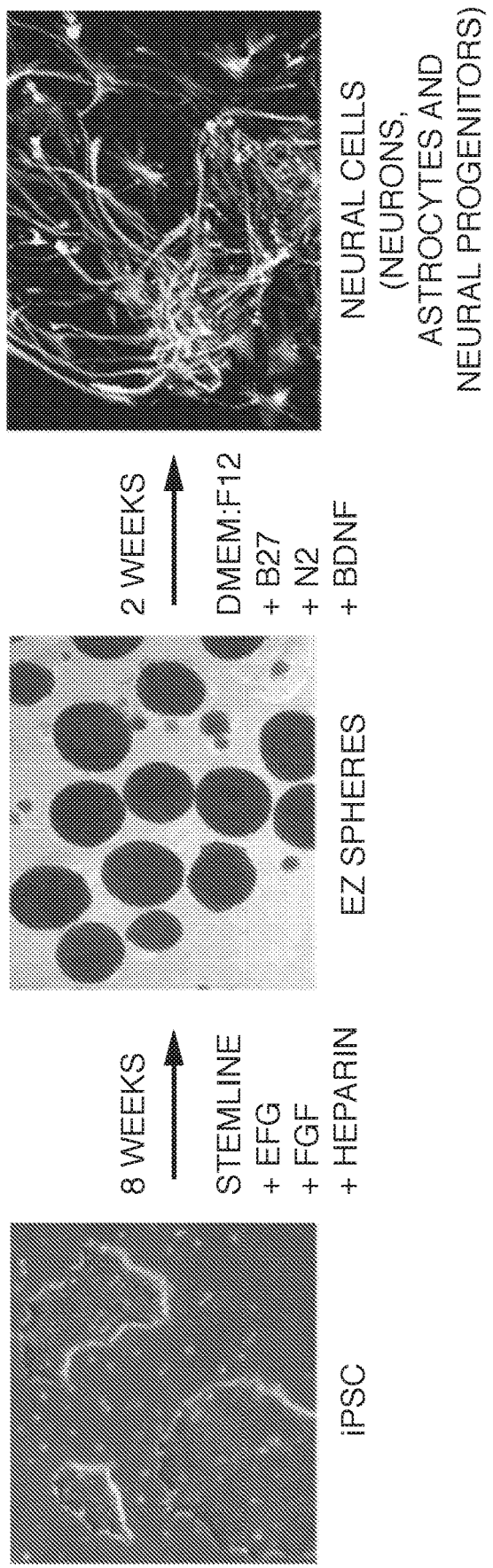
FIG. 20 shows both a protocol for generating, and staining results confirming the generation of, neural cells from neural progenitors. Such techniques allow one to make multipotent neural stem cells and motor neuron precursor directly from iPSC, allowing differentiation into many neural cell types (neurons, astrocytes, etc.).

PATCH CLAMP: FIG. 18A-B shows electrophysiology recordings collected by patch-clamp from neurons in the microfluidic device ("BBB-on-Chip"). These measurements on-chip can be used to provide an indication of neuronal maturation, i.e. more precisely describe the maturity of a neuronal cell. Cells were cultured as described above in a specially designed "openable" chip (where the chips can be partially disassembled to expose directly cells on the semi-porous membrane) with a stiff PET membrane to aid in patch-clamp recording. PDMS was attempted, but was unsuccessful. PET membrane chips were opened at endpoint at 6 and 24 days in chip. Individual neurons seeded into the chip were directly accessed with a glass micropipette, and cell electrophysiology was recorded including capacitance, membrane resting voltage, spontaneous activity and induced activity. FIG. 18A-B is a whole cell patch recording of an induced action potential from a neuron cultured on the chip. An arrow (FIG. 18A) indicates single action potential. Current recordings (FIG. 18B, right) show negative sodium channel currents ($Na^+$) and positive potassium channel ($K^+$) are necessary for normal neuron function and become more pronounced as a neuron matures.

CALCIUM FLUX: FIG. 19A-D show the results of calcium flux imaging in the neural channel. Using a florescent calcium influx-activated dye (Fluo-4), neurons seeded in chip were imaged using high resolution high frame-rate camera. Florescence intensity changes of up to hundreds of neurons were analyzed simultaneously by recording average pixel intensity over time (dF/F). These values were plotted with respect to time and are analyzed for waveform properties, which correlate spontaneous neural activity and neural network formation. This is accomplished through multi-step video post-processing and signal analysis (including video compression, signal cleanup, automatic or manual ROI detection, etc. which can be implemented from open-source MATLAB software packages). The photograph (FIG. 19A, top left) is a single fluorescent image from a movie of such images. The colored circles indicate the positions that correspond to the time traces in the 3 graphs. The traces show that it is possible to observe neuronal function in the microfluidic chips in real-time. In this case, it is shown that Ca2+ fluxes can be measured on chips to give a direct readout of neuronal activity. The addition of tetrodotoxin (TTX), which is a potent blocker of voltage-gated calcium channels, ablates this activity (FIG. 19D, bottom right). This type of experiment will be important when the neuronal activity is modulated by pharmacological stimulation.

ICC overlay data: By overlaying images taken after staining the cells, specific cell identification can be combined with original activity traces to determine specific activities of individual cell types in the chip. The overlay data (not shown) indicates that motor neurons are indeed more active in the chip. This can also be accomplished with cell type specific reporter lines.

Example 8

Brain microvascular endothelial cells (BMECs) constitute the blood-brain barrier (BBB) which forms a dynamic interface between the blood and the central nervous system (CNS) in vivo. This highly specialized interface restricts paracellular diffusion of fluids and solutes including chemicals, toxins and drugs from entering the brain. In this example, fluorescein sodium is used in a paracellular permeability assay of the BMECs seeded on a microfluidic device.

Figure 14B:
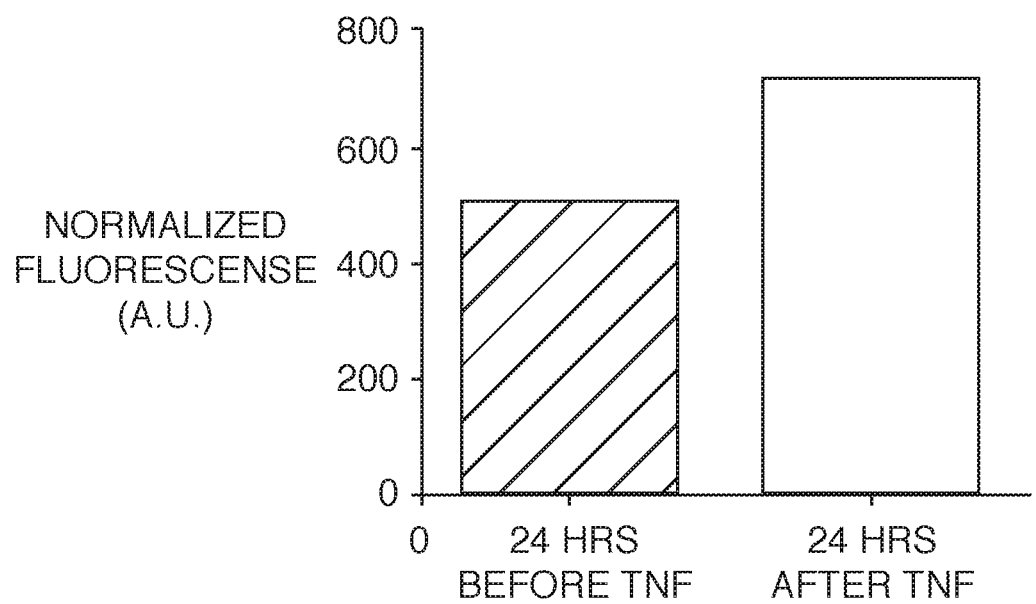
FIG. 14B also involves TNF alpha exposure, but the readout is membrane permeability as measured by Dextran-FITC.

Albumin or Dextran conjugated to a fluorescent probe (e.g., FITC or TRITC) are frequently used to monitor changes in leakage, and thus barrier function. In this case, Dextran-FITC, a green fluorescent molecule of 4 KDa, or sodium fluorescein (a 0.3 KDa molecule), was added to the bottom ("blood side") channel. Paracellular permeability was calculated by measuring the permeability of the fluorescent molecule on the Top ("brain side") channel. Low permeability is an indication for proper barrier functions. FIG. 14B involves TNF-alpha exposure, but the readout is membrane permeability as measured by Dextran-FITC. FIG. 14B confirms that TNFa exposure results in a decrease in barrier function and TEER by an increase in permeability through the semi-porous membrane by dextran-FITC, a fluorescently labeled small molecule.

FIG. 15 shows the results for (and structure of) fluorescein sodium from a paracellular permeability assay. Chips were seeded with iPSC-derived BMECs taken from healthy controls (CTR) or MCT8-deficient patients, and the paracellular permeability was determined by monitoring Blood to brain permeability of the sodium fluorescein tracer as described above. Flow is clearly important.

In the present experiment, the agent used was fluorescein. In some aspects of the present invention, it is contemplated that similar testing will be done to ascertain permeability for various additional agents (e.g. drugs, chemicals, hormones, blood components, biomarkers). Such methods can allow qualitative or quantitative estimation of the permeability of the in vivo blood-brain barrier to the one or more agents. Furthermore, according to some aspects of the present invention, the permeability of one agent is measured in response to a second agent, treatment or experimental condition (for example, measuring the effect of a medication on the blood-brain barrier permeability of another medication). It is important to note that although we refer to permeability, we do not mean to exclude active transport, pumping or any other means for an agent to pass from one side of the barrier to the other (regardless of direction). The penetration of an agent through the barrier can be measured, for example, using mass spectroscopy, antibody-based methods (e.g. ELISAs, Western blots, bead-based assays), or optical methods (e.g. fluorescence signature, Raman spectroscopy, absorbance).

Example 9

Some embodiments include blood or blood components, optionally perfused through one or more fluidic channels within the device. The use of blood of blood components is desired as the blood or blood components can improve BBB-on-chip function, for example, by providing biochemical cues, or conversely hurt the BBB-on-chip, for example, because the blood may contain a harmful agent that may be under investigation. In some aspects, permeability assays include blood or blood components in order to provide a potentially more in vivo like result. In other aspects, individual-specific blood or blood components are used in order to potentially provide individualized BBB-related measures. This can include, for example, the measurement of the permeability of one or more agents or components from the blood or components, the effect of the blood or components on the permeability of one or more agents that may be added to the blood or another fluid included in the device, the effect of the blood or components on the health of the BBB-on-chip or any of its components (whether positive or negative), etc. This may include diagnostic uses, for example, to identify a disease, biomarker or infectious agent carried by the blood or blood components.

In this example, hormone transport across the BMECs was measured in the "BBB-on-chip" in healthy and diseased tissue by mass spectrometry. Thyroid hormone was added to the bottom channel and measured on the top channel. Thyroid hormones ($T_3$ and $T_4$) were detected using Liquid chromatography tandem-mass spectrometry (LC-MS/MS).

Figure 16A:
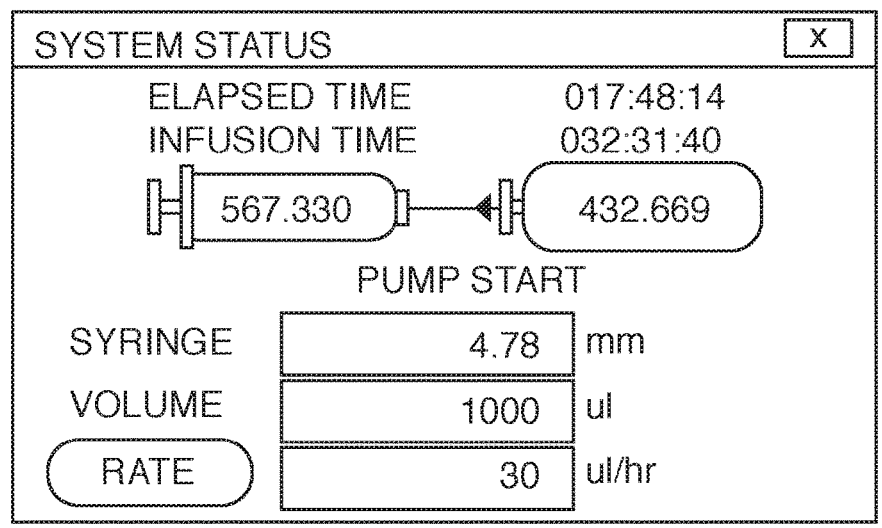
FIG. 16A shows the user interface and the conditions during the run of human blood across the blood brain barrier.
Figure 16B:
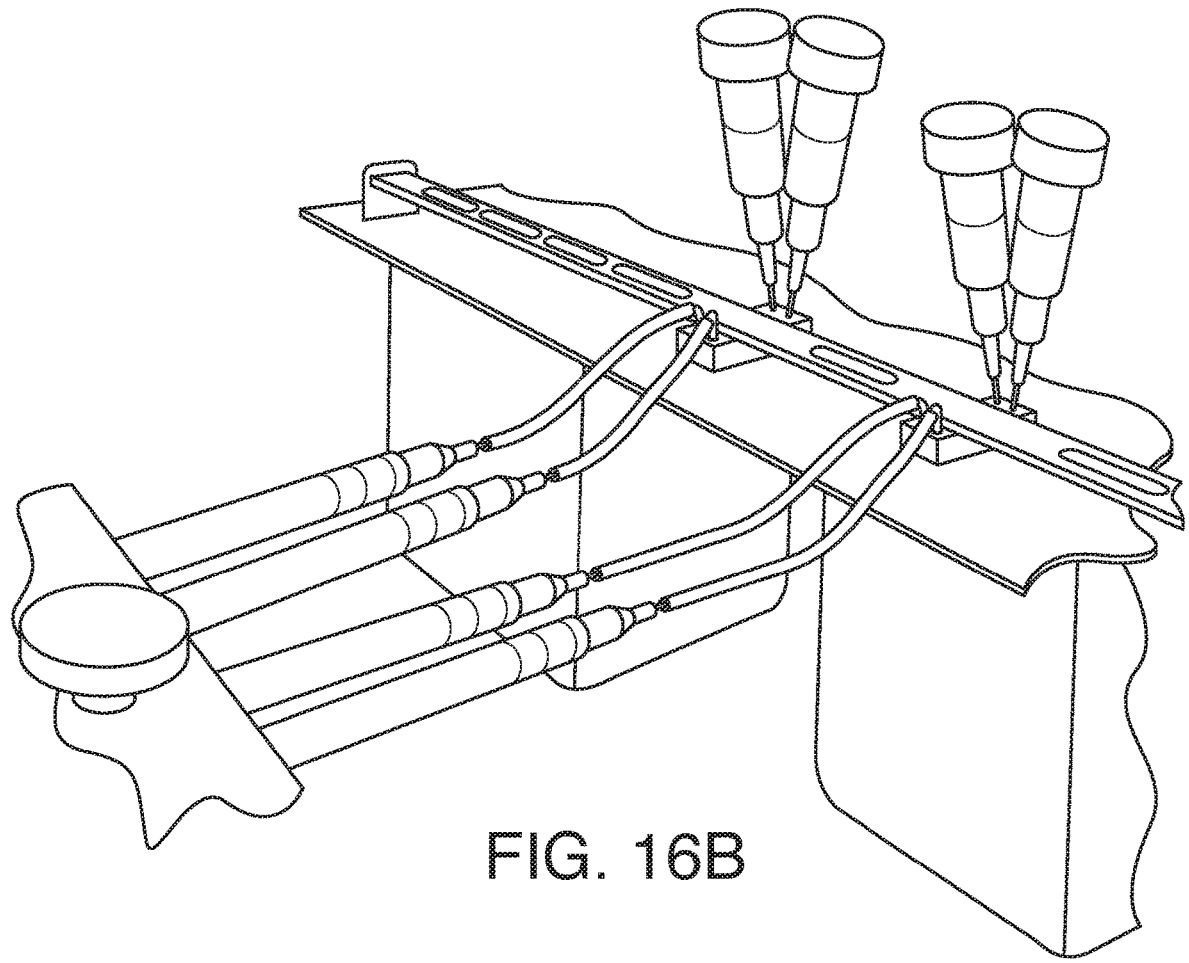
FIG. 16B shows the equipment setup for measuring the transport of solutes from human blood across the blood brain barrier (BBB), a barrier created in vitro in the microfluidic devices described herein using a layer of BMECs. As evidenced, some embodiments include blood or blood components, optionally perfused through one or more fluidic channels within the device. The use of blood of blood components is desired in some embodiments, as the blood or blood components can improve BBB-on-chip function, for example, by providing biochemical cues, or conversely hurt the BBB-on-chip, for example, because the blood may contain a harmful agent that may be under investigation. In some aspects, permeability assays include blood or blood components in order to provide a potentially more in vivo like result. In other aspects, individual-specific blood or blood components are used in order to potentially provide individualized BBB-related measures. This can include, for example, the measurement of the permeability of one or more agents or components from the blood or components, the effect of the blood or components on the permeability of one or more agents that may be added to the blood or another fluid included in the device, the effect of the blood or components on the health of the BBB-on-chip or any of its components (whether positive or negative), etc. This may include diagnostic uses, for example, to identify a disease, biomarker or infectious agent carried by the blood or blood components.

BMECs from a MCT8 background were used. FIG. 16A shows the user interface and the conditions during the run of human blood across the blood brain barrier. FIG. 16B shows the setup for measuring the transport of solutes from human blood across the blood brain barrier, a barrier created in vitro in the microfluidic devices describes herein using a layer of BMECs. FIG. 16B shows how human blood was perfused into the bottom channel of the tall chip. In this experiment thyroid hormones were measured by LC-MS/MS as described above. This setup will also be used to test the filtration of proteins across the BBB.

Figure 17A:
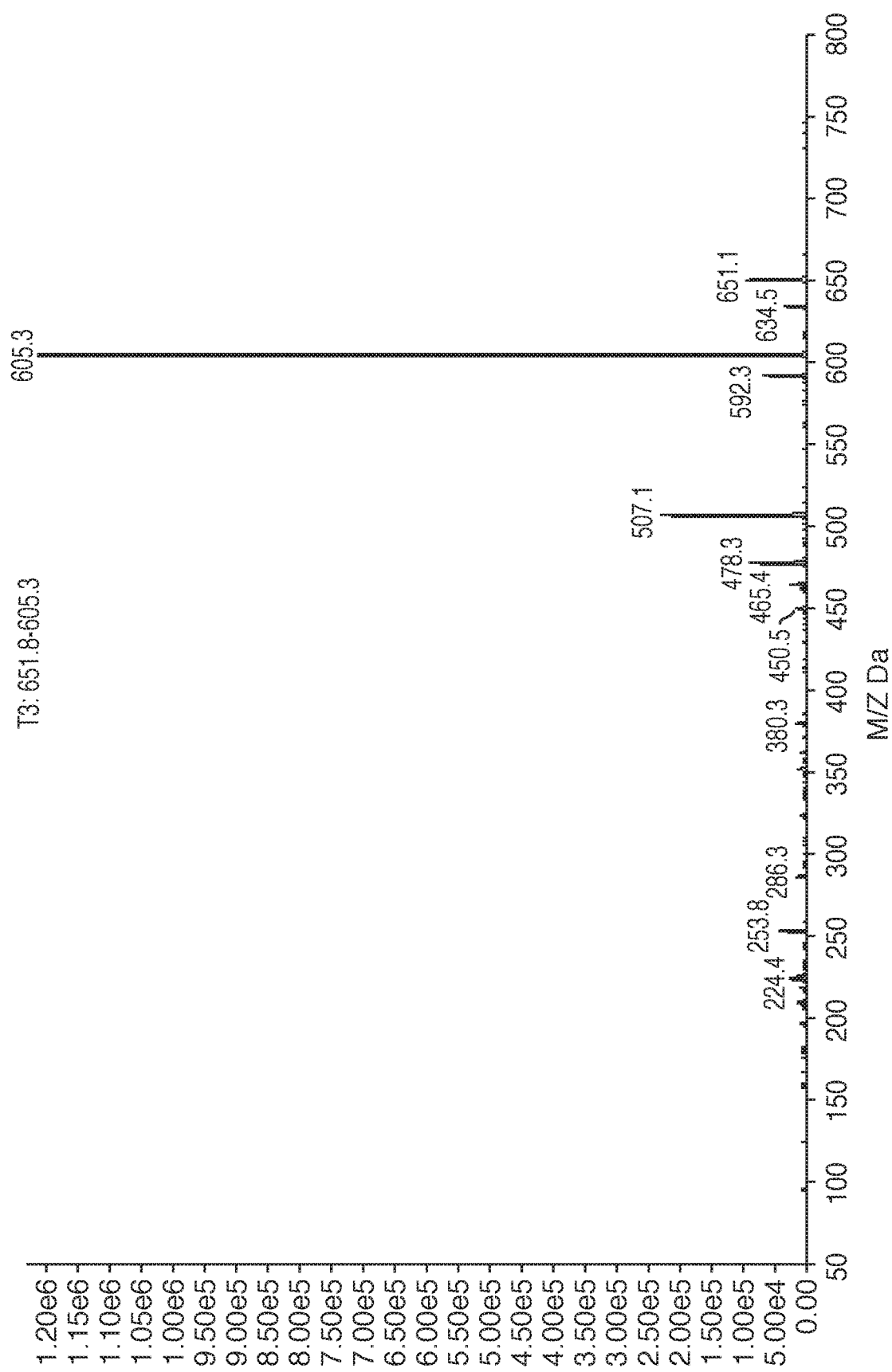
FIG. 17A-C shows the measurement of thyroid hormone transport by mass spectrometry (FIGS. 17A and 17B) using the setup shown in FIG. 16, along with the graphed results (FIG. 17C). After flowing patient blood through the microfluidic chips into the channel under the BMECs, it was possible to measure the transport of compounds from the blood into the neural compartment, i.e. through the BMEC barrier. In this case, the experiment included a control set of BBB-on-chips comprising iPS-derived cells originating from a non-diseased individual, and a second set of BBB-on-chips comprising iPS-derived cells originating from a patient diagnosed with Allan-Herndon-Dudley syndrome (AHDS). The mass-spectrometry data in FIG. 17A is an initial experiment to confirm that the MCT8 transporter defect can be recapitulated on an Organ-Chip.
Figure 17B:
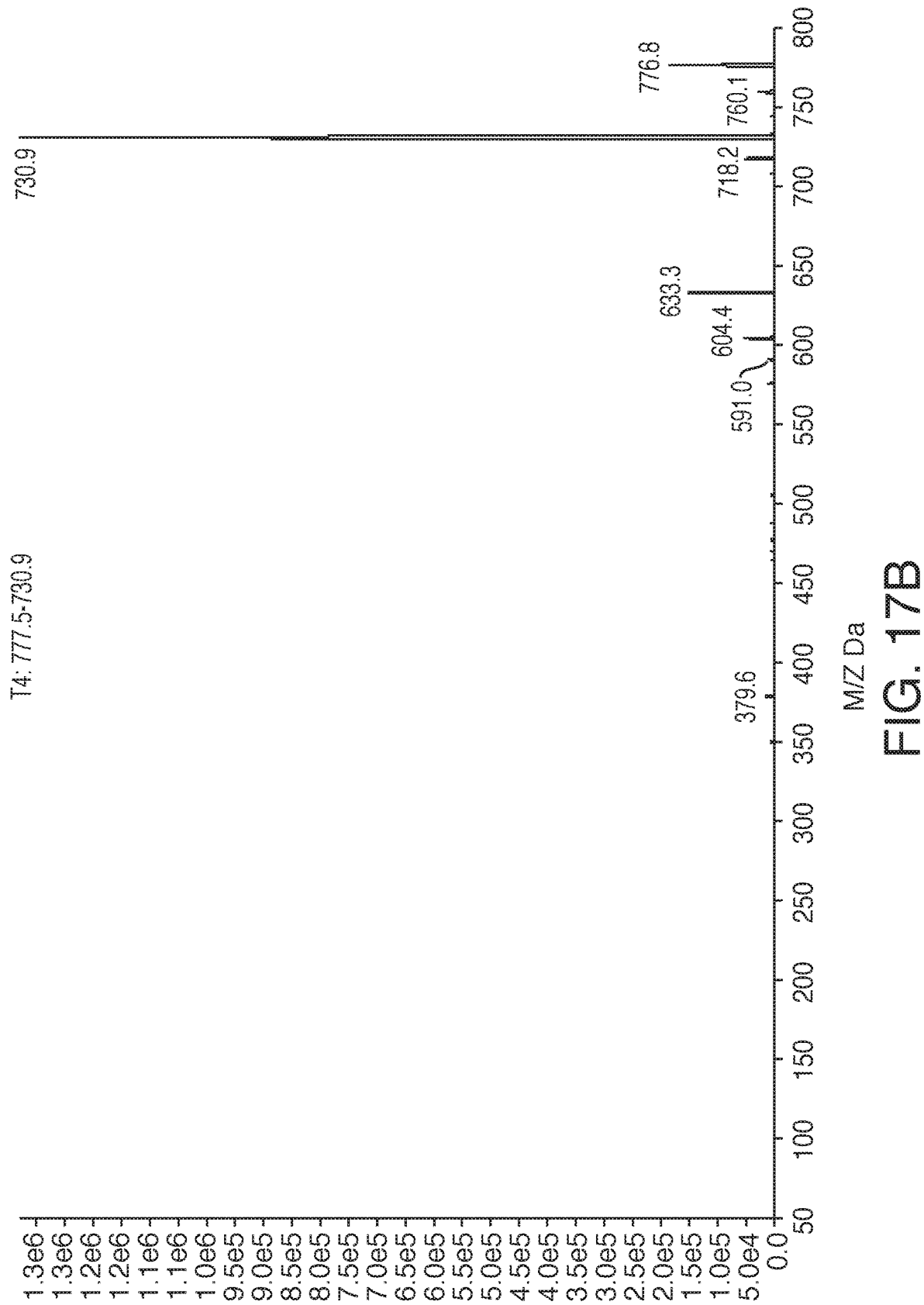
Figure 17C:
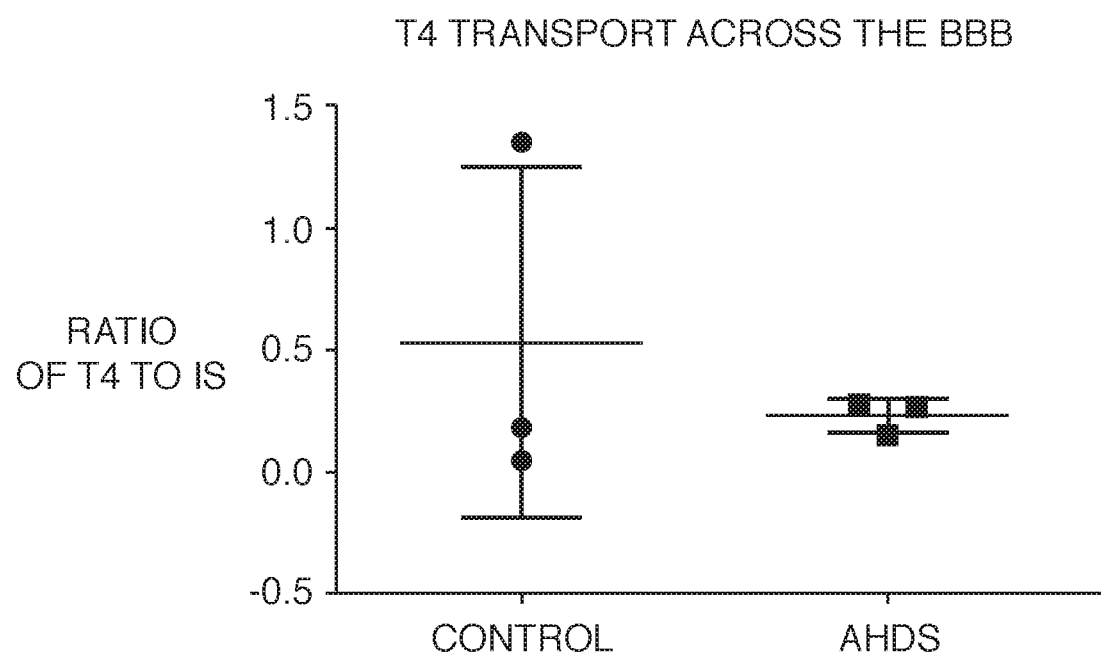

FIG. 17A-C shows the measurement of thyroid hormone transport by mass spectrometry (FIGS. 17A and 17B) using the setup shown in FIG. 16B, along with the graphed results (FIG. 17C). After flowing patient blood through the microfluidic chips into the channel under the BMECs, it was possible to measure the transport of compounds from the blood into the neural compartment, i.e. through the BMEC barrier. In this case, the experiment included a control set of BBB-on-chips comprising iPS-derived cells originating from a non-diseased individual, and a second set of BBB-on-chips comprising iPS-derived cells originating from a patient diagnosed with Allan-Herndon-Dudley syndrome (AHDS). Briefly, iBMECs were generated from a patient with an inactivating genetic mutation in the MCT8 thyroid hormone transporter. This mutation leads to a defect in $T_3/T_4$ transport across the BBB and defects in neural development in patients. The mass-spectrometry data in FIG. 17A is an initial experiment to confirm that the MCT8 transporter defect can be recapitulated on an Organ-Chip.

Example 10

In this example, the disease model was further evaluated. Samples were prepared by taking 100 ul of each sample of T3 and mixing it with the equivalent sample of T4. This was done for each sample and also for the calibration curve. Proteins and salts were precipitated from the solution; the samples were dried and resuspended in the same volume. The calibration curve permitted the calculation of the concentrations (in mM) for both T3 and T4.

For the T3/T4 experiments, the following 4 conditions were tested in the microfluidic chip:
1. 1 nM T3 in normal media in the bottom channel and media without T3 on top channel. Both sides were running at a 30 ul/hr flow rate.
2. 100 nM T3 and T4 in normal media in the bottom channel and media without T3 on top channel. Again, both sides were running at a 30 ul/hr flow rate.
3. Human plasma on bottom channel at 90 ul/hr and media without T3 on top channel kept static for 1 hour.
4. Human plasma on bottom channel at 90 ul/hr and media without T3 on top channel kept static for 1 hour.

For each experiment, Dextran-FITC was used in the bottom channel to correct for paracellular diffusion.

Figure 21:
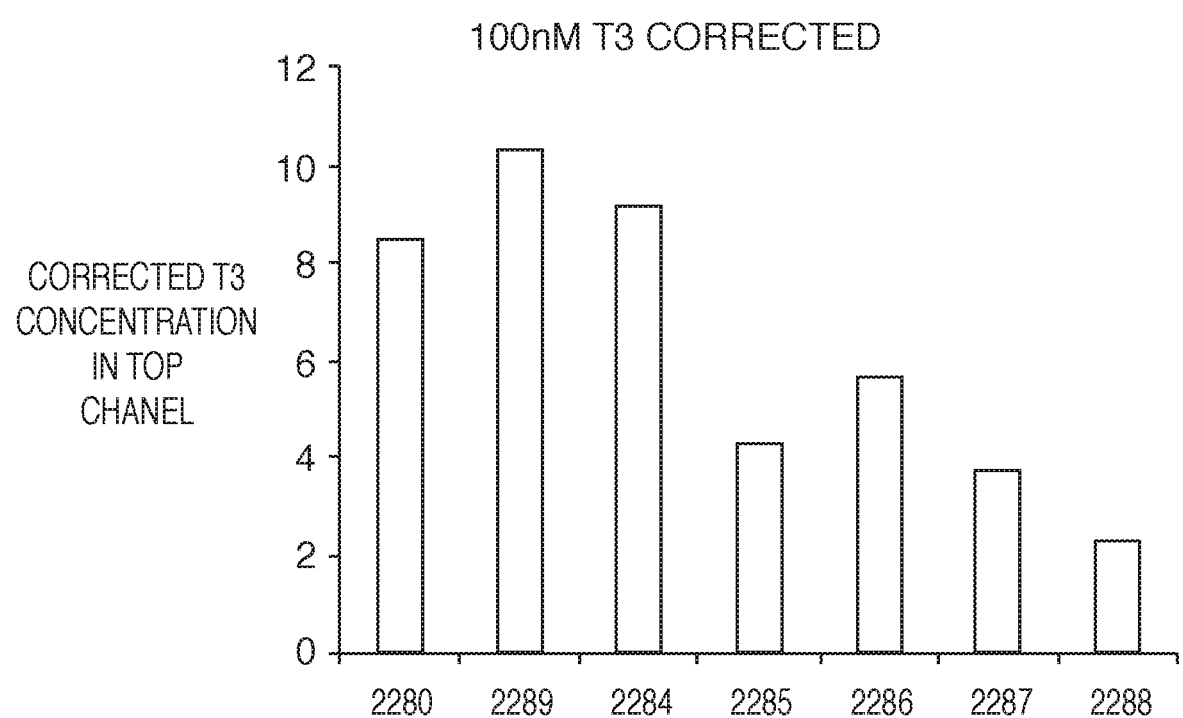
FIG. 21 shows the corrected T3 concentration in the top channel of seven different chips, i.e. chips populated with normal cells (2280, 2289 and 2284) as compared to chips populated with cells from an MCT8 cell line or patient (2285-2288).
Figure 22B:
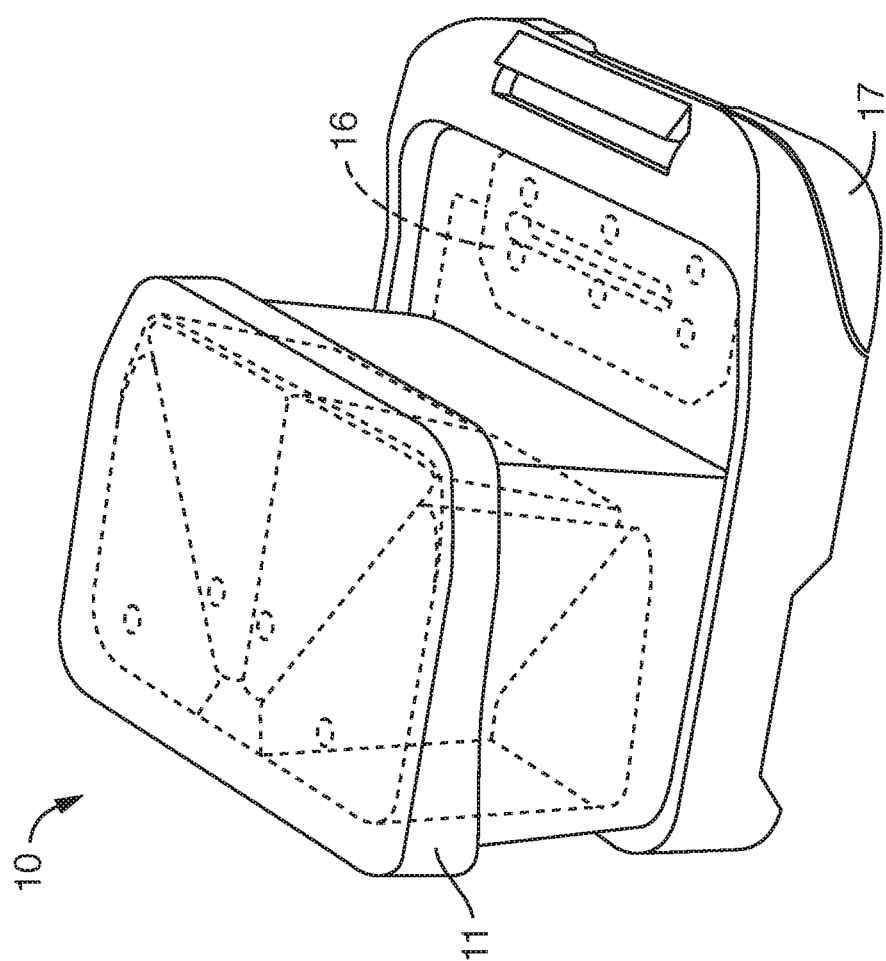
FIG. 22B is a topside schematic of an embodiment of the perfusion disposable or "pod" (10) featuring the transparent (or translucent) cover (11) over the reservoirs, with the chip (16) inserted in the carrier (17). The chip can be seeded with cells and then placed in a carrier for insertion into the perfusion disposable or pod, whereupon culture media in the reservoirs flows into the microchannels and perfuses the cells (e.g. both BMECs and MNs).
Figure 22A:
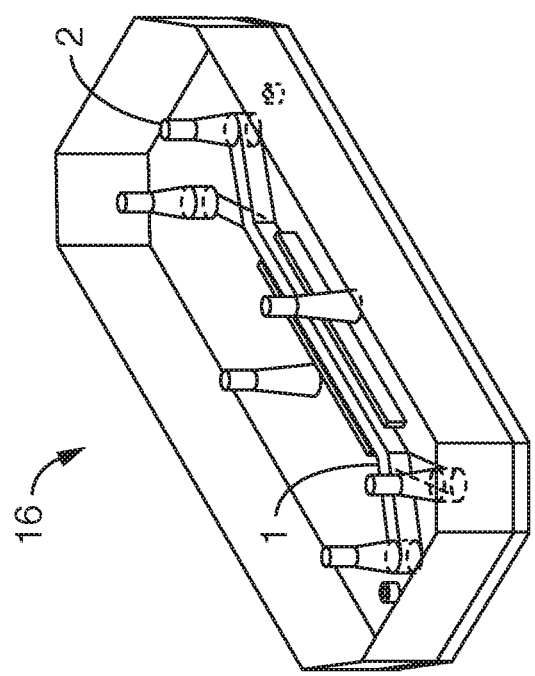
FIG. 22A is a schematic showing one embodiment of the microfluidic device or chip (16), comprising two microchannels (1), each with an inlet and outlet port (2), as well as (optional) vacuum ports.
Figure 23A:
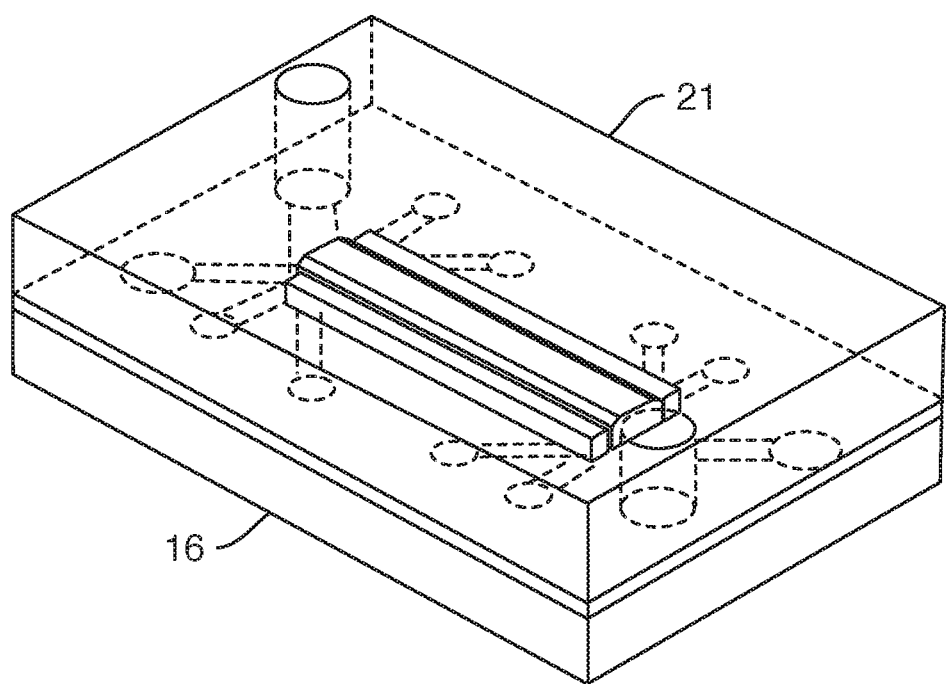
FIG. 23A-B shows a schematic of an illustrative microfluidic device or "organ-on-chip" (16) device. The assembled device is schematically shown in FIG. 23A with the top surface (21) indicated.
Figure 23B:
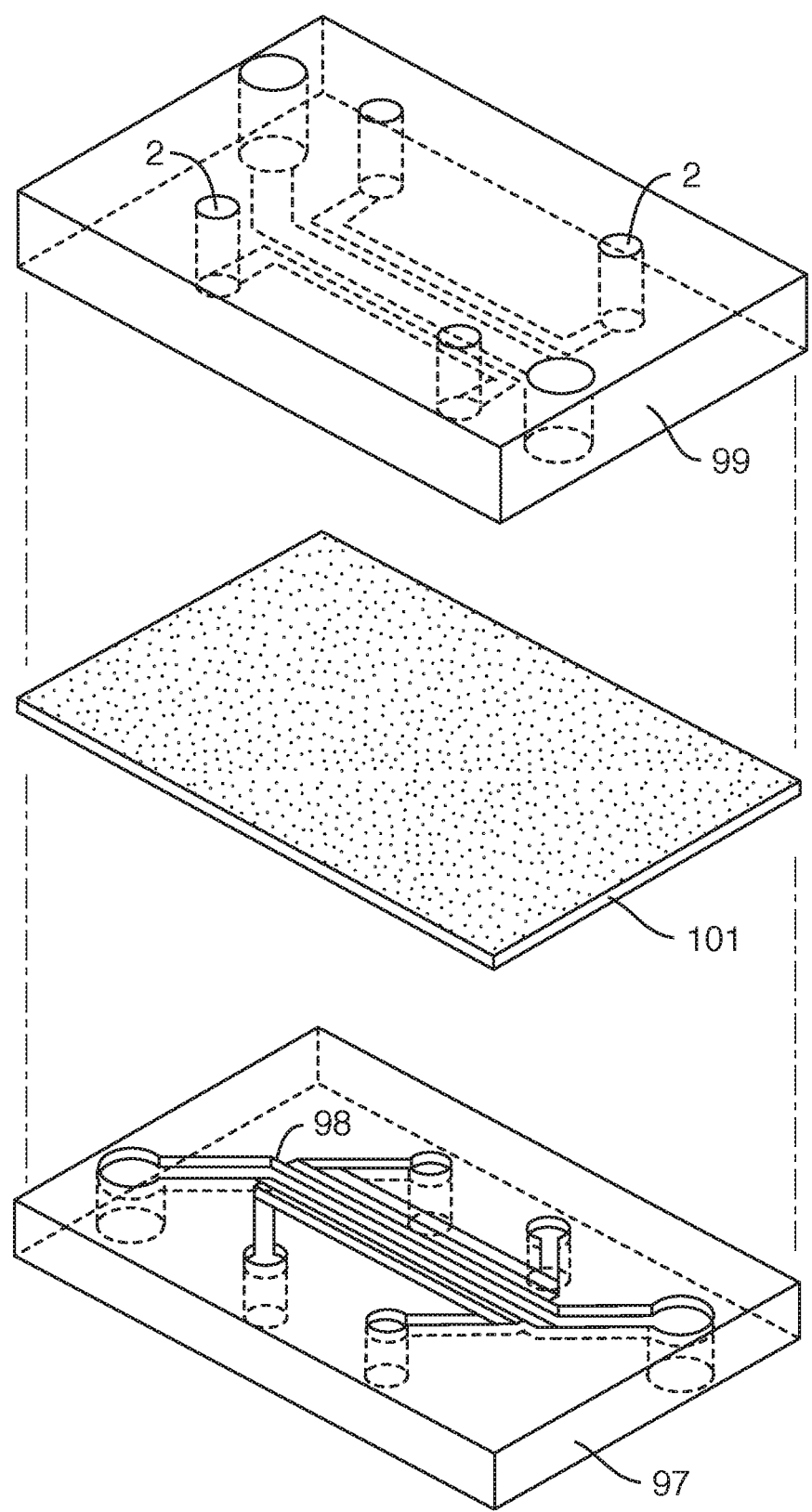

From the above-mentioned 4 conditions, only 100 nM was significantly above detection and these worked well as shown in FIG. 21. Chips 2280, 2289, and 2284 are populated with cells from a single control line. Chips 2285 and 2286 are populated with cells from the isogenic mutated MCT8 line. Chips 2287 and 2288 are populated with cells from a mutated MCT8 patient. FIG. 21 is a bar graph showing the corrected T3 concentration in the top channel of each chip. Clearly, there is reduced T3 transport in mutated MCT8 lines as compared to normal, demonstrating one aspect of disease modeling using the blood-brain barrier, organ-on-chip device.

Example 11

In one embodiment, the present invention contemplates contact of neurons and brain related vascular cells, and more preferably, direct contact of iMNs and iBMECs on the microfluidic chip to enhance neuronal physiology as measured by electrophysiology and transcriptomics. It has been found that the chip accelerates diMN electrophysiological maturation.

In this experiment, diMNs seeded into the chip were recorded after 12 days after seeding. FIG. 24 provides a whole cell patch clamp recording of a non-invoked spontaneously active neuron showing highly complex and repetitive bursts of neuronal activity indicative of neuronal networks being established in the chip.

When induced to fire by injecting current into the neuron at day 6 in chip, more resolved action potentials are observed (FIG. 25B) compared to traditional culture (FIG. 25A).

Figure 26A:
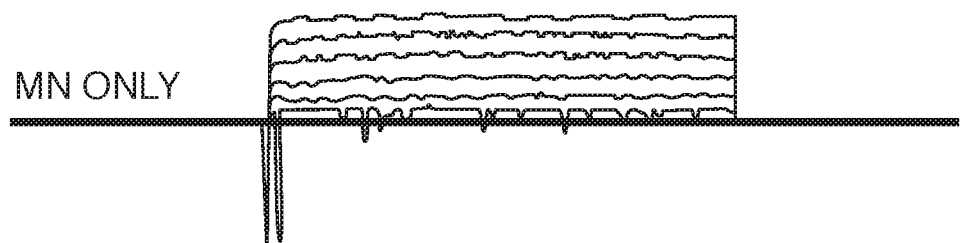
FIG. 26A-B shows print outs of electrophysiological data from neurons cultured alone (FIG. 26A, top panel) and co-cultured with BMECs (FIG. 26B, bottom panel) in a microfluidic device or chip, showing that neural tissue have more mature electrophysiological properties in the chip when in co-culture with BMECs.
Figure 26B:
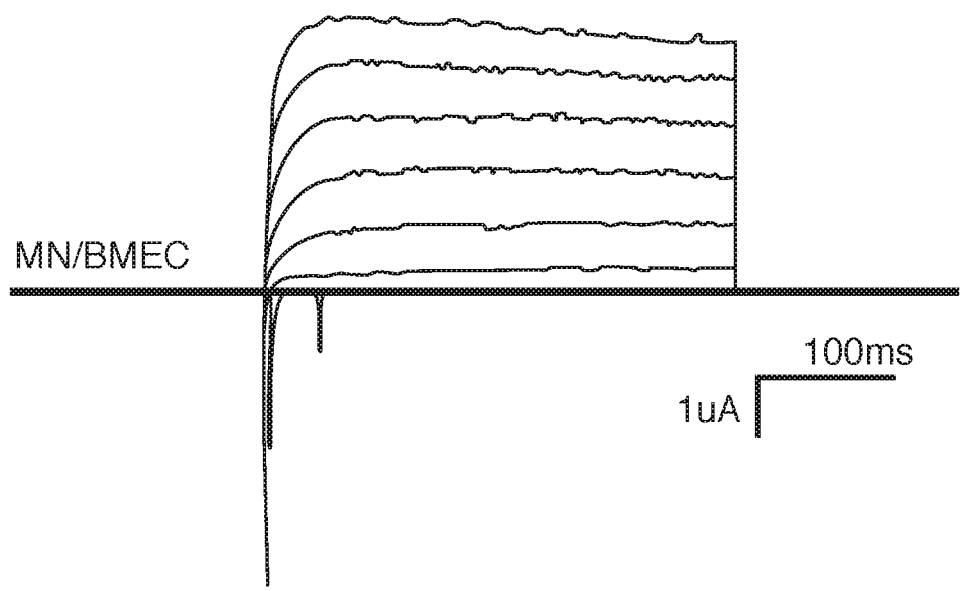
Figure 27A:
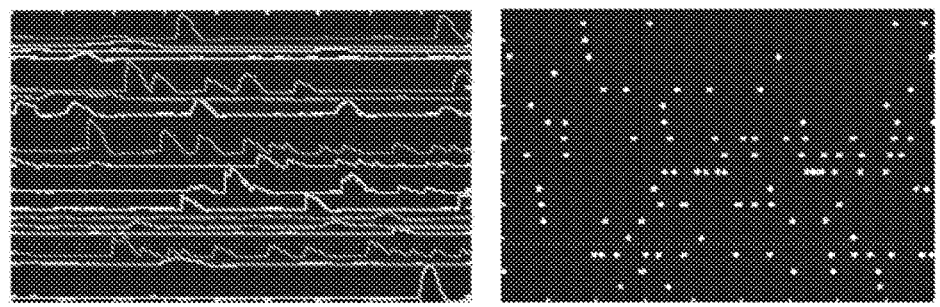
FIG. 27A-D provides neural calcium measurement readouts comparing neurons (MN) co-cultured with BMECs (FIG. 27D, bottom panel), cultured alone (FIG. 27C, first panel up from the bottom panel), cultured in endothelial cell conditioned medium or ECCM in a (96-well) static culture (FIG. 27B, second panel up from the bottom panel), along with an unconditioned media (96-well) static control (FIG. 27A, top panel). Each neuron's activity is simultaneously tracked and analyzed (calcium influx is an indirect measure for neuronal activity that can be observed live in the chip). The results show that co-culture increases diMN neural calcium transient activity, i.e. a significant increase in transient frequency is observed upon contact of MNs with iBMECs.
Figure 27B:
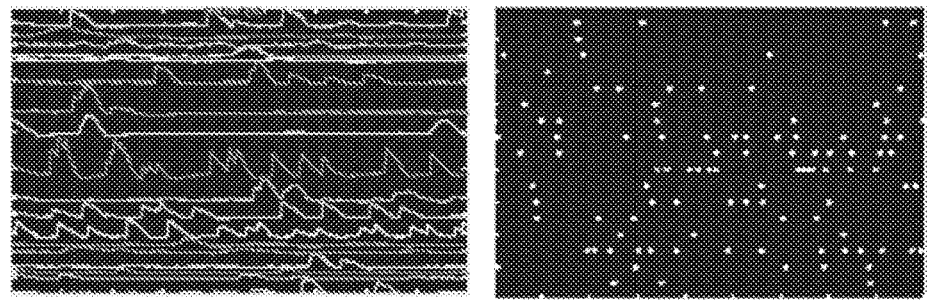
Figure 27C:
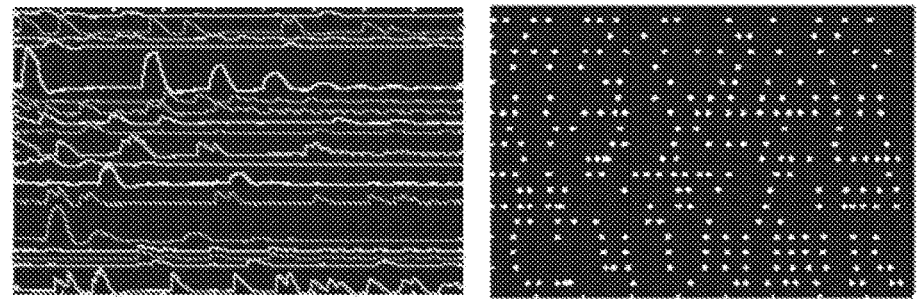
Figure 27D:
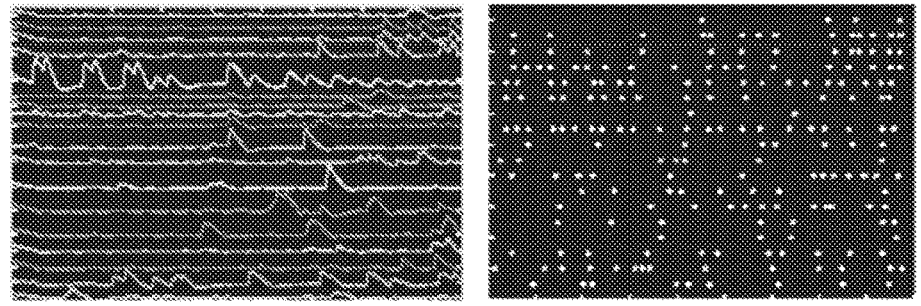

Neurons that are co-cultured with BMECs in chip (MN/BMEC) show more pronounced currents (FIG. 26B) than MNs cultured alone (FIG. 26A) on chip (MN Only) as depicted by current traces recorded as the neuron is induced to fire an action potential. These observed electrophysiological properties are well established in the field as indicating neurons are more mature at this time point.

Example 12

In a controlled study, calcium influx live cell imaging was performed on diMNs that had been cultured in the chip (MN Chip) and in co-culture with BMECs (MN/BMEC). Neuron calcium influx was recorded as described previously, and plotted with respect to time (FIG. 27A-D, right panels). Calcium influx events or peaks correspond to neural activity and were counted by both automated software and blinded human technician. Each event was assigned a time-stamped value and depicted for each tracked neuron with respect to time.

Figure 28:
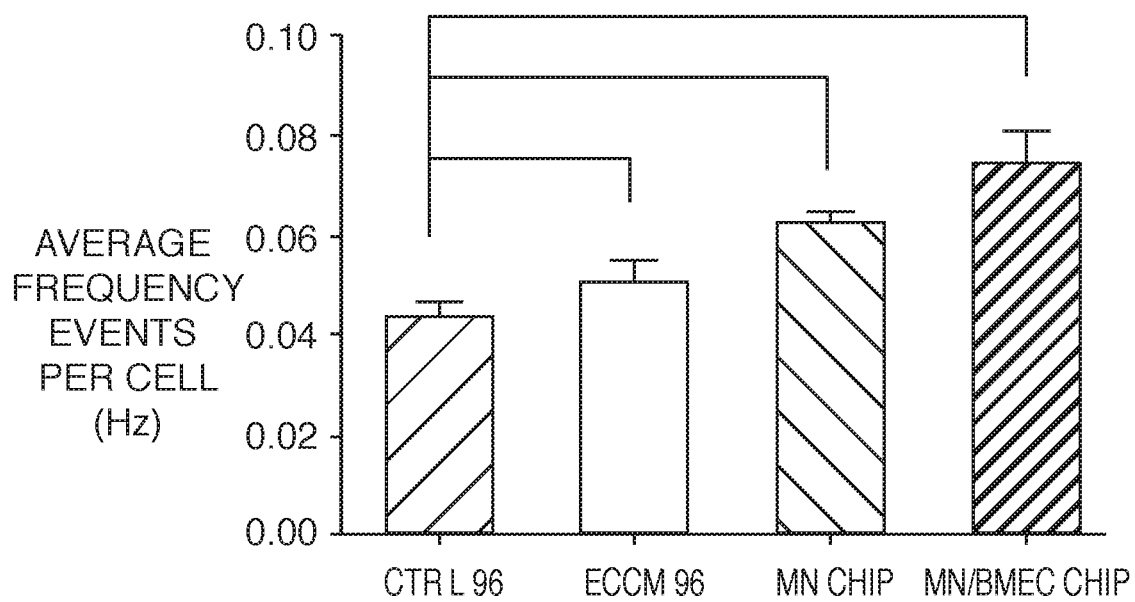
FIG. 28 is a bar graph of neural calcium measurements (average frequency events per cell) comparing neurons (MN) co-cultured with BMECs (far right), cultured alone (next bar to the left), cultured in endothelial cell conditioned medium or ECCM in a static culture (next bar to the left), along with an unconditioned media static control (far left). The results show that co-culture increases diMN neural calcium transient activity, i.e. a significant increase in transient frequency is observed upon contact of MNs with iBMECs.

FIG. 28 is a bar graph showing that the frequency of recorded neurons on the chip is significantly increased in both chip conditions compared to traditional 96 well culture control (CTRL 96). This increase was not observed in 96 well cultures that had been treated with media preconditioned with BMECs (ECCM 96) indicating the increase in the neurons ability to flux was achieved exclusively in the chip. This effect was further increased with the addition of BMECs to the chip in co-culture. Increased frequency is known to occur in vivo as MNs mature and indicate neurons mature faster in the chip.

Example 13

Figure 29A:
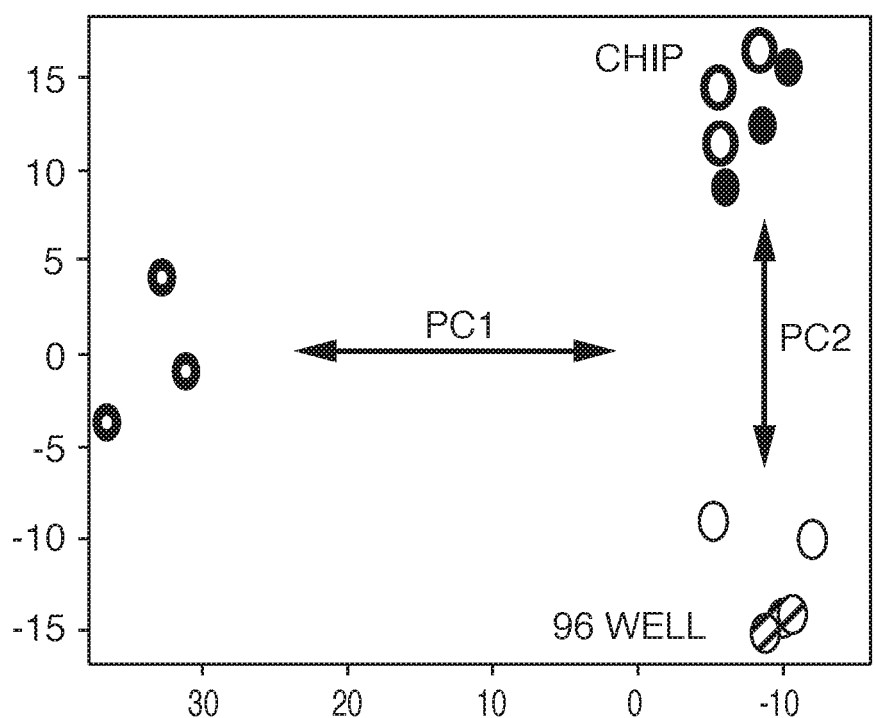
FIG. 29A-B shows the results of a transcriptomic study of iMNs in a microfluidic chip. Neurons were either cultured alone (FIG. 29A, top box) on the chip or in a co-culture with BMECs (FIG. 29B, bottom box), and this was compared with a 96-well static culture. The MNs were sorted on a FACS and RNA was sequenced (i.e. gene expression was detected). RNA-Seq from FACS sorted MNs show that neural development gene pathways (PC1) are upregulated in chip. Vascular interaction genes (PC3) are recreated in co-culture with iBMECs. In addition, there are chip induced genes (PC2), i.e. gene activity induced in the cells simply from being cultured on the chip.
Figure 29B:
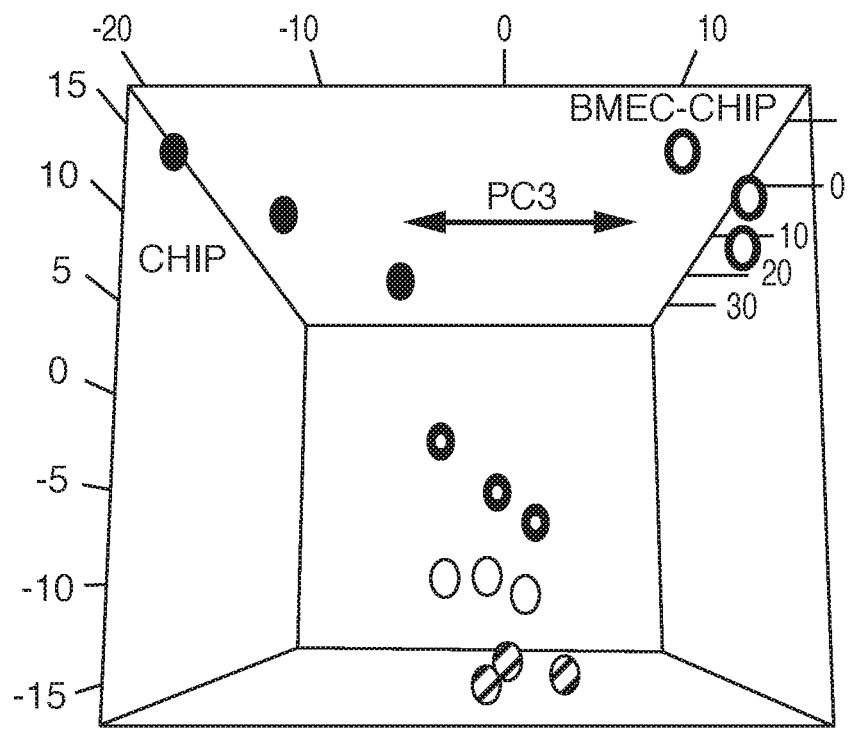

In this experiment, diMNs were stably transfected with a nuclear-tagged GFP reporter transgene and seeded on the top channel. NON-GFP BMECs were seeded into the bottom channel. Chips were allowed to mature either in this configuration, or non-BMEC controls (both diMN only on chip and diMN in a standard 96 well plate). The cells were FACS sorted to purify the diMN cultures away from the NON-GFP BMECs after 6 days on the chip. These purified cells were mRNA sequenced in all conditions, and a non-biased principle component analysis (PCA) was conducted on all samples. The first principle components separated the conditions by different genes expressed. PC1 separates all cultures from a progenitor pool (black) PC2 genes separated 96-well culture from diMNs in chip, and PC3 separated genes that were exclusively expressed in co-culture with BMECs (FIG. 29A-B).

The top 200 highly expressed genes and bottom 100 low expressed genes from each PC were entered into the non-biased gene ontology platform DAVID. The resulting pathways included increased neural differentiation in the chip-specific PC2 gene set (FIG. 30, middle list). Vascular interaction gene pathways were found in the co-culture chips indicating that known in vivo gene pathways between the vascular system and neurons were recapitulated in the chip device. The colored bars on the right in FIG. 30 represent the expression of each gene (row) in each of the 5 conditions (columns). Column order is MN Only, BMEC/MN, 96-well control, 96 well ECCM, MN progenitor. Red=high and blue=low. These vascular gene pathways have not been shown to be induced in any other culture system and may be inducing the observed increase in maturity and activity.

The invention claimed is:

1. A method of culturing cells, comprising:
   a) providing a microfluidic device comprising a porous membrane, said membrane comprising a top surface and a bottom surface;
   b) seeding brain microvascular endothelial cells on said bottom surface so as to create seeded-cells on said bottom surface of said membrane;
   c) seeding stem cell-derived neuronal cells or neuronal cells differentiated from stem cells on said top surface to create seeded cells on said top surface of said membrane; and
   d) culturing said top surface seeded cells under flow conditions that support the maturation of neurons and culturing said bottom surface seeded cells under conditions that support maturation of said brain microvascular endothelial cells wherein said neurons exhibit a more mature electrophysiology, in terms of one or more features selected from the group consisting of action potential patterns, negative sodium channel current, positive potassium channel current and action potential spikes of amplitude, duration and frequency, or increased frequency after exposure to said flow as compared to the same neurons cultured in a static culture.

2. The method of claim 1, further comprising e) seeding astrocytes to create seeded astrocyte cells.

3. The method of claim 2, further comprising culturing said astrocytes under conditions such that an astrocyte or portion thereof transmigrates said membrane and contacts one or more said brain microvascular endothelial cells on said bottom surface.

4. The method of claim 1, wherein said stem cell-derived cells are derived or extracted from EZ spheres, iNPCs or iMNPs, and/or wherein said seeded cells in step c) are human cells.

5. A method of culturing cells, comprising:
a) providing a microfluidic device comprising a porous membrane, said membrane comprising a top surface and a bottom surface;
b) coating said top surface of said membrane with laminin and said bottom surface with a mixture of collagen and fibronectin, said mixture free of laminin;
c) seeding induced neural progenitor cells on said top surface and brain microvascular endothelial cells on said bottom surface so as to create seeded cells;
d) exposing said seeded cells to a flow of culture media; and
e) culturing said seeded cells to exhibit a more mature electrophysiology as compared to the same neurons cultured in a static culture.

6. The method of claim 5, wherein said induced neural progenitor cells are derived from induced pluripotent stem cells from a human patient diagnosed with a central nervous system (CNS) disorder.

7. The method of claim 5, wherein said flow promotes the differentiation of said induced neural progenitor cells.

8. The method of claim 7, wherein said induced neural progenitor cells differentiate into neurons.

9. The method of claim 8, wherein said neurons exhibit a more mature electrophysiology in terms of action potential patterns after exposure to said flow as compared to the same neurons cultured in a static culture.

10. The method of claim 5, wherein said induced neural progenitor cells are derived from induced pluripotent stem cells from a patient diagnosed with Amyotrophic lateral sclerosis (ALS).

11. The method of claim 5, wherein said brain microvascular endothelial cells are derived from induced pluripotent stem cells from a patient diagnosed with MCT8-specific thyroid hormone cell-membrane transporter deficiency and/or wherein the seeded cells are cultured such that said brain microvascular endothelial cells on said bottom surface form tight junctions.

12. The method of claim 5, wherein said induced neural progenitor cells were stored frozen and then thawed prior to step c).

13. The method of claim 5, wherein said more mature electrophysiology comprises one or more features selected from the group consisting of action potential patterns, negative sodium channel current, positive potassium channel current and action potential spikes of amplitude, duration and frequency that are similar to neurons in a physiological environment, or an increased frequency as compared to the same neurons cultured in a static culture.

* * * * *